(12) United States Patent
Sugiyama

(10) Patent No.: US 12,171,528 B2
(45) Date of Patent: Dec. 24, 2024

(54) BLOOD VESSEL WALL THICKNESS ESTIMATION METHOD, BLOOD VESSEL WALL THICKNESS ESTIMATION DEVICE, AND BLOOD VESSEL WALL THICKNESS ESTIMATION SYSTEM

(71) Applicant: OSAKA UNIVERSITY, Osaka (JP)

(72) Inventor: Yoshie Sugiyama, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 417 days.

(21) Appl. No.: 17/628,394

(22) PCT Filed: Feb. 19, 2020

(86) PCT No.: PCT/JP2020/006394
§ 371 (c)(1),
(2) Date: Jan. 19, 2022

(87) PCT Pub. No.: WO2021/019809
PCT Pub. Date: Feb. 4, 2021

(65) Prior Publication Data
US 2022/0280049 A1 Sep. 8, 2022

(30) Foreign Application Priority Data
Aug. 1, 2019 (JP) ................................. 2019-142321

(51) Int. Cl.
*A61B 5/00* (2006.01)
*A61B 5/02* (2006.01)
(Continued)

(52) U.S. Cl.
CPC .......... *A61B 5/02007* (2013.01); *A61B 5/055* (2013.01); *G06T 7/0012* (2013.01); *G06T 2207/30101* (2013.01)

(58) Field of Classification Search
CPC ....... A61B 5/02007; A61B 5/055; A61B 6/03; G06T 7/0012; G06T 2207/30101; G06T 7/62
See application file for complete search history.

(56) References Cited

U.S. PATENT DOCUMENTS

2015/0327780 A1* 11/2015 Kano .................... A61B 90/37
600/407

FOREIGN PATENT DOCUMENTS

| JP | 2013-118932 | 6/2013 | |
|---|---|---|---|
| WO | WO-2015041312 A1 * | 3/2015 | ........... A61B 5/0035 |
| WO | WO-2017198490 A1 * | 11/2017 | ......... A61B 5/02007 |

OTHER PUBLICATIONS

Roytvarf et al, A Large-Scale, Energetic Model of Cardiovascul Homeostasis Predicts Dynamics of Arterial Pressure in Humans, IEEE Transactions on Biomedical Engineering, vol. 55, No. 2, Feb. 2008.*

(Continued)

*Primary Examiner* — Ping Y Hsieh
*Assistant Examiner* — Xiao Liu
(74) *Attorney, Agent, or Firm* — Wenderoth, Lind & Ponack, L.L.P.

(57) ABSTRACT

A blood vessel wall thickness estimation method includes: obtaining behavioral information, which is numerical information about changes over time in positions of a plurality of predetermined points in a blood vessel wall, based on a video including the blood vessel wall obtained using four-dimensional angiography; generating estimation information for estimating a thickness of the blood vessel wall based on the behavioral information obtained in the obtaining; and outputting the estimation information generated in the generating. The estimation information is information in which at least one of the following is visualized: a change in displacement over time; a change in speed over time; a (Continued)

change in acceleration over time; a change in kinetic energy over time; a spring constant obtained from the displacement and the acceleration, and a Fourier coefficient obtained from the change in the displacement over time.

8 Claims, 56 Drawing Sheets

(51) Int. Cl.
 *A61B 5/055* (2006.01)
 *G06T 7/00* (2017.01)

(56) References Cited

OTHER PUBLICATIONS

International Search Report (ISR) issued on May 26, 2020 in International (PCT) Application No. PCT/JP2020/006394.

* cited by examiner

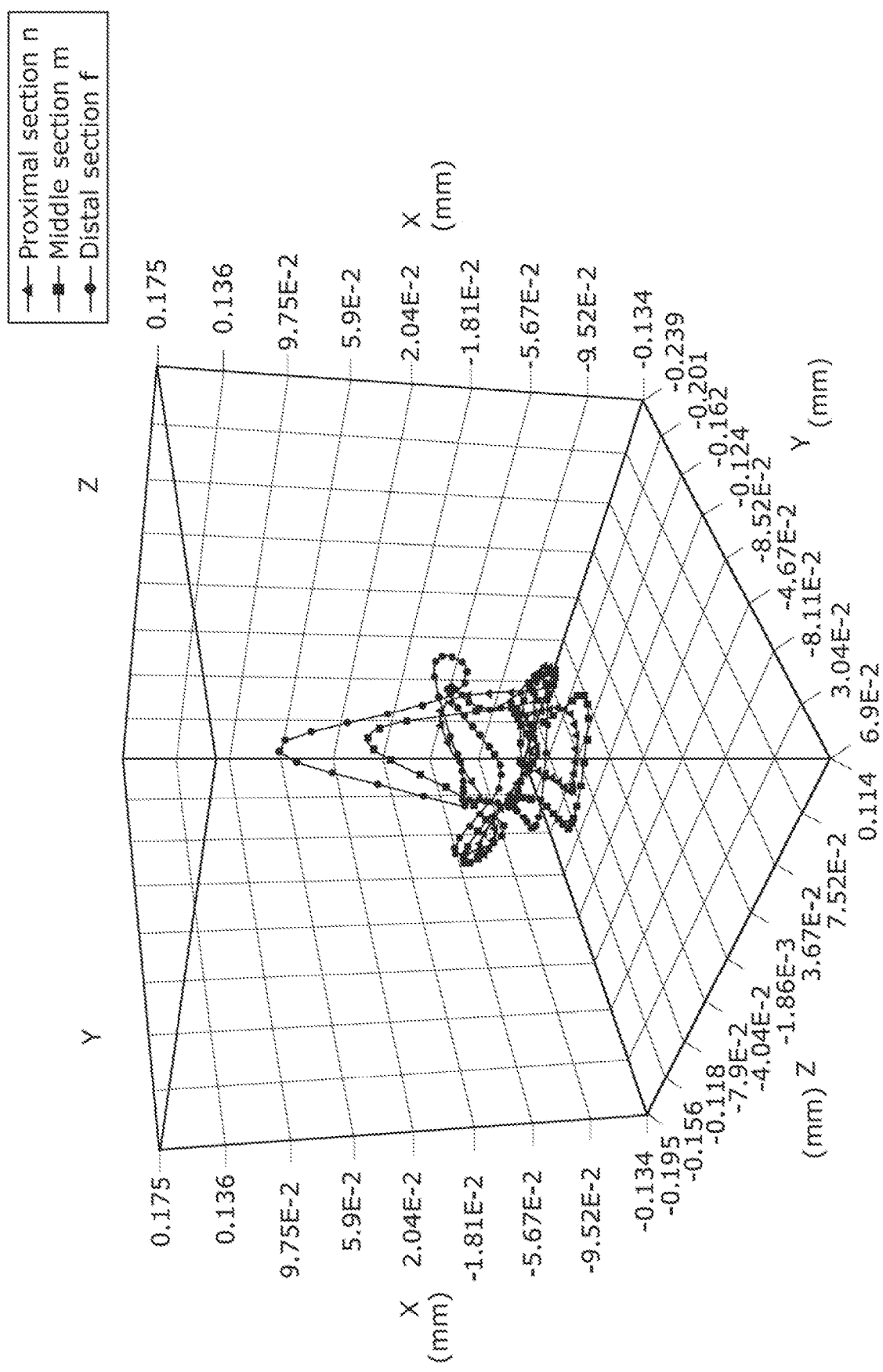

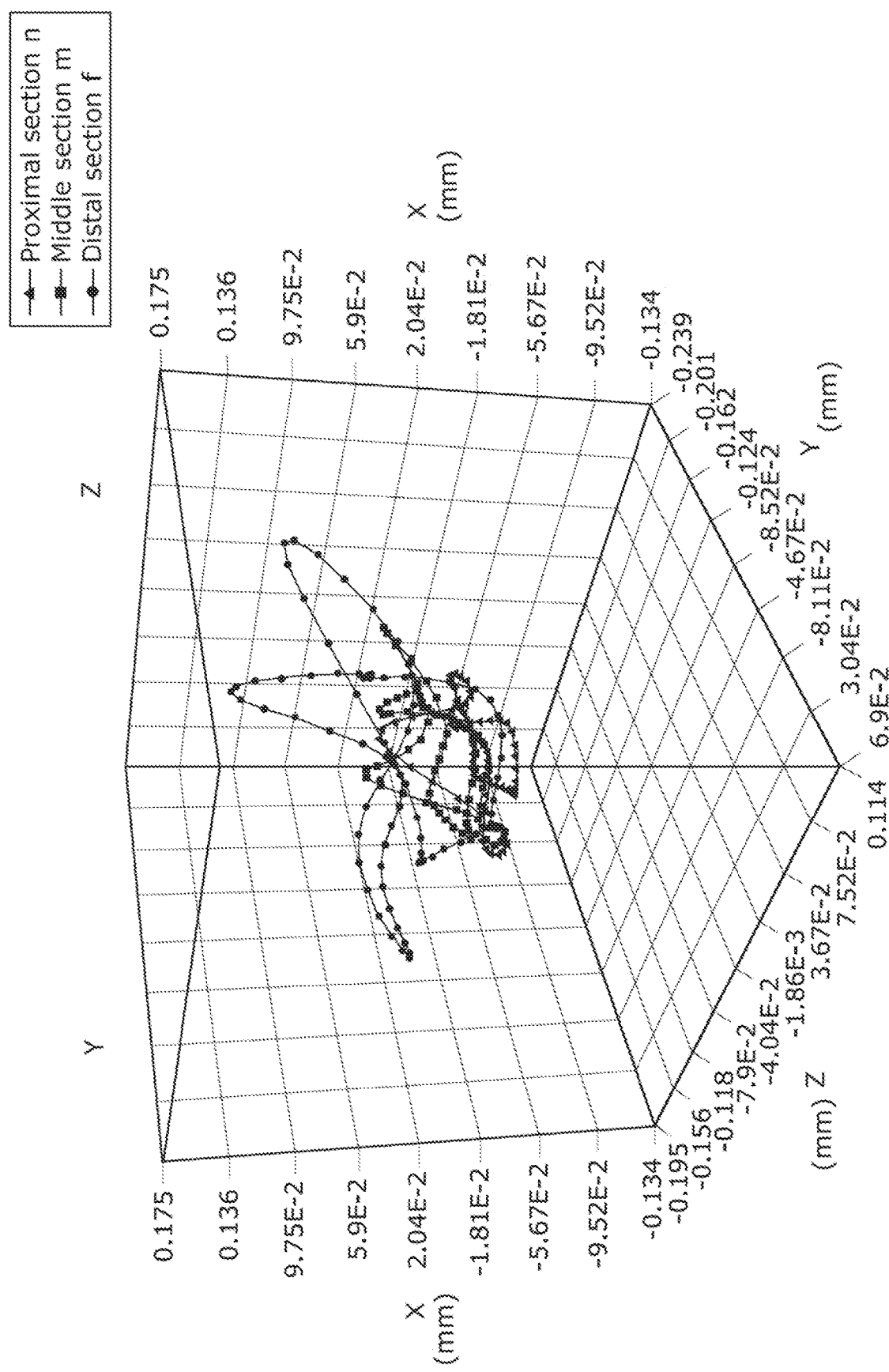

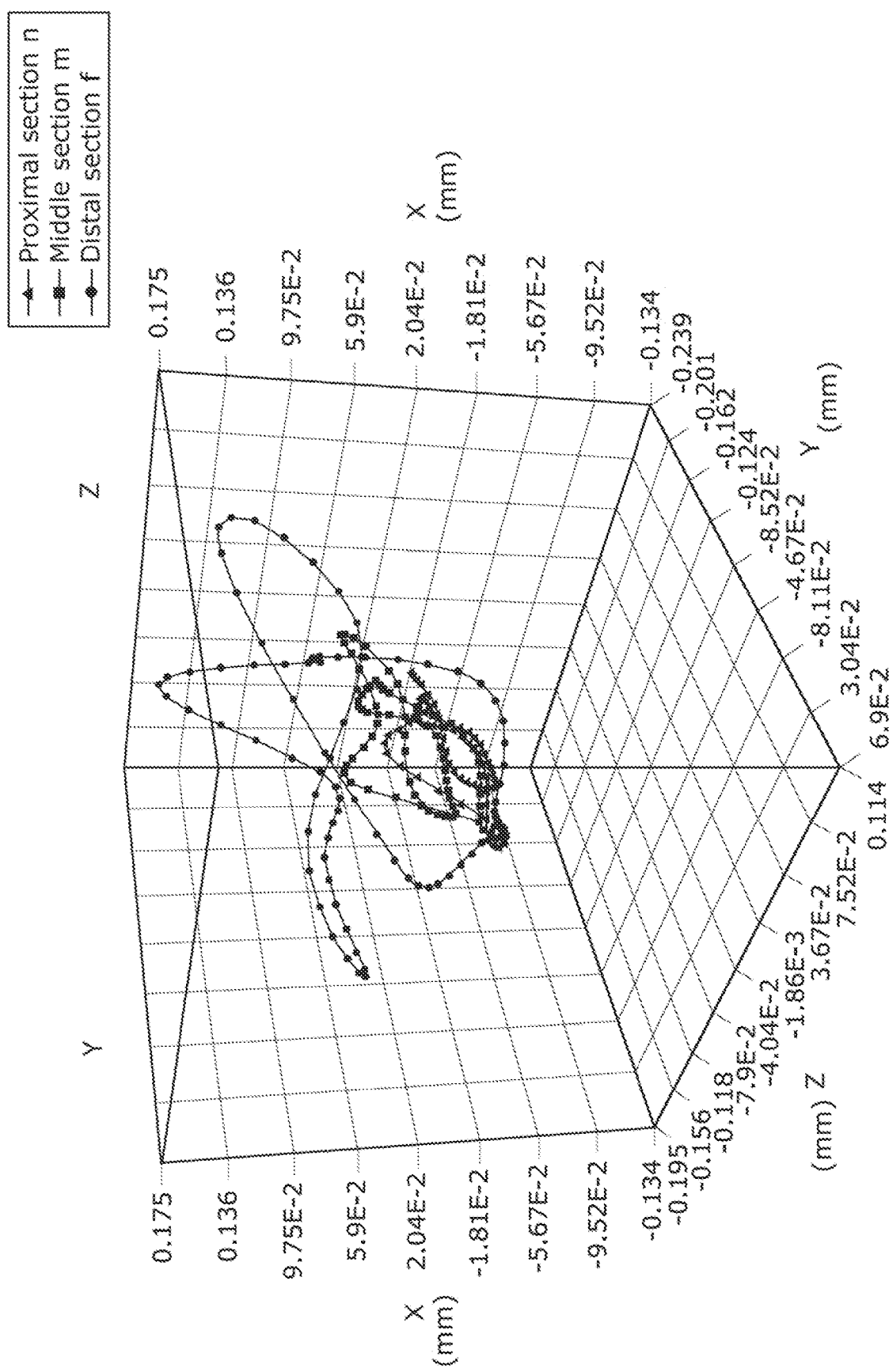

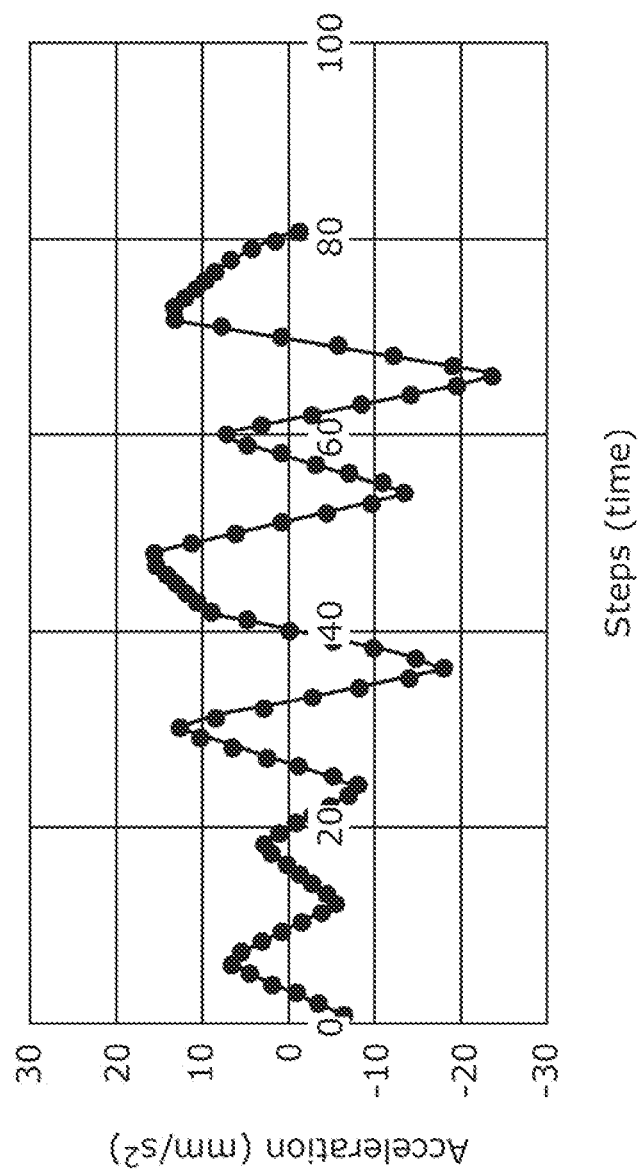

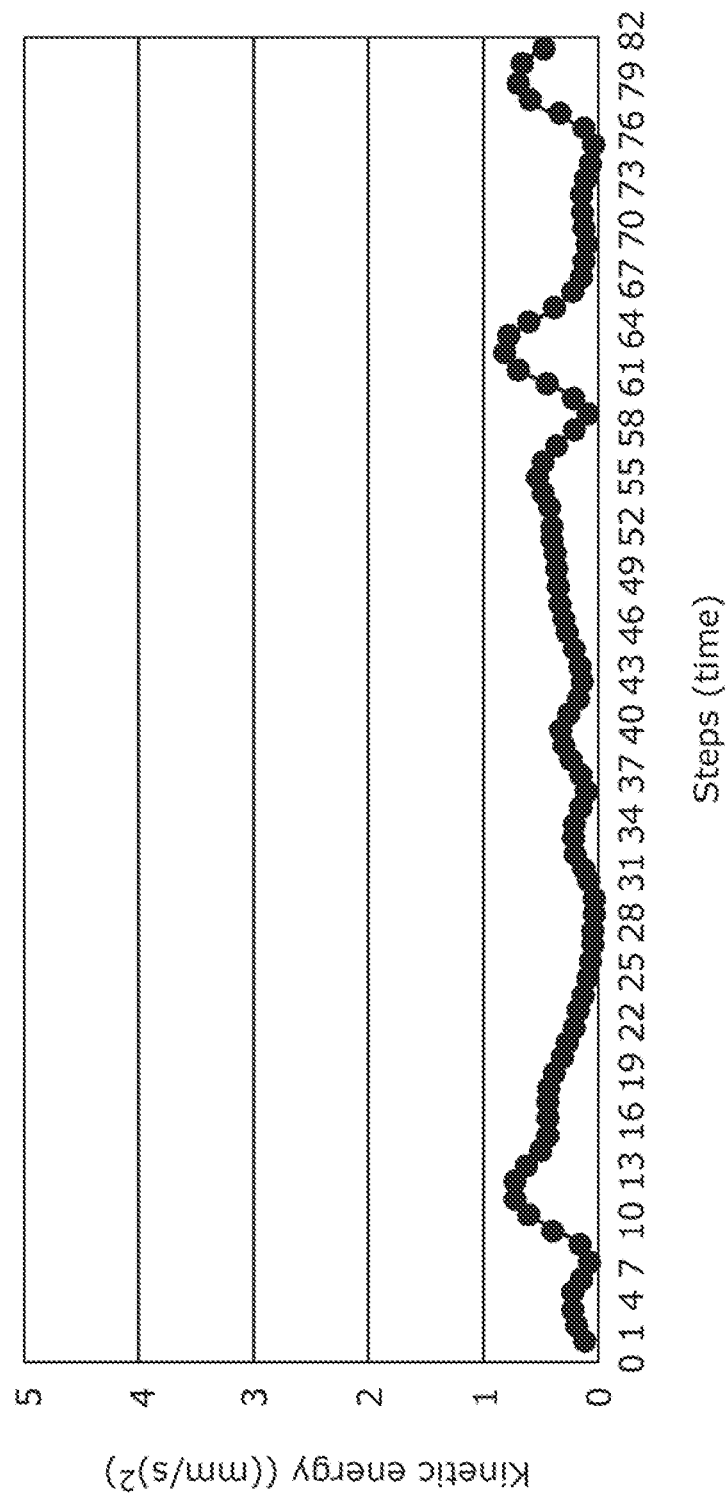

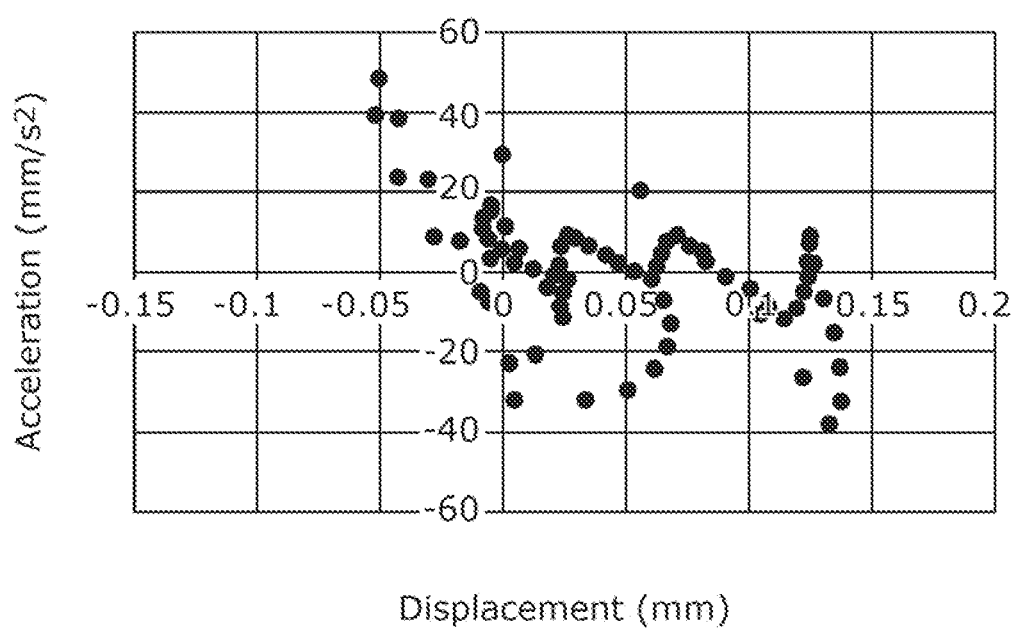

BLOOD VESSEL WALL THICKNESS ESTIMATION METHOD, BLOOD VESSEL WALL THICKNESS ESTIMATION DEVICE, AND BLOOD VESSEL WALL THICKNESS ESTIMATION SYSTEM

TECHNICAL FIELD

The present invention relates to a blood vessel wall thickness estimation method and the like.

BACKGROUND ART

A cerebral aneurysm, which is one vascular disease, is an extremely high-risk disease with a fatality rate of more than 50% once it ruptures, and it is also a socially significant disease due to its high rate of aftereffect. For this reason, prophylactic treatment (preemptive medicine) to prevent rupture of cerebral aneurysms is very important, and proper therapeutic intervention is essential.

For proper treatment, it is useful to know information about (for example, the thickness of) the wall of the cerebral aneurysm. This is because it is known that a cerebral aneurysm is more likely rupture in areas with thin walls than in areas with thick walls. However, even within a single aneurysm, the geometry, including the thickness, of the aneurysm wall varies from aneurysm to aneurysm. It is therefore difficult even for experts to infer information about the geometry, including the thickness, of the aneurysm wall only from the shape of the lumen or the like of the aneurysm wall obtained by computed tomography (CT) and magnetic resonance imaging (MRI).

For example, one known method of measuring the thickness of the wall of a cerebral aneurysm is through imaging or visual inspection in craniotomy performed by a doctor. However, this method is highly invasive, places a heavy burden on the patient, and is not a method by which the thickness of the wall of a cerebral aneurysm can be easily measured.

One example of a known minimally invasive method of measuring the thickness of a blood vessel wall, such as the wall of a cerebral aneurysm, is the ultrasonic diagnostic apparatus disclosed Patent Literature (PTL) 1. PTL 1 discloses an ultrasonic diagnostic apparatus that generates image data using ultrasonic signals and displays information about the thickness of a blood vessel wall of a subject based on the image data.

CITATION LIST

Patent Literature

[PTL 1] Japanese Unexamined Patent Application Publication No. 2013-118932

SUMMARY OF INVENTION

Technical Problem

Unfortunately, the image data obtained using the technique disclosed in PTL 1 is less precise, and therefore, it is difficult to obtain highly accurate information about the blood vessel wall.

In view of this, the present invention has an object to provide a method and the like that can generate highly accurate information about the blood vessel wall using a minimally invasive method, thereby providing useful information for applying specific measures for blood vessel diseases.

Solution to Problem

A blood vessel wall thickness estimation method according to one aspect of the present invention includes: obtaining behavioral information based on a video including a blood vessel wall obtained using four-dimensional angiography, the behavioral information being numerical information about changes over time in positions of a plurality of predetermined points in the blood vessel wall; generating estimation information for estimating a thickness of the blood vessel wall based on the behavioral information obtained in the obtaining; and outputting the estimation information generated in the generating, wherein the estimation information is information in which at least one of the following is visualized: a change in displacement over time; a change in speed over time; a change in acceleration over time; a change in kinetic energy over time; a spring constant obtained from the displacement and the acceleration, and a Fourier coefficient obtained from the change in the displacement over time.

A computer program according to one aspect of the present invention causes a computer to execute the above-described blood vessel wall thickness estimation method.

A blood vessel wall thickness estimation device according to one aspect of the present invention includes: an obtainer that obtains behavioral information based on a video including a blood vessel wall obtained using four-dimensional angiography, the behavioral information being numerical information about changes over time in positions of a plurality of predetermined points in the blood vessel wall; a generator that generates estimation information for estimating a thickness of the blood vessel wall based on the behavioral information obtained by the obtainer; and an outputter that outputs the estimation information generated by the generator, wherein the estimation information is information in which at least one of the following is visualized: a change in displacement over time; a change in speed over time; a change in acceleration over time; a change in kinetic energy over time; a spring constant obtained from the displacement and the acceleration, and a Fourier coefficient obtained from the change in the displacement over time.

A blood vessel wall thickness estimation system according to one aspect of the present invention includes: the blood vessel wall thickness estimation device described above; a video information processing device that obtains the video and generates the behavioral information; and a display that displays the estimation information output by the outputter.

Advantageous Effects of Invention

With the blood vessel wall thickness estimation method and the like according to the present invention, it is possible to generate highly accurate information about the blood vessel wall using a minimally invasive method, thereby providing useful information for applying specific measures for blood vessel diseases.

BRIEF DESCRIPTION OF DRAWINGS

FIG. 9C illustrates changes over time in x-, y-, and z-axis displacements of another example of points in a proximal section, a middle section, and a distal section according to Case 1.

FIG. 9E illustrates changes over time in x-, y-, and z-axis displacements of another example of points in a proximal section, a middle section, and a distal section according to Case 1.

FIG. 9F illustrates changes over time in x-, y-, and z-axis displacements of another example of points in a proximal section, a middle section, and a distal section according to Case 1.

FIG. 16A illustrates changes over time in acceleration in the z-axis direction of one example of a point of a distal section according to Case 1.

FIG. 17B illustrates changes over time in kinetic energy of another example of a point of a proximal section according to Case 1.

FIG. 21B illustrates acceleration and displacement from a predetermined origin in the x-axis direction of another example of a point of a distal section according to Case 1.

DESCRIPTION OF EMBODIMENTS

Hereinafter, embodiments will be described with reference to the drawings. Each of the following embodiments describes a general or specific example. The numerical values, shapes, materials, elements, the arrangement and connection of the elements, steps, the order of the steps etc., presented in the following embodiments are mere examples, and do not limit the scope of the present invention. Among elements in the following embodiments, those not recited in any one of the independent claims are described as optional elements.

Note that the figures are schematic drawings, and are not necessarily exact depictions. In the figures, elements having essentially the same configuration share like reference numbers. Accordingly, overlapping descriptions thereof are omitted or simplified.

Embodiment

[Configuration of Blood Vessel Wall Thickness Estimation System]

Figure 1:
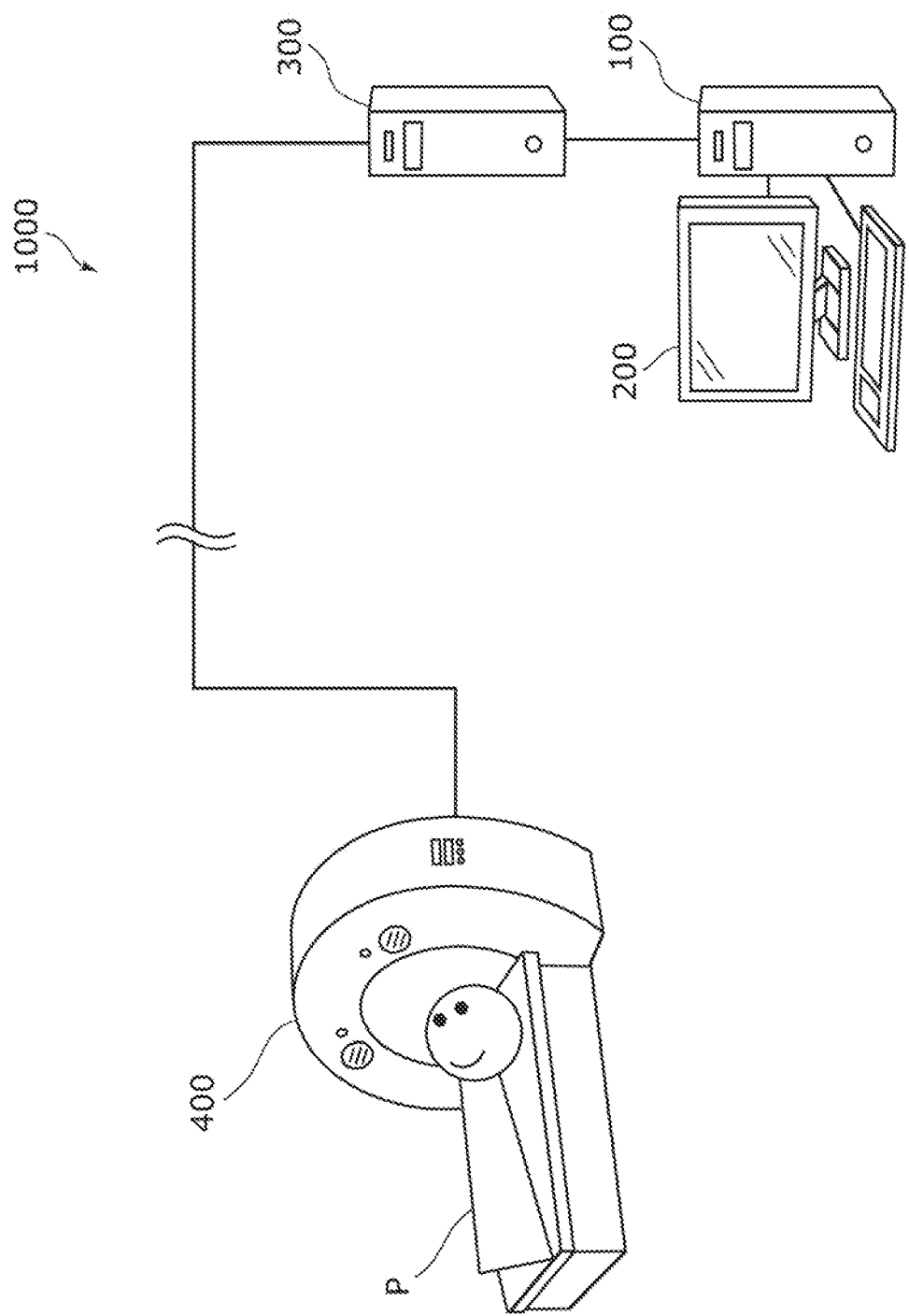
FIG. 1 is a diagram illustrating the configuration of a blood vessel wall thickness estimation system according to an embodiment of the present disclosure.

First, the configuration of blood vessel wall thickness estimation system 1000 according to the present embodiment will be described. FIG. 1 is a diagram illustrating the configuration of blood vessel wall thickness estimation system 1000 according to the present embodiment.

Blood vessel wall thickness estimation system 1000 is a system that uses four-dimensional angiography to obtain behavioral information, which is numerical information about changes over time in the position of a predetermined point, from a video including a blood vessel wall of subject P, and generates estimation information for estimating the thickness of the blood vessel wall based on the behavioral information. In one specific example, blood vessel wall thickness estimation system 1000 estimates the thickness of a cerebral aneurysm in subject P.

Four-dimensional angiography is a technique that adds a time axis to three-dimensional angiography. Three-dimensional angiography is a technique that collects three-dimensional data on blood vessels using X-ray CT or MRI, and extracts vascular information. Four-dimensional angiography using X-ray CT is also referred to as four-dimensional computed tomography angiography (4DCTA).

A video is obtained through four-dimensional angiography. The video is a time series of three or more still images, and may be, for example, a video obtained over n pulses of the heart (n is a natural number). For example, the video may be a video within a predetermined time period. For example, the predetermined time period may be m seconds (m is a natural number).

The thickness of the blood vessel wall may be the thickness of a wall of the blood vessel including arteries or veins, may be the thickness of the wall of an aneurysm or varicose vein, and may be the thickness of the wall of a cerebral aneurysm.

As illustrated in FIG. 1, blood vessel wall thickness estimation system 1000 includes blood vessel wall thickness estimation device 100, display 200, video information processing device 300, and video capturing device 400.

Video capturing device 400 is a device that generates a video including a blood vessel wall using four-dimensional angiography. Video capturing device 400 is, for example, a CT device or an MRI device. When video capturing device 400 is a CT device, the CT device includes an X-ray tube that irradiates X-rays, a detector that receives signals, and a computer. The detector is located opposite the X-ray tube and detects the X-rays after they have passed through the body of subject P. Using the fact that the absorption of X-rays differs depending on the part of the body of subject P, the computer generates a video including the blood vessel wall in a specific part of the body of subject P.

Unlike techniques such as craniotomy, the technique of using a CT or MRI device and four-dimensional angiography is a minimally invasive technique because it does not require an incision or the like that places a large burden on the body of subject P. Moreover, the technique of using a CT or MRI device and four-dimensional angiography can generate highly precise videos.

Video information processing device 300 obtains a video including a blood vessel wall generated by video capturing device 400 using four-dimensional angiography, and generates behavioral information, which is numerical information about changes over time in the positions of a plurality of predetermined points in the blood vessel wall. For example, the behavioral information is numerical information in which a plurality of pairs are arranged according to the passage of time in which the heart pulsates one time in the video, with one pair consisting of (i) a specific time in the video and (i) three-dimensional coordinate positions of a plurality of predetermined points in the blood vessel wall at that specific time. Video information processing device 300 outputs the behavioral information to blood vessel wall thickness estimation device 100. Video information processing device 300 is, for example, a personal computer, but may also be a server with high computing power that is connected to a network.

Blood vessel wall thickness estimation device 100 obtains the behavioral information generated by video information processing device 300, generates estimation information for estimating the thickness of the blood vessel wall based on the obtained behavioral information, and outputs the generated estimation information to display 200. Estimation information, which will be discussed in greater detail below with reference to FIG. 8A through FIG. 22B, is visualized information that is used to estimate the thickness of the blood vessel wall. The estimation information is, for example, image data. Blood vessel wall thickness estimation device 100 is, for example, a personal computer, but may also be a server with high computing power that is connected to a network.

Display 200 displays the estimation information output from blood vessel wall thickness estimation device 100. Specifically, display 200 is a monitor including, for example, a liquid crystal panel or organic electroluminescent (EL) panel. A television, smartphone, or tablet terminal may be used as display 200.

Blood vessel wall thickness estimation device 100, display 200, and video information processing device 300 may be connected by wire or wirelessly, so long as they can send and receive the behavioral information or the estimation information.

Video information processing device 300 obtains a video including a blood vessel wall, and generates behavioral information, which is numerical information about changes over time in the positions of a plurality of predetermined points in the blood vessel wall. Blood vessel wall thickness estimation device 100 obtains the behavioral information generated by video information processing device 300, and generates estimation information for estimating the thickness of the blood vessel wall based on the obtained behavioral information. Blood vessel wall thickness estimation device 100 further outputs the generated estimation information to display 200.

As a result, in blood vessel wall thickness estimation system 1000, a video including a blood vessel wall is obtained via a minimally invasive method. Furthermore, blood vessel wall thickness estimation system 1000 can generate estimation information for estimating the thickness of the blood vessel wall using the behavioral information related to the video. Therefore, blood vessel wall thickness estimation system 1000 can generate highly accurate information about the wall thickness in the vicinity of a plurality of predetermined points in the blood vessel wall.

Next, the functional configuration of blood vessel wall thickness estimation device 100 according to the present embodiment will be described in detail.

Figure 2:
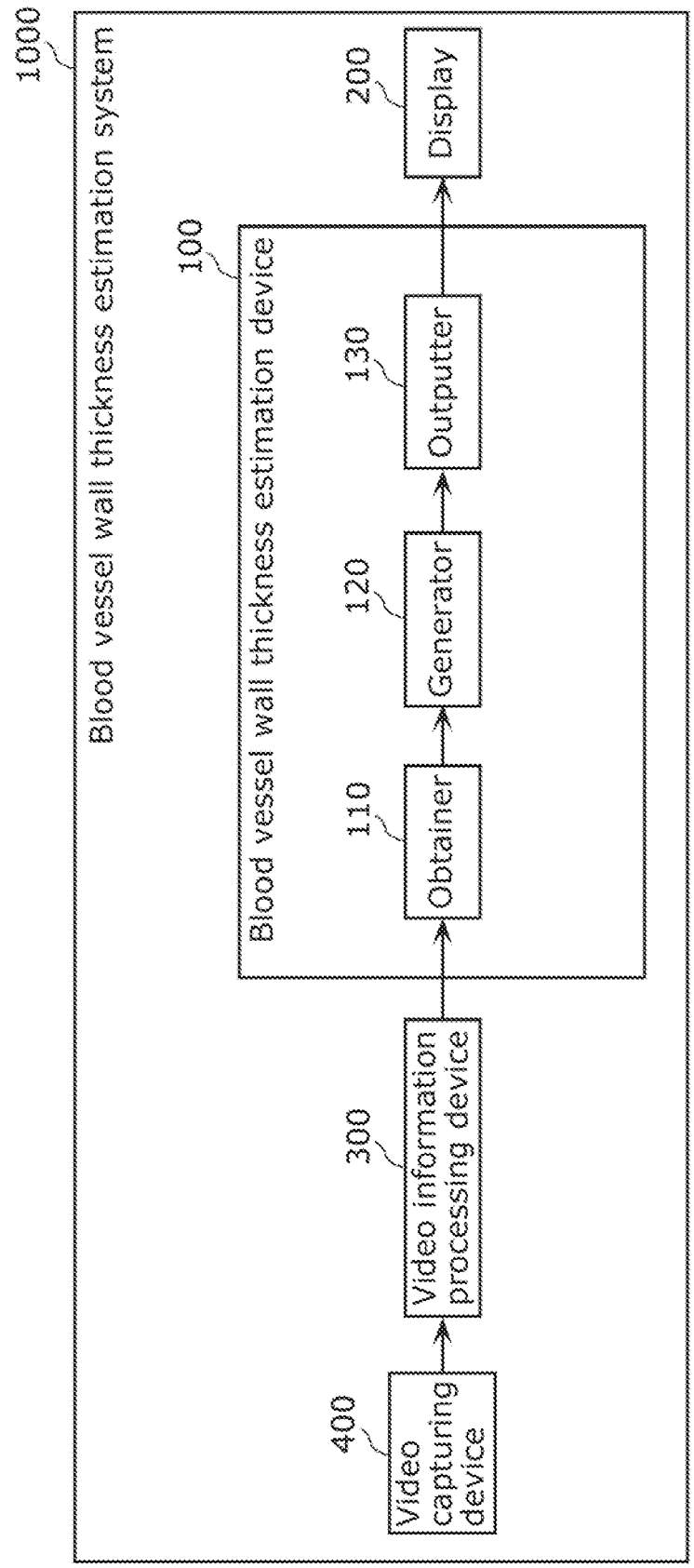
FIG. 2 is a block diagram illustrating the characterizing functional configuration of a blood vessel wall thickness estimation device according to an embodiment of the present disclosure.

FIG. 2 is a block diagram illustrating the characterizing functional configuration of blood vessel wall thickness estimation device 100 according to the present embodiment. Blood vessel wall thickness estimation device 100 includes obtainer 110, generator 120, and outputter 130.

Obtainer 110 obtains behavioral information, which is numerical information about changes over time in positions of a plurality of predetermined points in a blood vessel wall, based on a video including the blood vessel wall obtained using four-dimensional angiography. Specifically, obtainer 110 obtains behavioral information generated by video information processing device 300. Obtainer 110 is, for example, a communication interface for performing wired or wireless communication.

Generator 120 generates estimation information for estimating the thickness of the blood vessel wall based on the behavioral information obtained by obtainer 110. The estimation information is information in which at least one of the following is visualized: a change in displacement over time, a change in speed over time, a change in acceleration over time, a change in kinetic energy over time, a spring constant obtained from the displacement and the acceleration, and a Fourier coefficient obtained from the change in displacement over time. Moreover, the estimation information is information about a plurality of predetermined points. Stated differently, the estimation information is information used to estimate the thickness of the blood vessel wall in the vicinity of a plurality of predetermined points.

For example, the estimation information may be image data in which information based on at least one selected from the above is graphed. For example, when the estimation information is information that visualizes change in displacement over time, the estimation information is, for example, image data of a graph with time on the horizontal axis and displacement on the vertical axis. The method for generating the estimation information will be described below with reference to FIG. 8A through FIG. 22B. Generator 120 is, specifically, realized as a processor, a microcomputer, or a dedicated circuit that executes a program.

Outputter 130 outputs the estimation information generated by generator 120. Outputter 130 may output the estimation information generated by generator 120 to display 200. Outputter 130 is, for example, a communication interface for performing wired or wireless communication.

Next, the plurality of predetermined points in the blood vessel wall, which is one of information about the behavioral information, will be described with reference to FIG. 3A through FIG. 6. In the present embodiment, the blood vessel wall is aneurysm wall 11 of cerebral aneurysm 10. In FIG. 3A through FIG. 22B, the x-axis positive direction is the direction in which cerebral aneurysm 10 extends from parent blood vessel 20, the z-axis is the direction in which parent blood vessel 20 extends, and the y-axis is the direction extending orthogonally to the x- and z-axes.

Figure 3A:
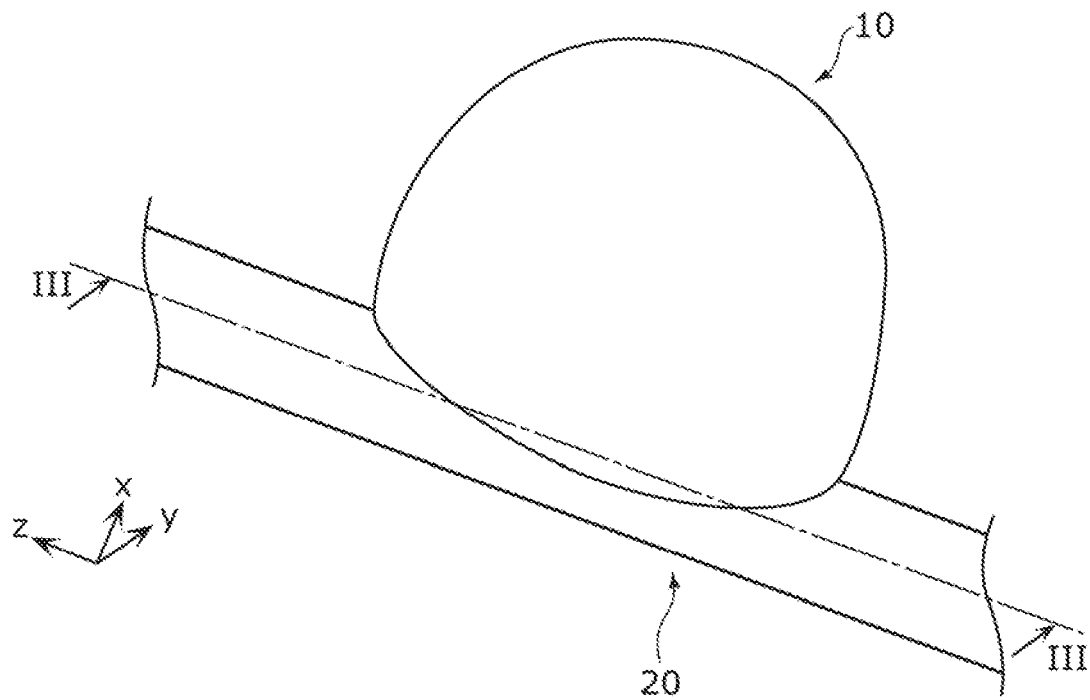
FIG. 3A is a perspective view of a cerebral aneurysm according to an embodiment of the present disclosure.
Figure 3B:
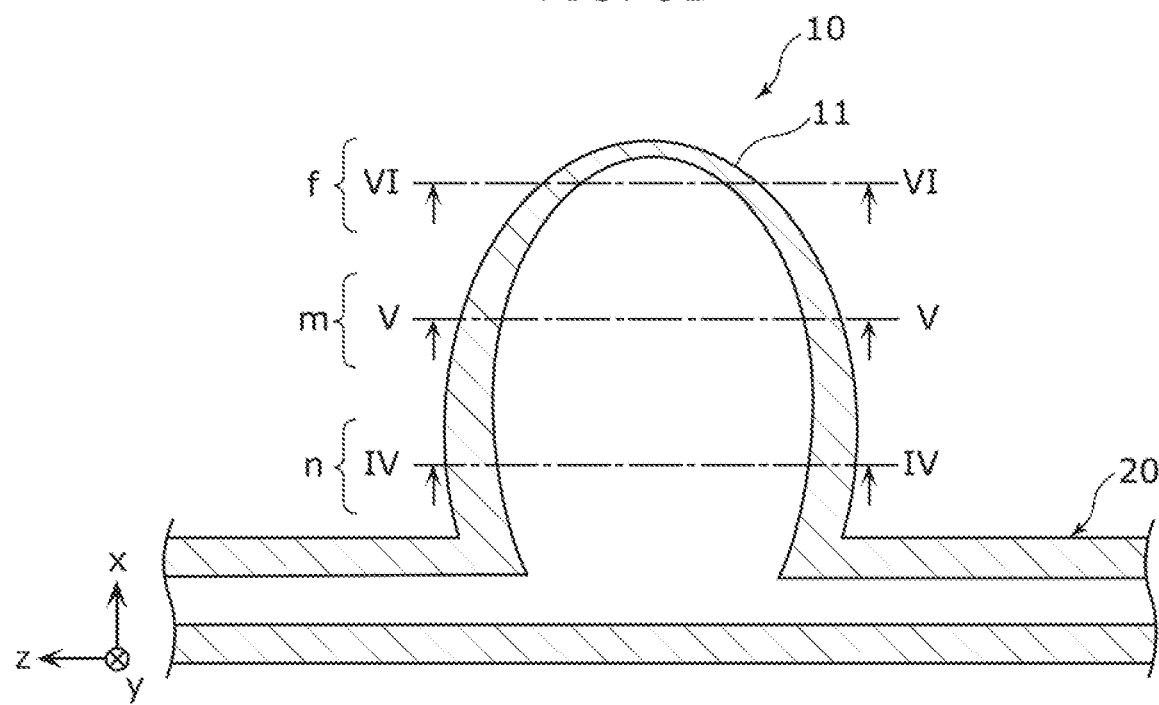
FIG. 3B is a cross sectional view of the cerebral aneurysm according to an embodiment of the present disclosure taken at line III-III in FIG. 3A.

FIG. 3A is a perspective view of cerebral aneurysm 10 according to the present embodiment. FIG. 3B is a cross sectional view of cerebral aneurysm 10 according to the present embodiment taken at line III-III in FIG. 3A. Parent blood vessel 20 is one blood vessel among the arteries in the brain of subject P. Cerebral aneurysm 10 is an aneurysm in which a portion of parent blood vessel 20 has bulged, extending in the x-axis direction from parent blood vessel 20.

As illustrated in FIG. 3B, in cerebral aneurysm 10, the region close to parent blood vessel 20 is defined as proximal section n, the region far from parent blood vessel 20 is defined as distal section f, and the region between proximal section n and distal section f is defined as middle section m.

Figure 4:
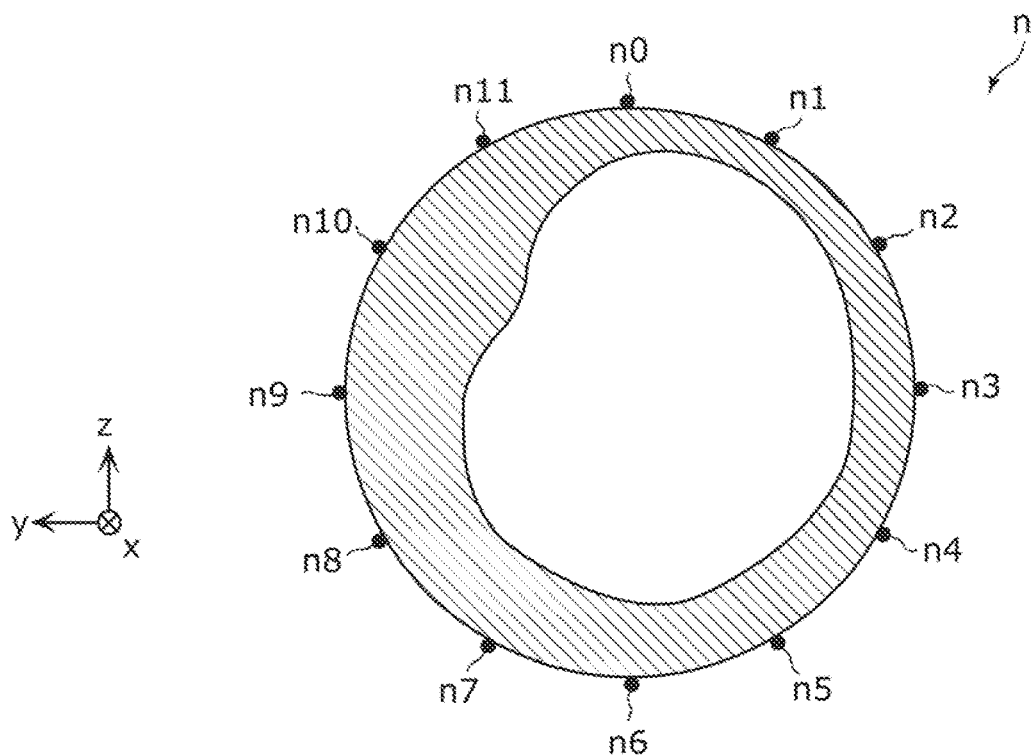
FIG. 4 is a cross sectional view of a proximal section of a cerebral aneurysm according to an embodiment of the present disclosure taken at line IV-IV in FIG. 3B.
Figure 5:
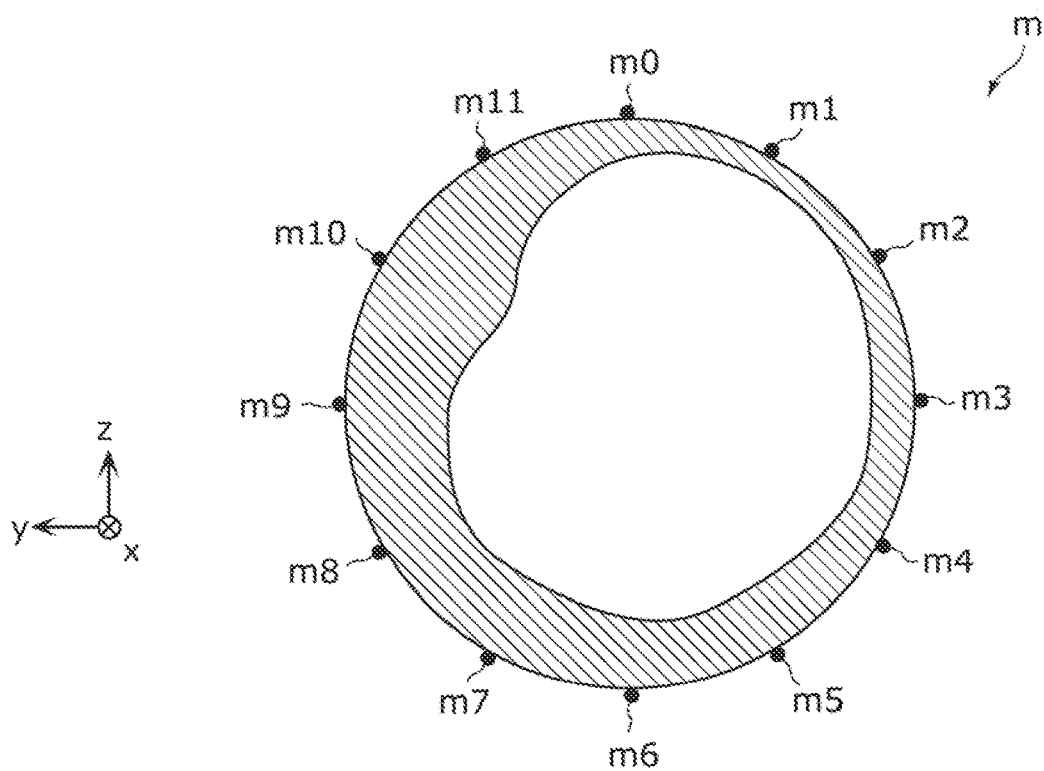
FIG. 5 is a cross sectional view of a middle section of a cerebral aneurysm according an embodiment of the present disclosure taken at line V-V in FIG. 3B.
Figure 6:
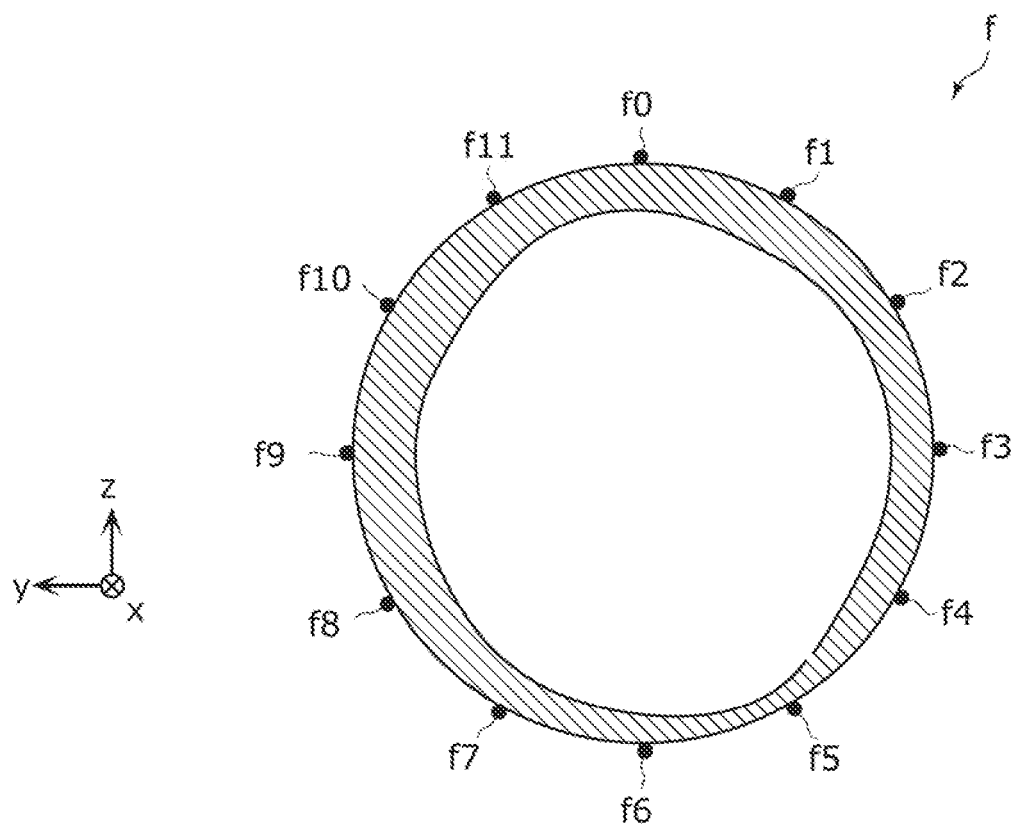
FIG. 6 is a cross sectional view of a distal section of a cerebral aneurysm according to an embodiment of the present disclosure taken at line VI-VI in FIG. 3B.

FIG. 4 is a cross sectional view of proximal section n of cerebral aneurysm 10 according to the present embodiment taken at line IV-IV in FIG. 3B. FIG. 5 is a cross sectional view of middle section m of cerebral aneurysm 10 according to the present embodiment taken at line V-V in FIG. 3B. FIG. 6 is a cross sectional view of distal section f of cerebral aneurysm 10 according to the present embodiment taken at line VI-VI in FIG. 3B. FIG. 4 through FIG. 6 are all cross sectional views taken in a yz plane.

As FIG. 4 illustrates, in the cross section of proximal section n, points are provided in the 0 o'clock to 11 o'clock directions, so as to correspond to the hours of a clock face. In other words, point n0 is provided in the 0 o'clock direction, and points n1 to n11 are provided in the 1 o'clock to 11 o'clock directions, respectively. As FIG. 5 and FIG. 6 illustrate, points are also provided in the 0 o'clock to 11 o'clock directions in the cross sections of middle section m and distal section f. In the middle section m, points m0 to m11 are provided in the 0 o'clock to 11 o'clock directions, respectively, and in distal section f, points f0 to f11 are provided in the 0 o'clock to 11 o'clock directions, respectively. The plurality of predetermined points in the blood vessel wall according to the present embodiment are, for example, points n0 to n11, points m0 to m11, and points f0 to f11. Stated differently, since there are 12 predetermined points in each of proximal section n, middle section m, and distal section f, there are a total of 36 predetermined points in the blood vessel wall. Hereinafter, points n0 to n11, points m0 to m11, and points f0 to f11 may be collectively referred to as the points in the 0 o'clock to 11 o'clock directions.

At each of these 36 predetermined points, obtainer 110 obtains behavioral information, which is numerical information about changes in position over time. Based on this behavioral information, generator 120 generates estimation information for estimating the thickness of aneurysm wall 11 in the vicinity of a predetermined point. The plurality of predetermined points in the blood vessel wall are not limited to the above examples, and can be selected from two or more points in the blood vessel wall.

In the present embodiment, the behavioral information is numerical information about changes in position over time during a certain period of time. A certain period of time is, for example, the duration of one pulsation of the heart. Furthermore, the duration of one pulsation of the heart is divided evenly into 83 steps. Here, the point in time when the pulsation starts is step 0 and the point in time when the pulsation ends is step 83. Accordingly, the behavioral information includes information about the x-, y-, and z-axis positions of the 36 predetermined points at each of the 0 to 83 steps.

The certain period of time may be a specific number of seconds, for example, 1 second, 5 seconds, or 10 seconds. The certain period of time may be subdivided in any manner as long as it is three or more divisions. For example, unlike the above, the certain period of time may be divided by a number of steps other than 83. Furthermore, the certain period of time need not be divided evenly.

[Steps of Process in Blood Vessel Wall Thickness Estimation Method]

Figure 7:
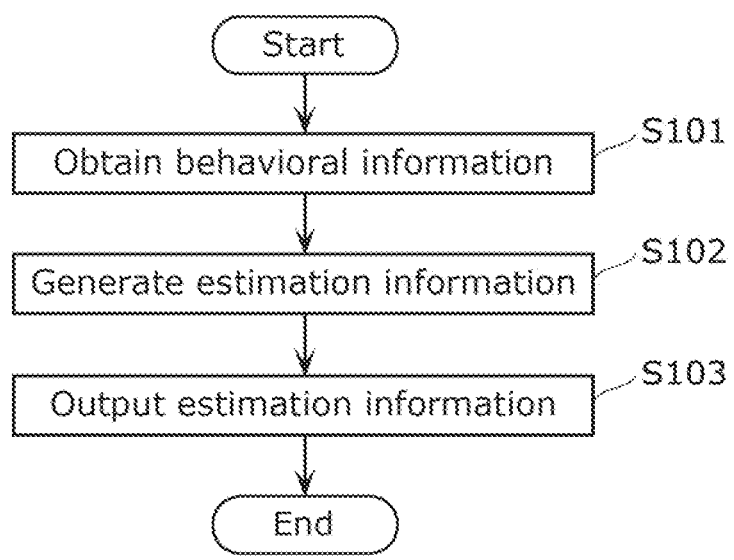
FIG. 7 is a flowchart illustrating steps of a process in which a blood vessel wall thickness estimation device according to an embodiment of the present disclosure estimates the thickness of a wall of a cerebral aneurysm.

Next, specific steps of a process in the blood vessel wall thickness estimation method performed by blood vessel wall thickness estimation device 100 will be described. FIG. 7 is a flowchart illustrating steps of a process in which blood vessel wall thickness estimation device 100 according to the present embodiment estimates the thickness of aneurysm wall 11 of cerebral aneurysm 10.

Obtainer 110 obtains behavioral information via video information processing device 300. The behavioral information is numerical information about changes over time in the positions of a plurality of predetermined points in aneurysm wall 11 of cerebral aneurysm 10 of subject P (obtaining step S101).

Next, generator 120 generates estimation information for estimating the thickness of the blood vessel wall from the behavioral information obtained by obtainer 110 in obtaining step S101 (generating step S102). The estimation information may be, for example, image data of a graph.

Next, outputter 130 outputs the estimation information generated by generator 120 (outputting step S103). In outputting step S103, outputter 130 transmits, for example, the image data of a graph generated by generator 120 in generating step S102 to display 200.

Display 200 obtains the image data output by outputter 130 and displays an image based on the image data.

Blood vessel wall thickness estimation device 100 may execute the blood vessel wall thickness estimation method by reading a computer program recorded on a computer-readable recording medium such as a CD-ROM.

Next, a detailed example of the estimation information will be given. Examples of the estimation information include a change in displacement over time, a change in speed over time, a change in acceleration over time, a change in kinetic energy over time, a spring constant obtained from the displacement and the acceleration, and a Fourier coefficient obtained from the change in displacement over time. Moreover, the estimation information will be described using Cases 1, 2 and 3, which are examples of disease symptoms, as examples according to the present embodiment. Cases 1, 2, and 3 all relate to cerebral aneurysms, and pertain to mutually different subjects P.

Case 1 will be used to explain a case in which the estimation information is a change in displacement over time, a change in speed over time, a change in acceleration over time, a change in kinetic energy over time, and a spring constant obtained from the displacement and the acceleration, and Cases 2 and 3 will be used to explain a case in which the estimation information is a Fourier coefficient obtained from the change in displacement over time.

Estimation Information Examples

First, an example in which the estimation information is a change in displacement over time will be given.

Figure 8A:
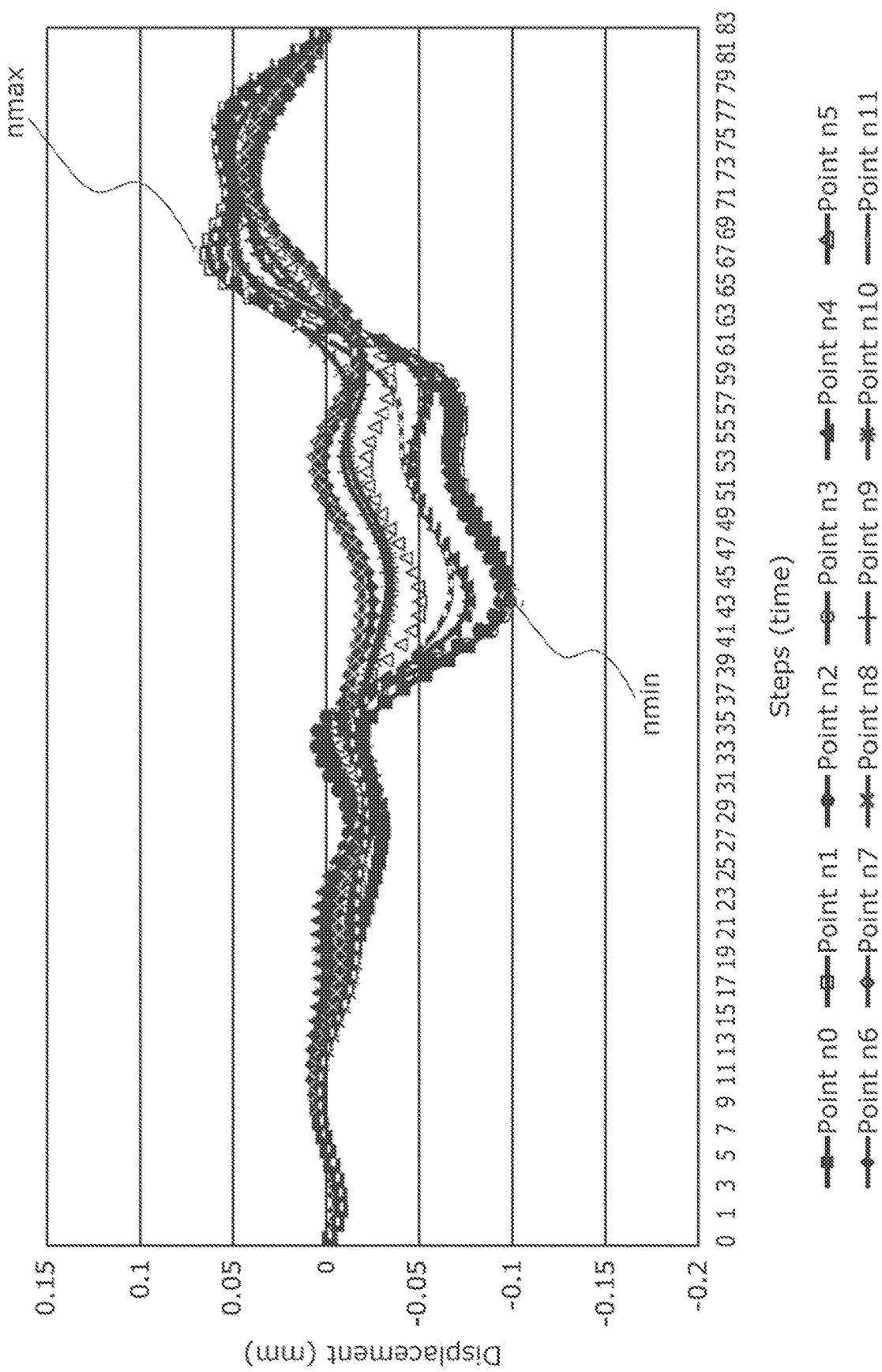
FIG. 8A illustrates changes over time in z-axis displacement of points of a proximal section according to Case 1.
Figure 8B:
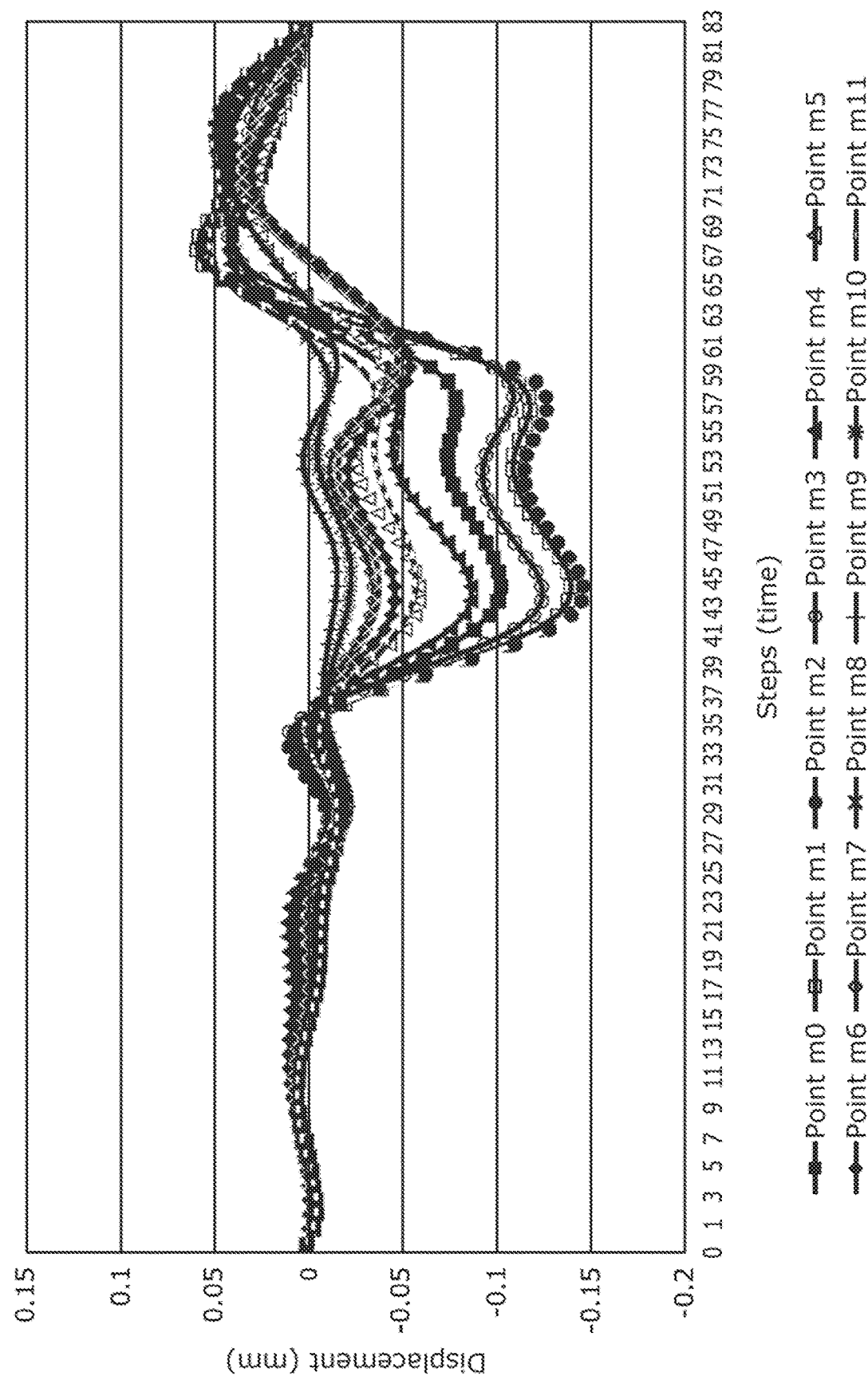
FIG. 8B illustrates changes over time in z-axis displacement of points of a middle section according to Case 1.
Figure 8C:
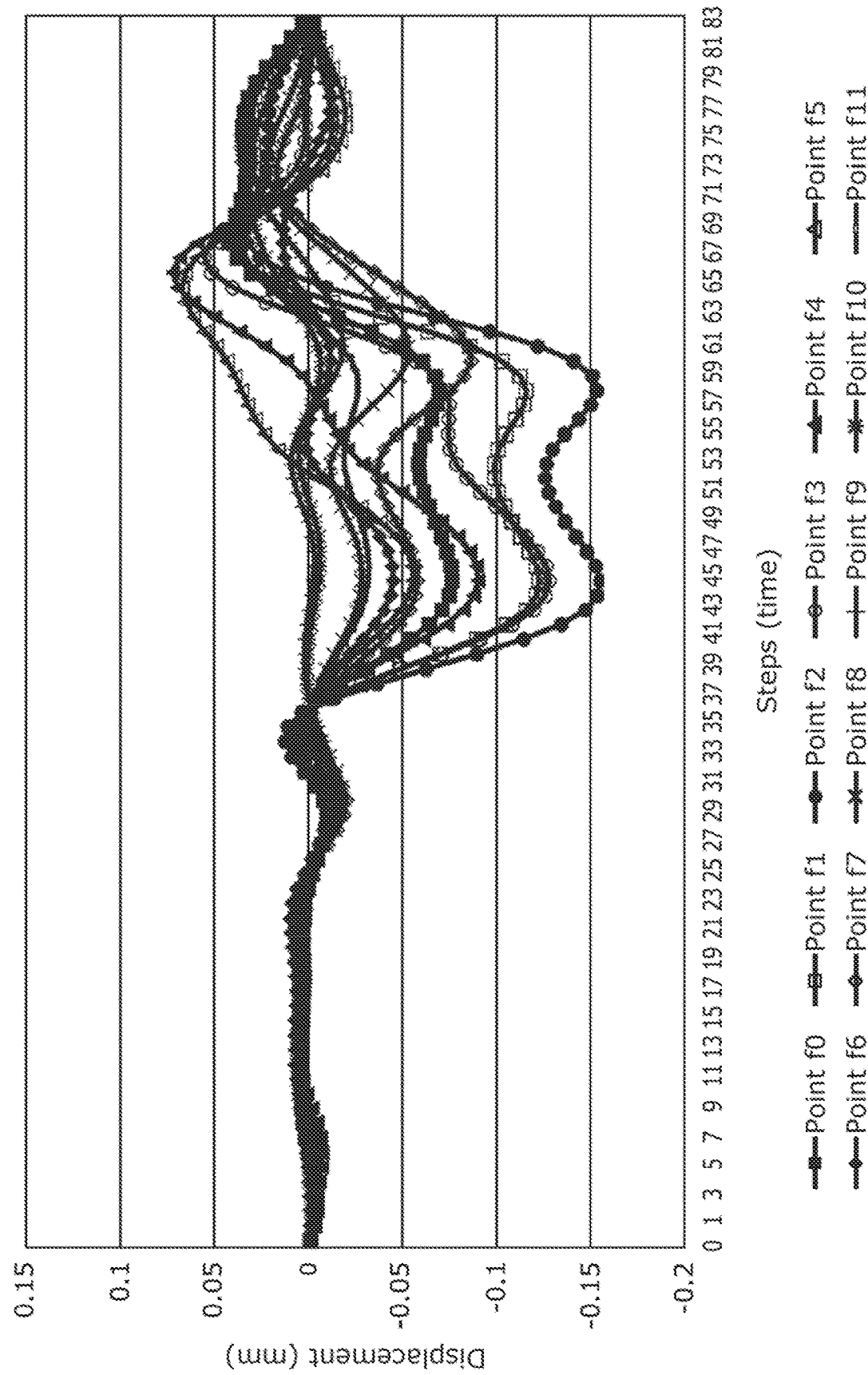
FIG. 8C illustrates changes over time in z-axis displacement of points of a distal section according to Case 1.

FIG. 8A illustrates changes over time in z-axis displacement of points n0 to n11 of proximal section n according to Case 1. FIG. 8B illustrates changes over time in z-axis displacement of points m0 to m11 of middle section m according to Case 1. FIG. 8C illustrates changes over time in z-axis displacement of points f0 to f11 of distal section f according to Case 1.

In FIG. 8A through FIG. 8C, the steps, which are units of time, are represented on the horizontal axis, and z-axis displacement is represented on the vertical axis. The z-axis displacement is a value of parallel shift of the z-axis position at each step such that the z-axis position at step 0 is 0 (origin). In FIG. 9A through FIG. 22B to be described later as well, the corresponding axis displacement is a value of parallel shift of the corresponding axis position at each step such that the corresponding axis position at step 0 is 0 (origin).

When the estimation information is a change in displacement over time, the thickness of aneurysm wall 11 may be estimated using an indicator such as a difference between maximum and minimum values of the displacement, or variation of the displacement.

As FIG. 8A through FIG. 8C illustrate, the difference between the maximum and minimum values of displacement, which is one indicator, increases from proximal section n toward distal section f, i.e., increases with increasing distance from parent blood vessel 20. The maximum or minimum value of displacement is, for example, the maximum or minimum value among the displacements for points n0 through n11 at all of steps 0 to 83. For example, as FIG. 8A illustrates, the maximum value of displacement for proximal section n is maximum value nmax, and the minimum value of displacement for proximal section n is minimum value nmin.

The larger the difference between the maximum and minimum values of displacement in one pulsation is, the thinner aneurysm wall 11 corresponding to the points in the 0 o'clock to 11 o'clock directions is estimated to be since a significant displacement from the origin by the points in the 0 o'clock to 11 o'clock directions correlates to the stretching of aneurysm wall 11 by the pulsation. Therefore, it is estimated that aneurysm wall 11 becomes thinner from proximal section n toward distal section f since the difference between the maximum and minimum values of displacement increases from proximal section n toward distal section f.

Variation of the displacement may be used as an indicator. As FIG. 8A through FIG. 8C illustrate, the variation of the displacement, which is one indicator, increases from proximal section n toward distal section f, i.e., increases with increasing distance from parent blood vessel 20.

The larger the variation of displacement in one pulsation is in one region, such as in proximal section n, middle section m, or distal section f, the thinner aneurysm wall 11 is estimated to be since there are a large number of points indicating mutual different movements among the points in the 0 o'clock to 11 o'clock directions, which correlates to the stretching of aneurysm wall 11 by the pulsation. In other words, it is estimated that aneurysm wall 11 becomes thinner from proximal section n toward distal section f.

The variation of the above values is expressed by standard deviation and may be calculated as follows. For example, in FIG. 8A, let p be the mean value of a total of 12 values, namely points n0 to n11 at any step, and variance $\sigma^2$ is obtained for the 12 numerical values at any step. The square root a of this variance $\sigma^2$ is the standard deviation. The same process is performed at each step (each of the steps 0 to 83 in the present embodiment) to calculate the standard deviation at each step and obtain the total standard deviation for all steps. The same process is further performed in FIG. 8B and FIG. 8C, and when the respective total values are compared, the higher the total value, the greater the variation, i.e., the thinner aneurysm wall 11 is estimated to be in the present embodiment.

Note that so long as the variation is an indicator based on statistics, something other than standard deviation may be used.

In FIG. 8A to FIG. 8C, the z-axis is used as one example, but when the estimation information is a change in displacement over time, the tendency for aneurysm wall 11 to become thinner from proximal section n toward distal section f in the z-axis can also be seen in the x- and y-axes as well.

Next, another example in which the estimation information is a change in displacement over time will be given.

Figure 9A:
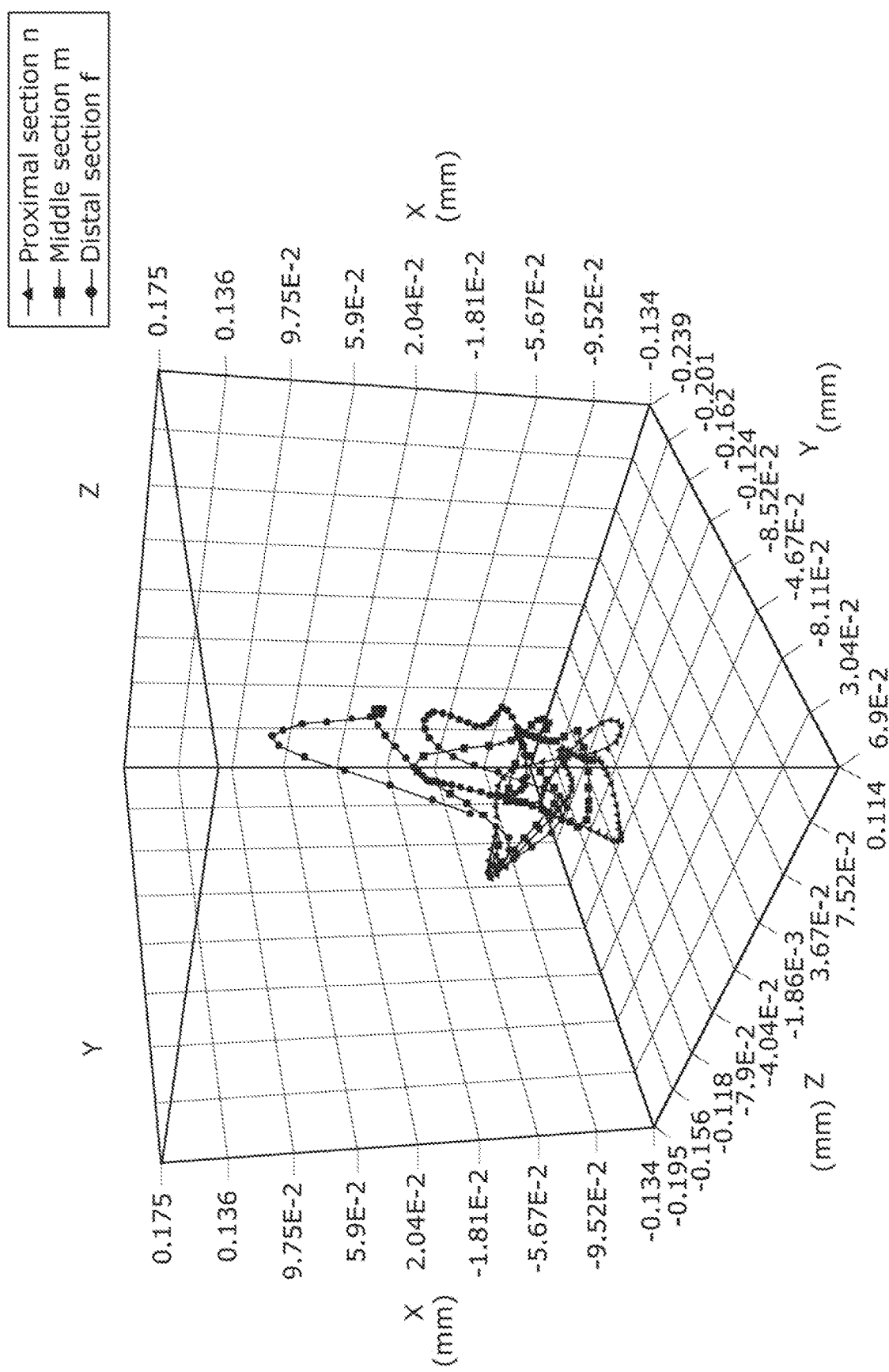
FIG. 9A illustrates changes over time in x-, y-, and z-axis displacements of one example of points in a proximal section, a middle section, and a distal section according to Case 1.
Figure 9B:
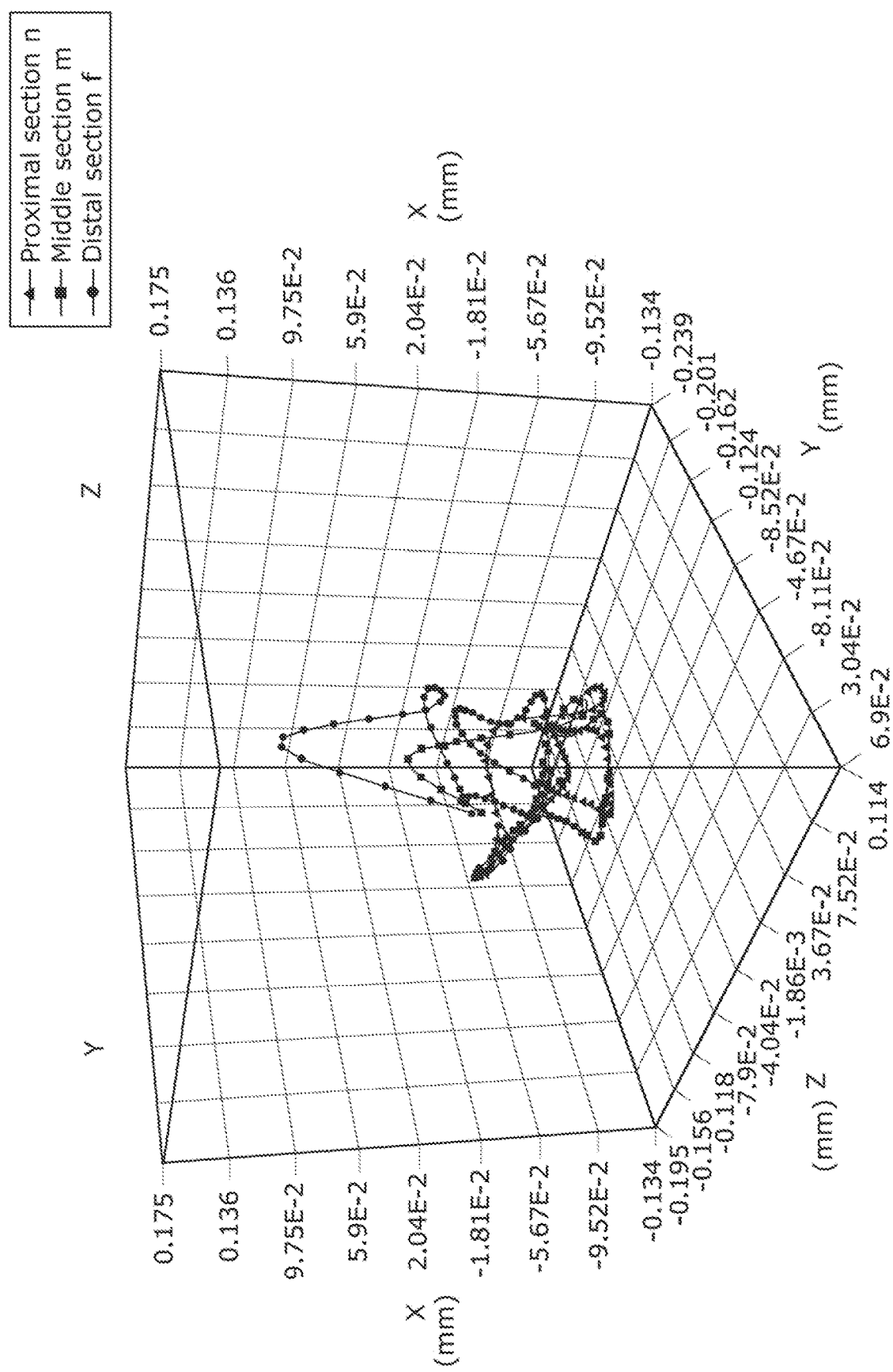
FIG. 9B illustrates changes over time in x-, y-, and z-axis displacements of another example of points in a proximal section, a middle section, and a distal section according to Case 1.
Figure 9D:
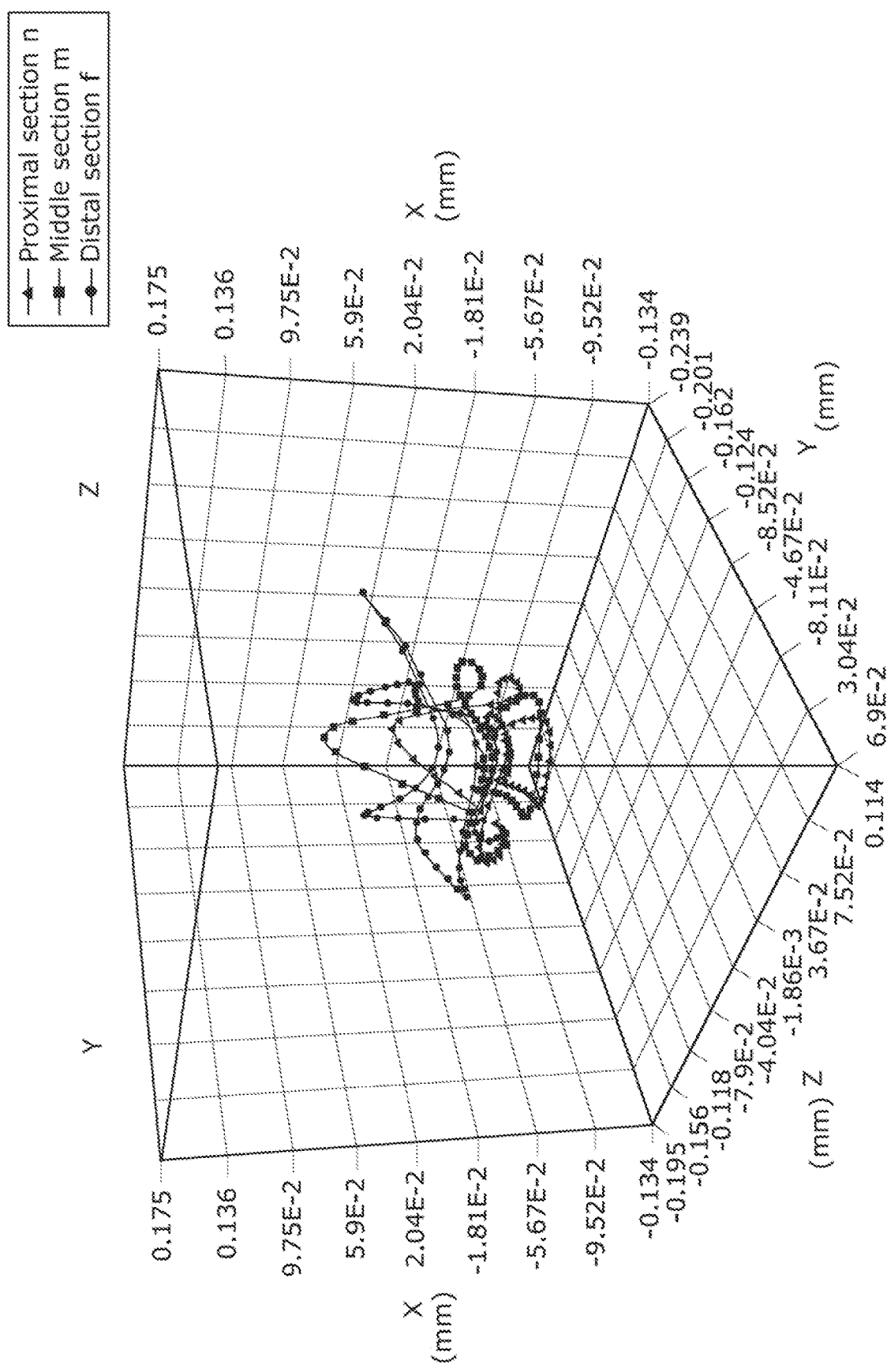
FIG. 9D illustrates changes over time in x-, y-, and z-axis displacements of another example of points in a proximal section, a middle section, and a distal section according to Case 1.
Figure 9G:
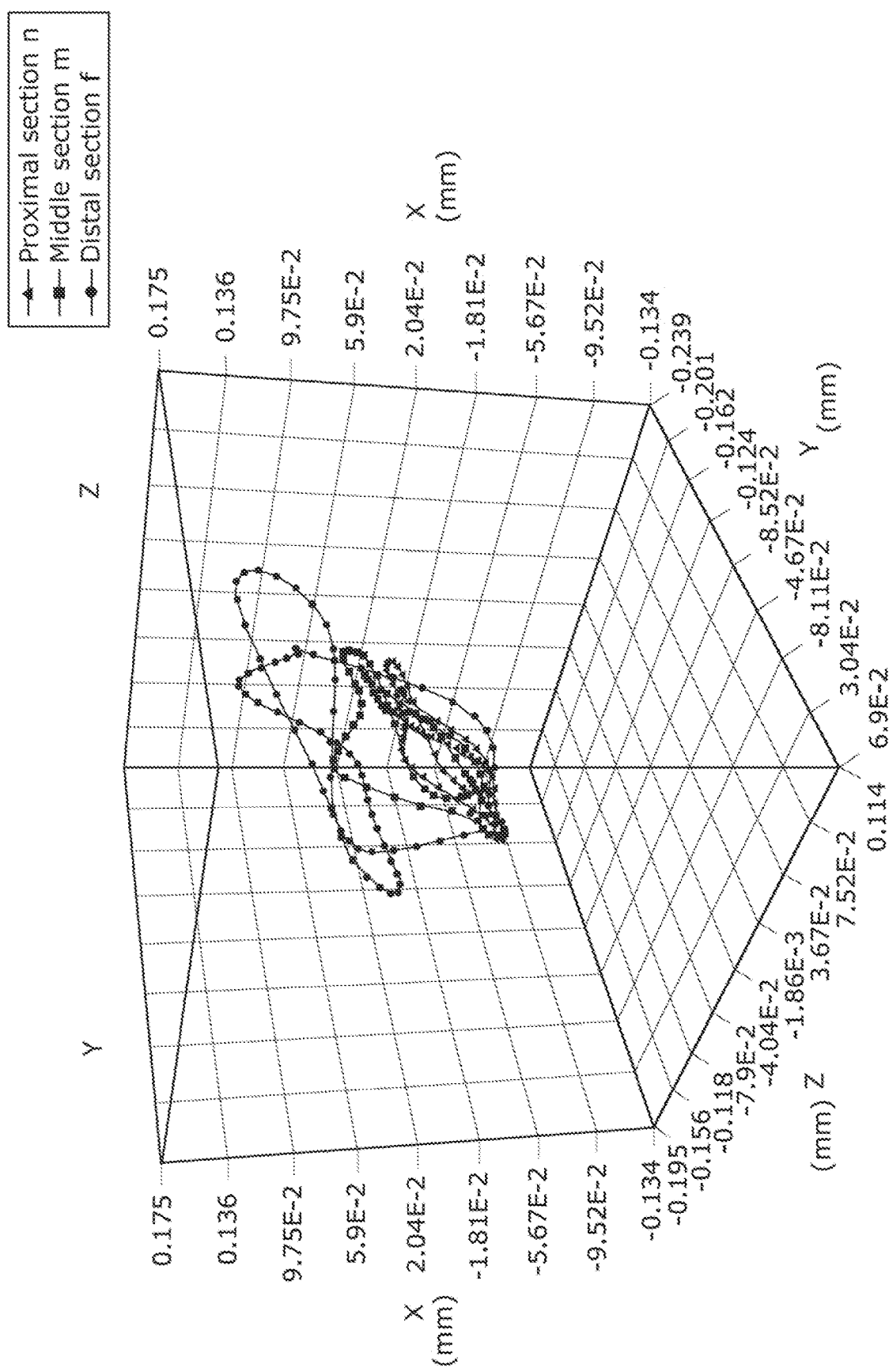
FIG. 9G illustrates changes over time in x-, y-, and z-axis displacements of another example of points in a proximal section, a middle section, and a distal section according to Case 1.
Figure 9H:
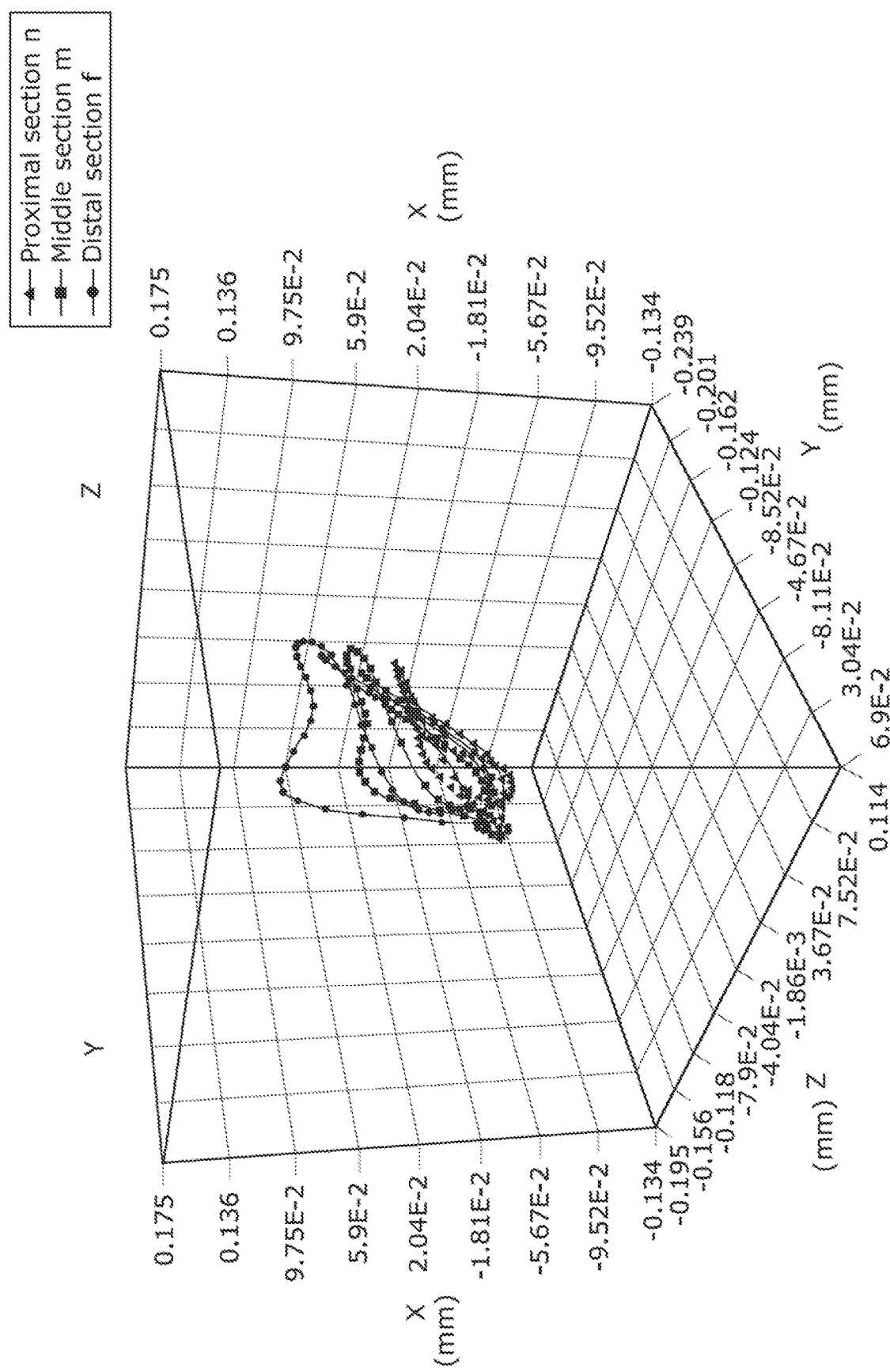
FIG. 9H illustrates changes over time in x-, y-, and z-axis displacements of another example of points in a proximal section, a middle section, and a distal section according to Case 1.
Figure 9I:
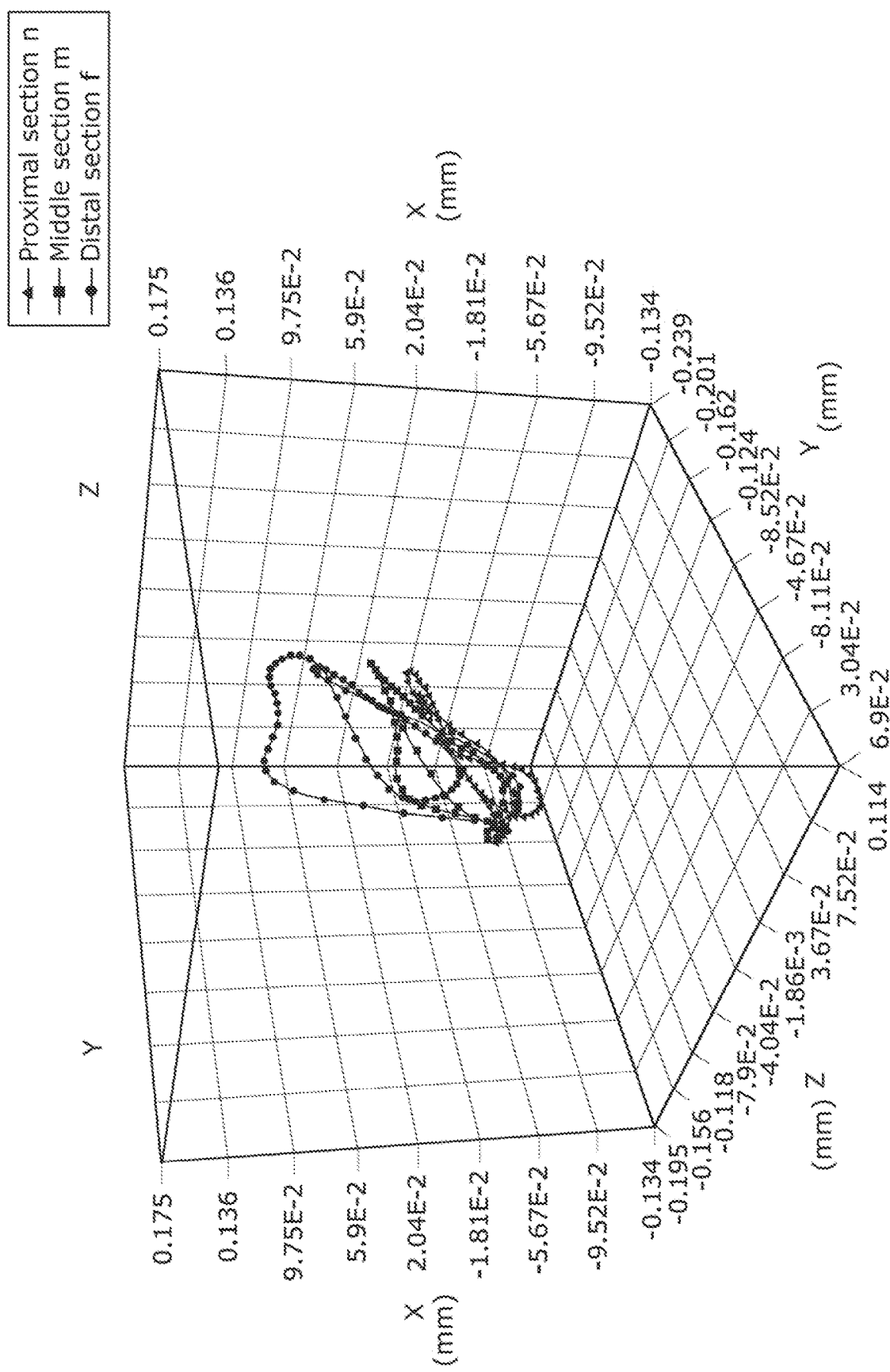
FIG. 9I illustrates changes over time in x-, y-, and z-axis displacements of another example of points in a proximal section, a middle section, and a distal section according to Case 1.
Figure 9J:
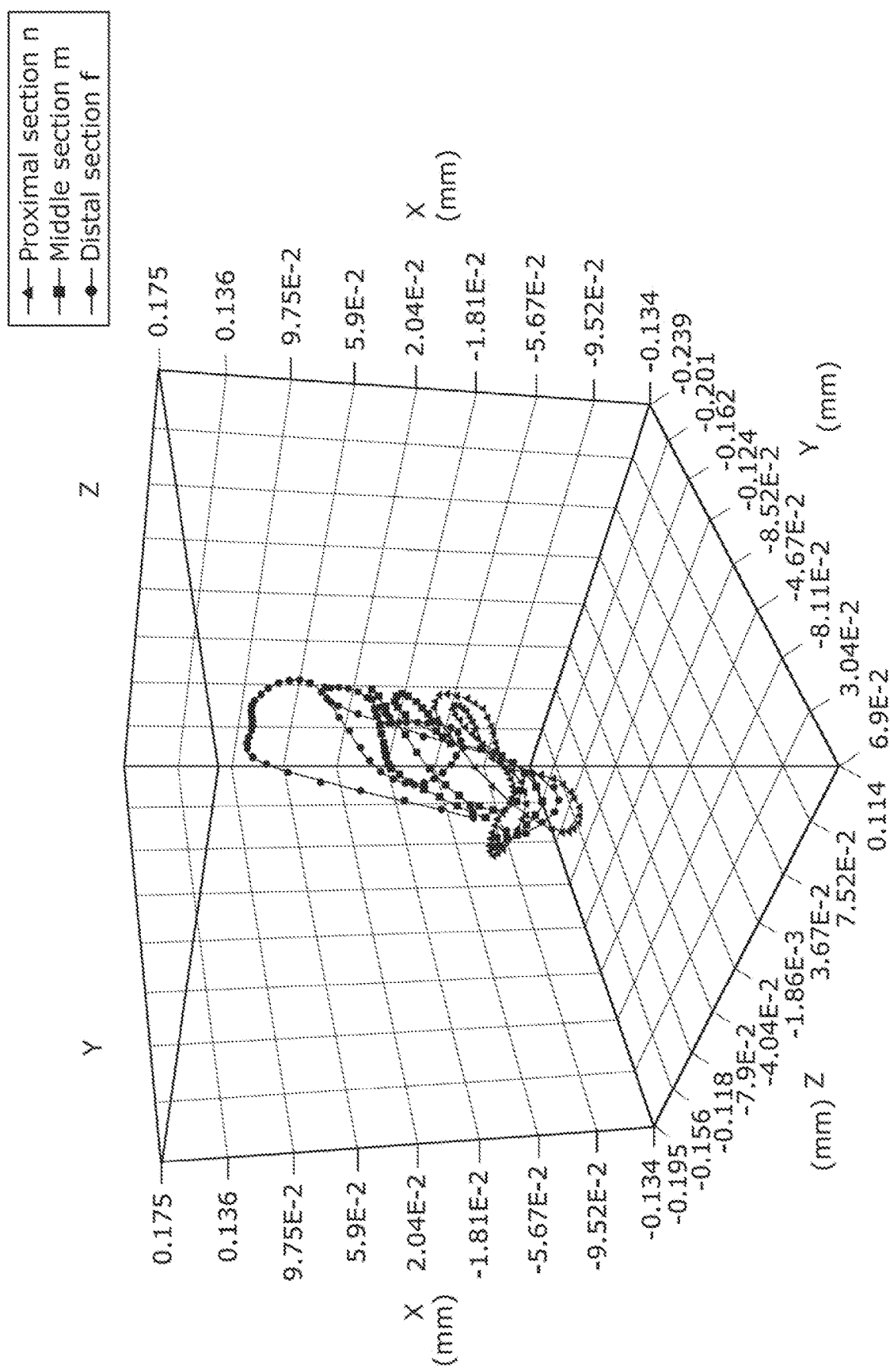
FIG. 9J illustrates changes over time in x-, y-, and z-axis displacements of another example of points in a proximal section, a middle section, and a distal section according to Case 1.
Figure 9K:
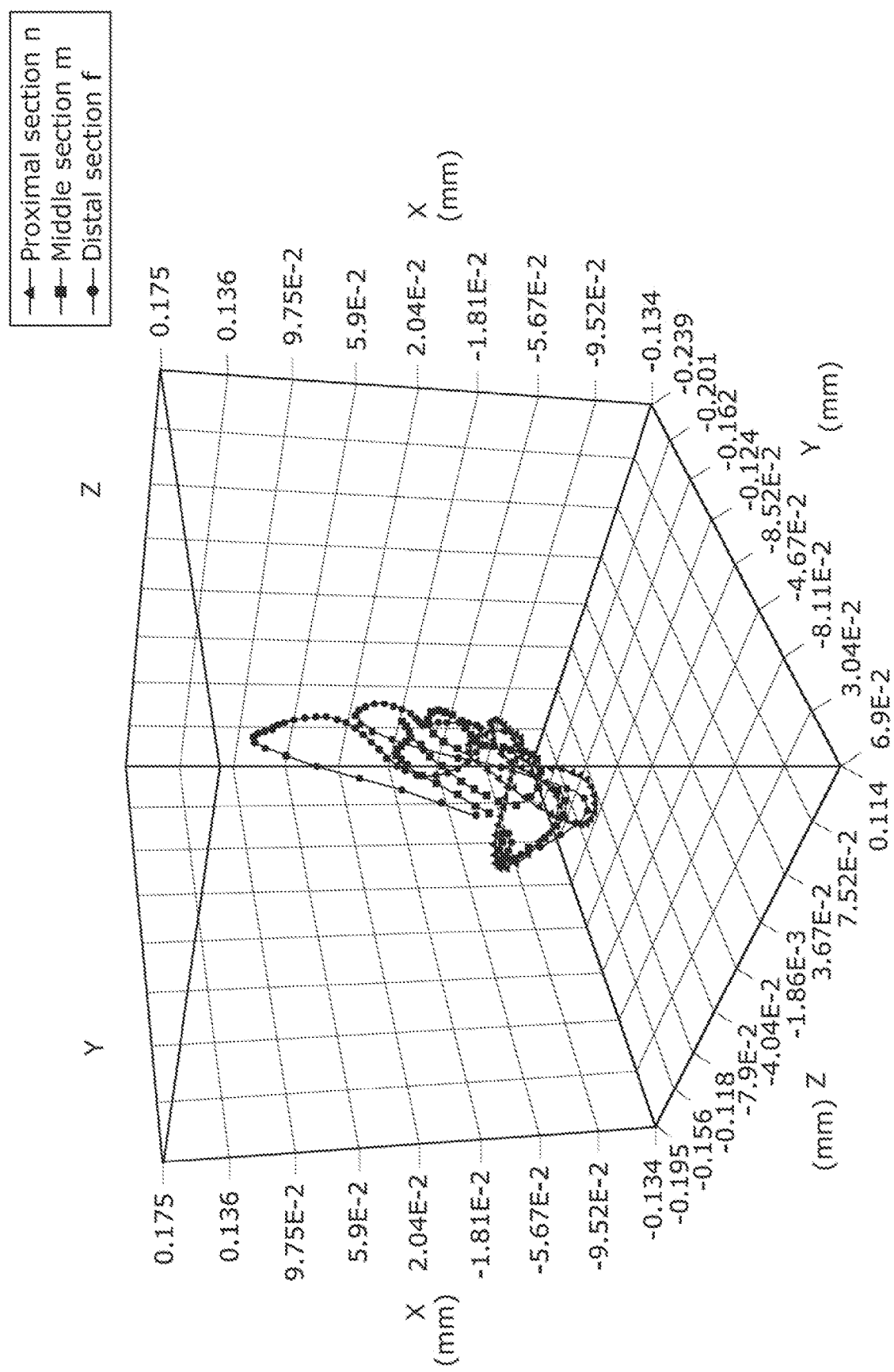
FIG. 9K illustrates changes over time in x-, y-, and z-axis displacements of another example of points in a proximal section, a middle section, and a distal section according to Case 1.
Figure 9L:
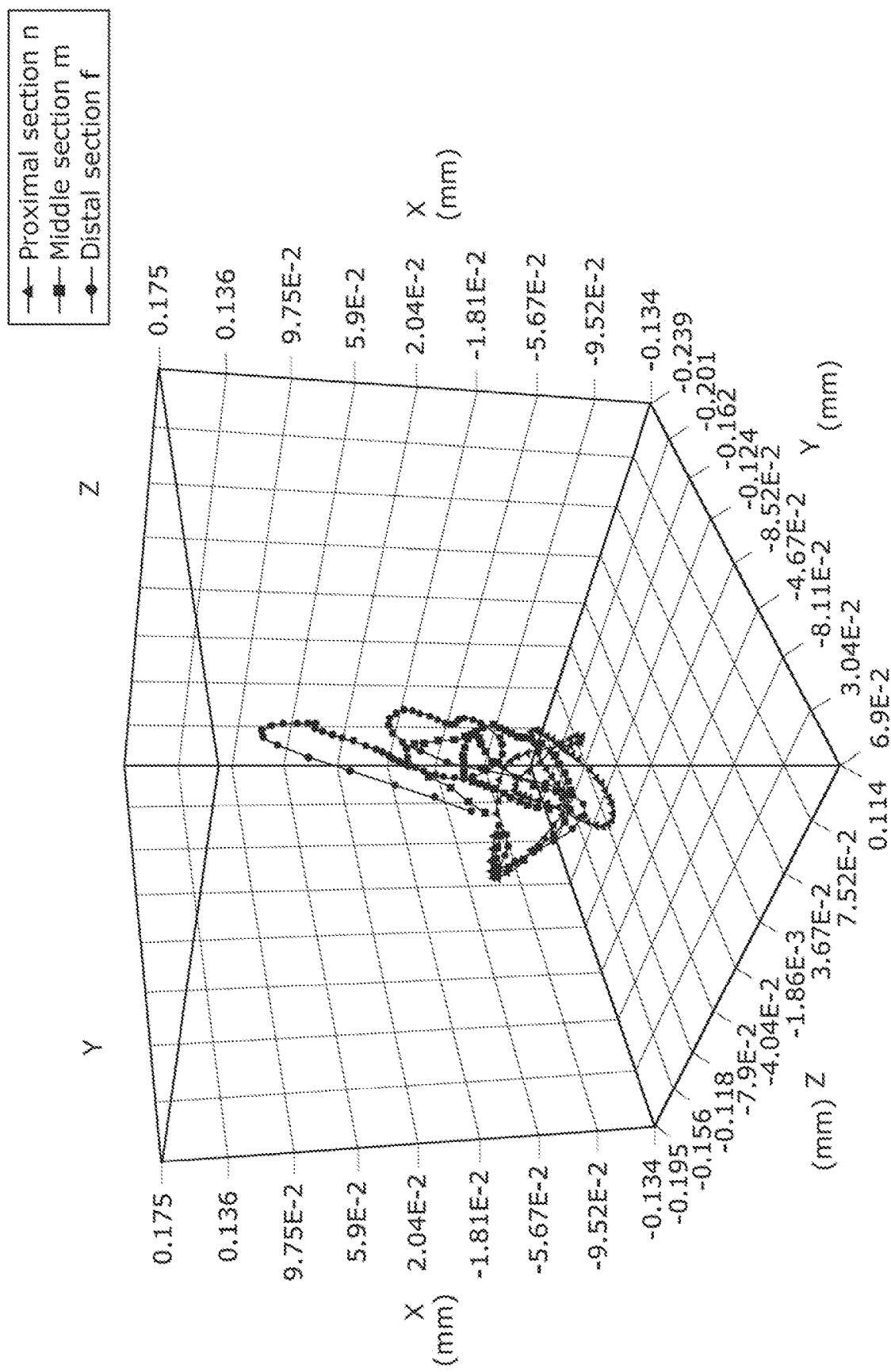
FIG. 9L illustrates changes over time in x-, y-, and z-axis displacements of another example of points in a proximal section, a middle section, and a distal section according to Case 1.

FIG. 9A illustrates changes over time in x-, y-, and z-axis displacements of point n0, point m0, and point f0 in proximal section n, middle section m, and distal section f, respectively, according to Case 1. FIG. 9B illustrates changes over time in x-, y-, and z-axis displacements of point n1, point m1, and point f1 in proximal section n, middle section m, and distal section f, respectively, according to Case 1. FIG. 9C illustrates changes over time in x-, y-, and z-axis displacements of point n2, point m2, and point f2 in proximal section n, middle section m, and distal section f, respectively, according to Case 1. FIG. 9D illustrates changes over time in x-, y-, and z-axis displacements of point n3, point m3, and point f3 in proximal section n, middle section m, and distal section f, respectively, according to Case 1. FIG. 9E illustrates changes over time in x-, y-, and z-axis displacements of point n4, point m4, and point f4 in proximal section n, middle section m, and distal section f, respectively, according to Case 1. FIG. 9F illustrates changes over time in x-, y-, and z-axis displacements of point n5, point m5, and point f5 in proximal section n, middle section m, and distal section f, respectively, according to Case 1. FIG. 9G illustrates changes over time in x-, y-, and z-axis displacements of point n6, point m6, and point f6 in proximal section n, middle section m, and distal section f, respectively, according to Case 1. FIG. 9H illustrates changes over time in x-, y-, and z-axis displacements of point n7, point m7, and point f7 in proximal section n, middle section m, and distal section f, respectively, according to Case 1. FIG. 9I illustrates changes over time in x-, y-, and z-axis displacements of point n8, point m8, and point f8 in proximal section n, middle section m, and distal section f, respectively, according to Case 1. FIG. 9J illustrates changes over time in x-, y-, and z-axis displacements of point n9, point m9, and point f9 in proximal section n, middle section m, and distal section f, respectively, according to Case 1. FIG. 9K illustrates changes over time in x-, y-, and z-axis displacements of point n10, point m10, and point f10 in proximal section n, middle section m, and distal section f, respectively, according to Case 1. FIG. 9L illustrates changes over time in x-, y-, and z-axis displacements of point n11, point m11, and point f11 in proximal section n, middle section m, and distal section f, respectively, according to Case 1.

In FIG. 9A through FIG. 9L, the axes represent x-, y-, and z-axis displacement, respectively. As FIG. 9A through FIG. 9L illustrate, displacement observed in proximal section n and middle section m does not change significantly for points n0 to n11 and points m0 to m11, respectively. However, as FIG. 9F illustrates, displacement observed in distal section f changes significantly particularly for point f5. More specifically, at point f5, the difference between the maximum and minimum values of displacement, which is one of the indicators, increases. Therefore, the curve drawn by point f5 in FIG. 9F is greatly spread out in space. Stated differently, it is estimated that the thickness of aneurysm wall 11 in distal section f, in particular in the vicinity of point f5, is thin.

Next, another example in which the estimation information is a change in displacement over time will be given.

Figure 10A:
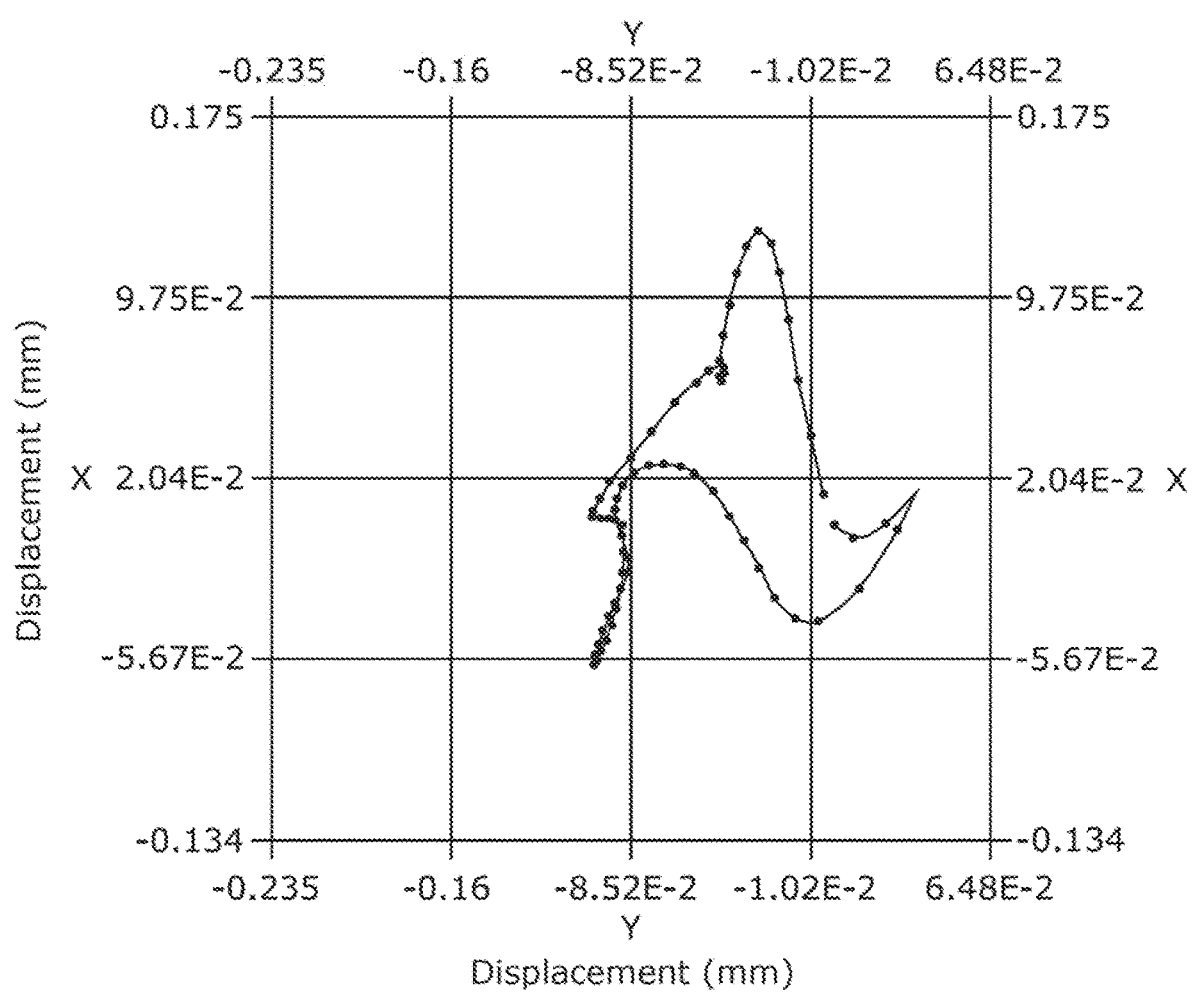
FIG. 10A illustrates changes over time in xy plane displacement of one example of a point of distal section f according to Case 1.
Figure 10B:
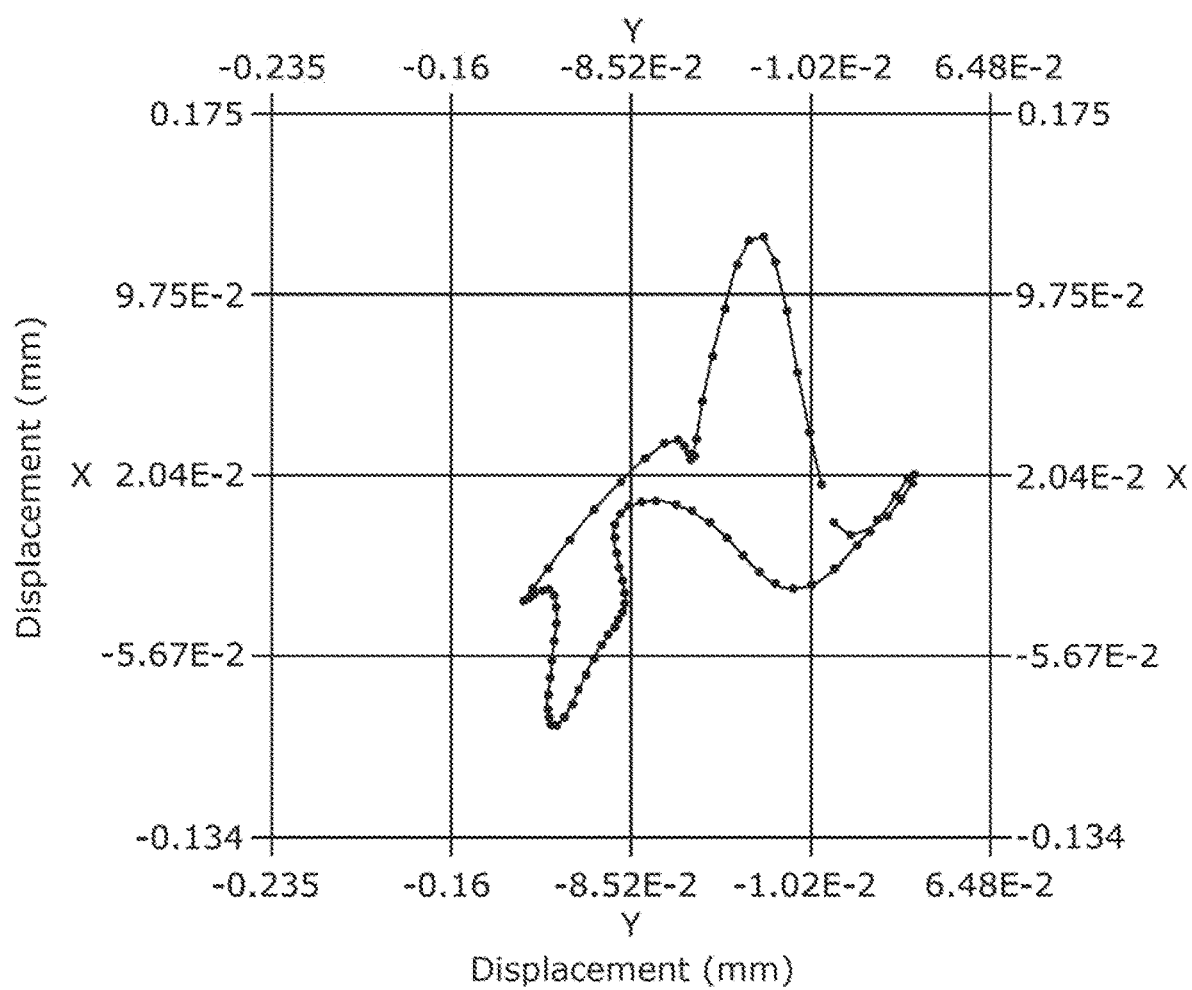
FIG. 10B illustrates changes over time in xy plane displacement of another example of a point of distal section f according to Case 1.
Figure 10C:
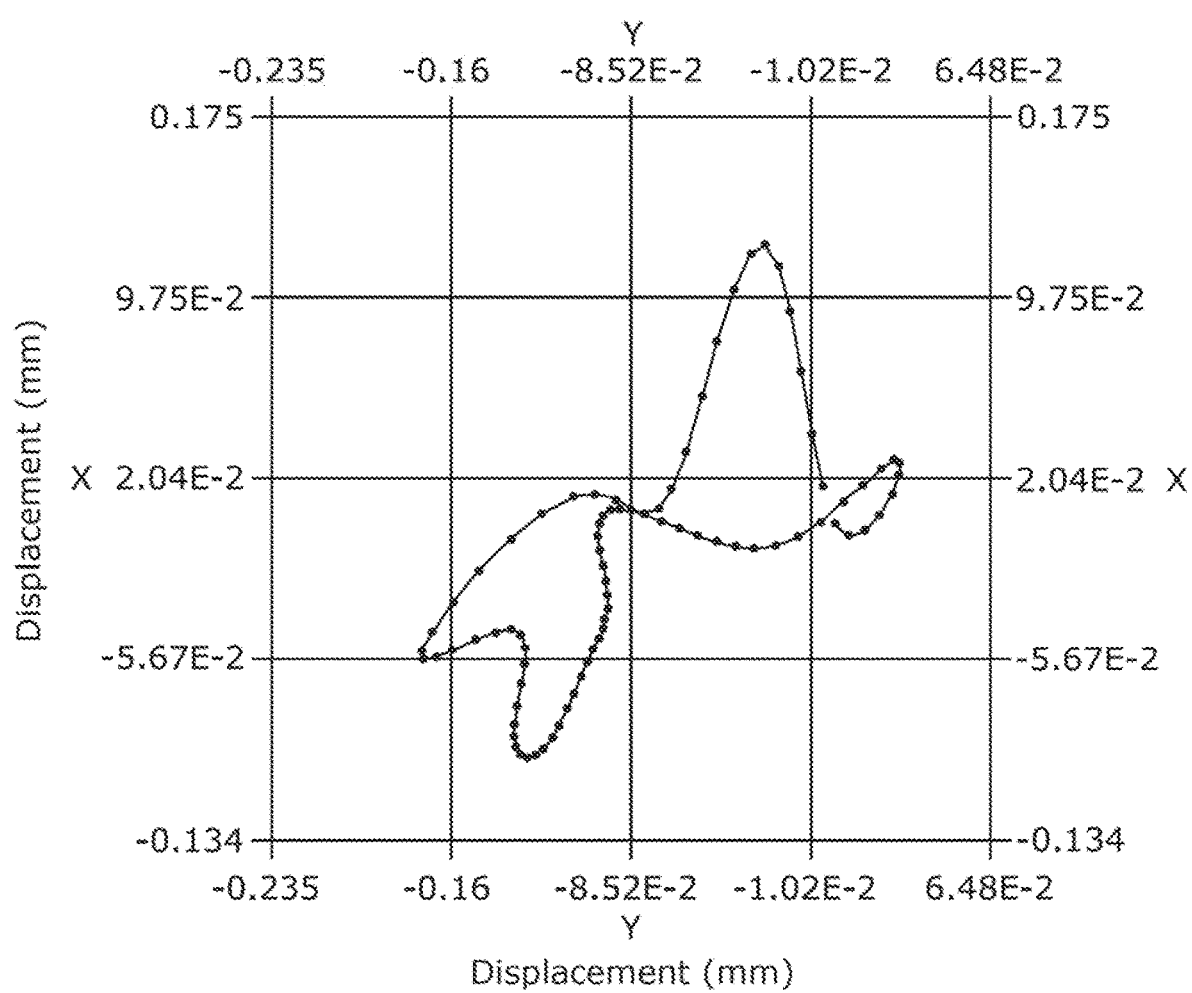
FIG. 10C illustrates changes over time in xy plane displacement of another example of a point of distal section f according to Case 1.
Figure 10D:
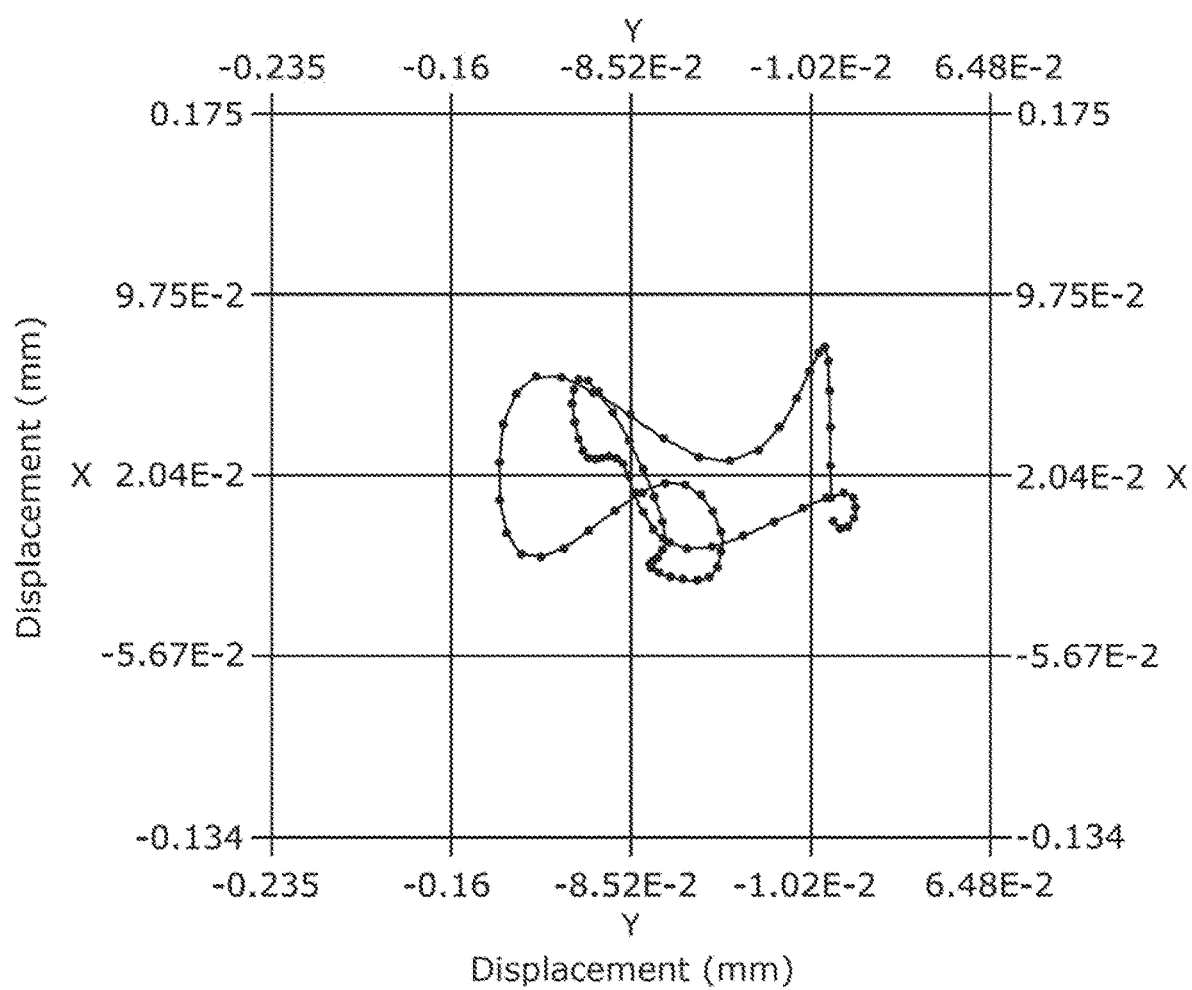
FIG. 10D illustrates changes over time in xy plane displacement of another example of a point of distal section f according to Case 1.
Figure 10E:
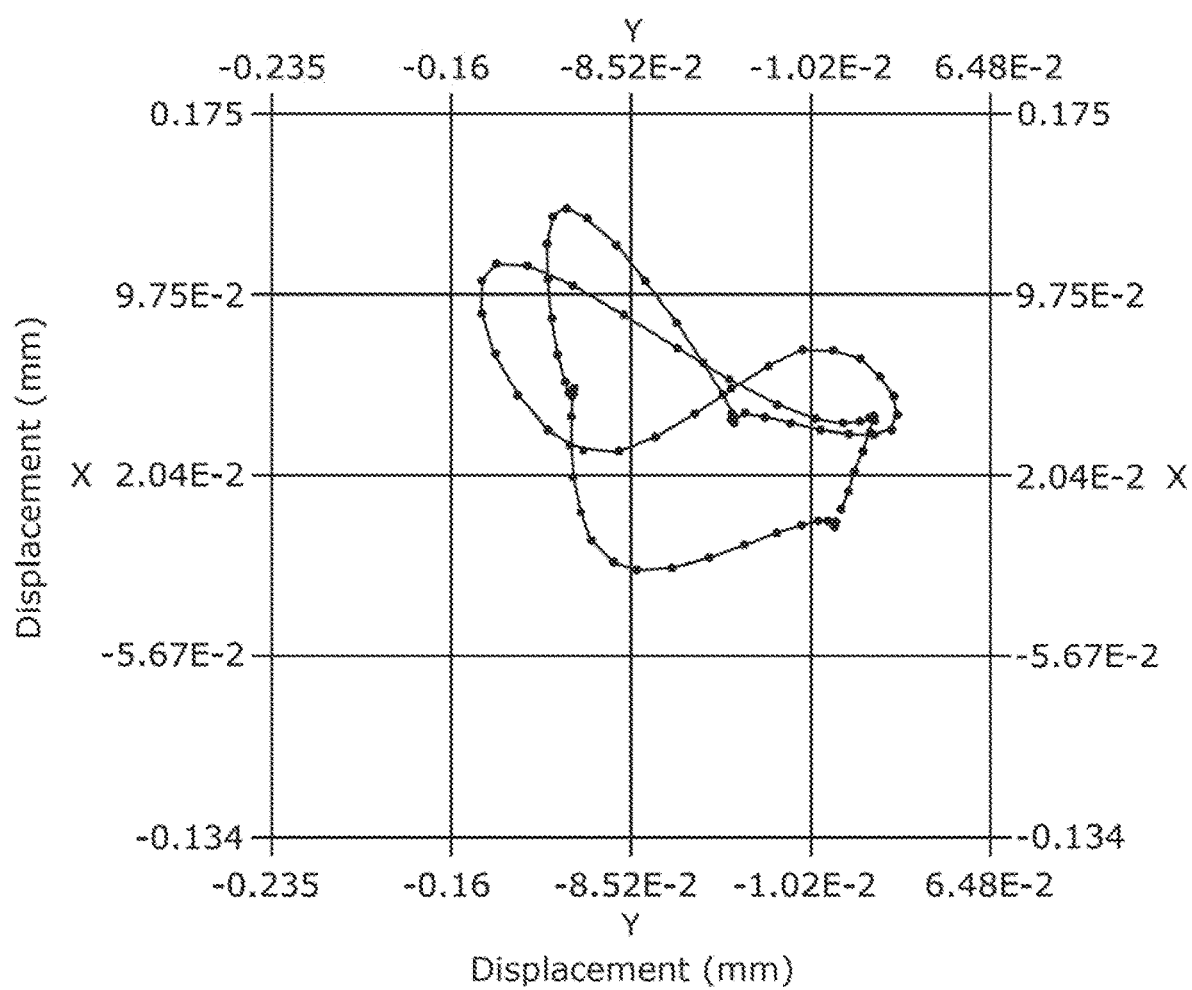
FIG. 10E illustrates changes over time in xy plane displacement of another example of a point of distal section f according to Case 1.
Figure 10F:
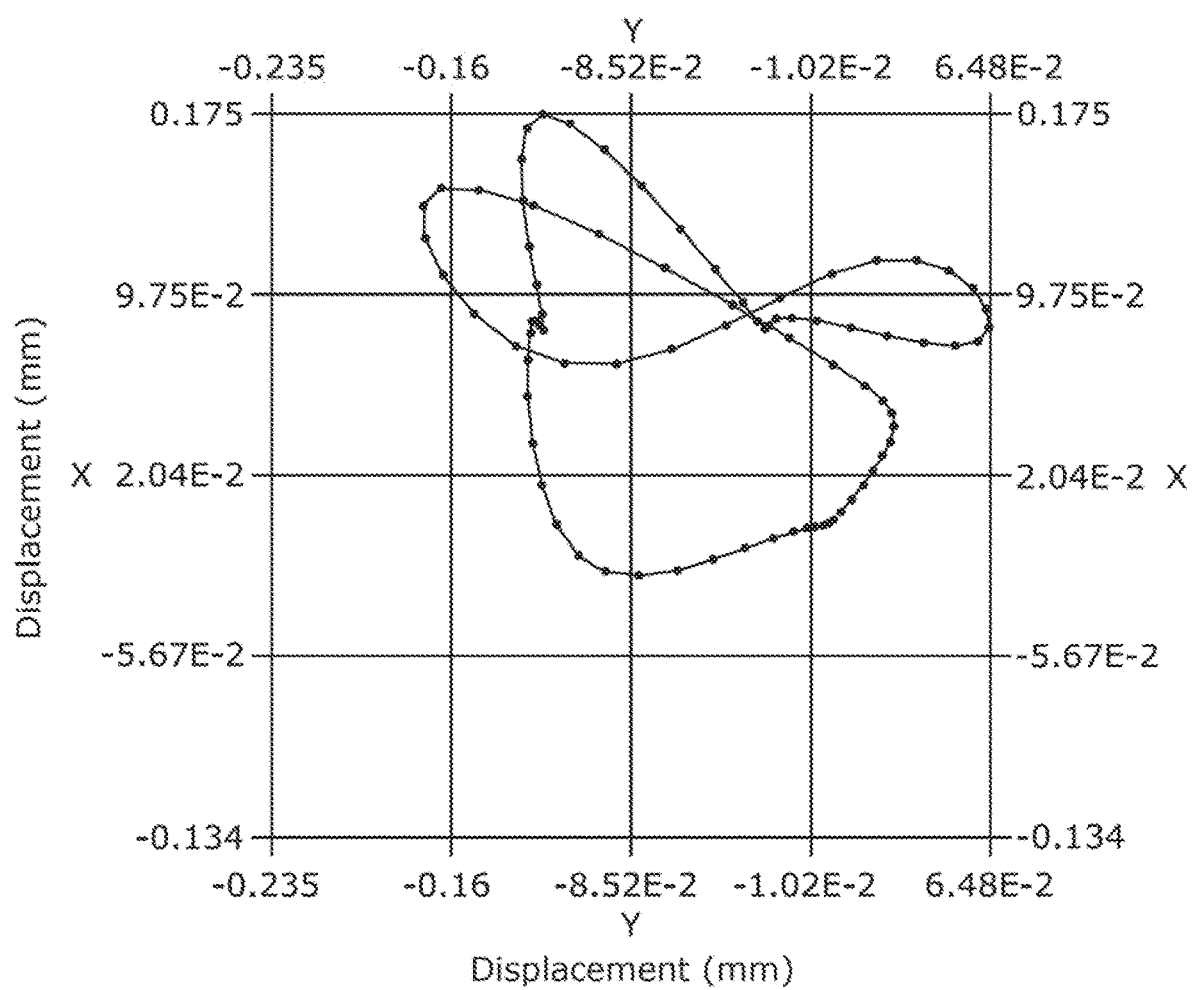
FIG. 10F illustrates changes over time in xy plane displacement of another example of a point of distal section f according to Case 1.
Figure 10G:
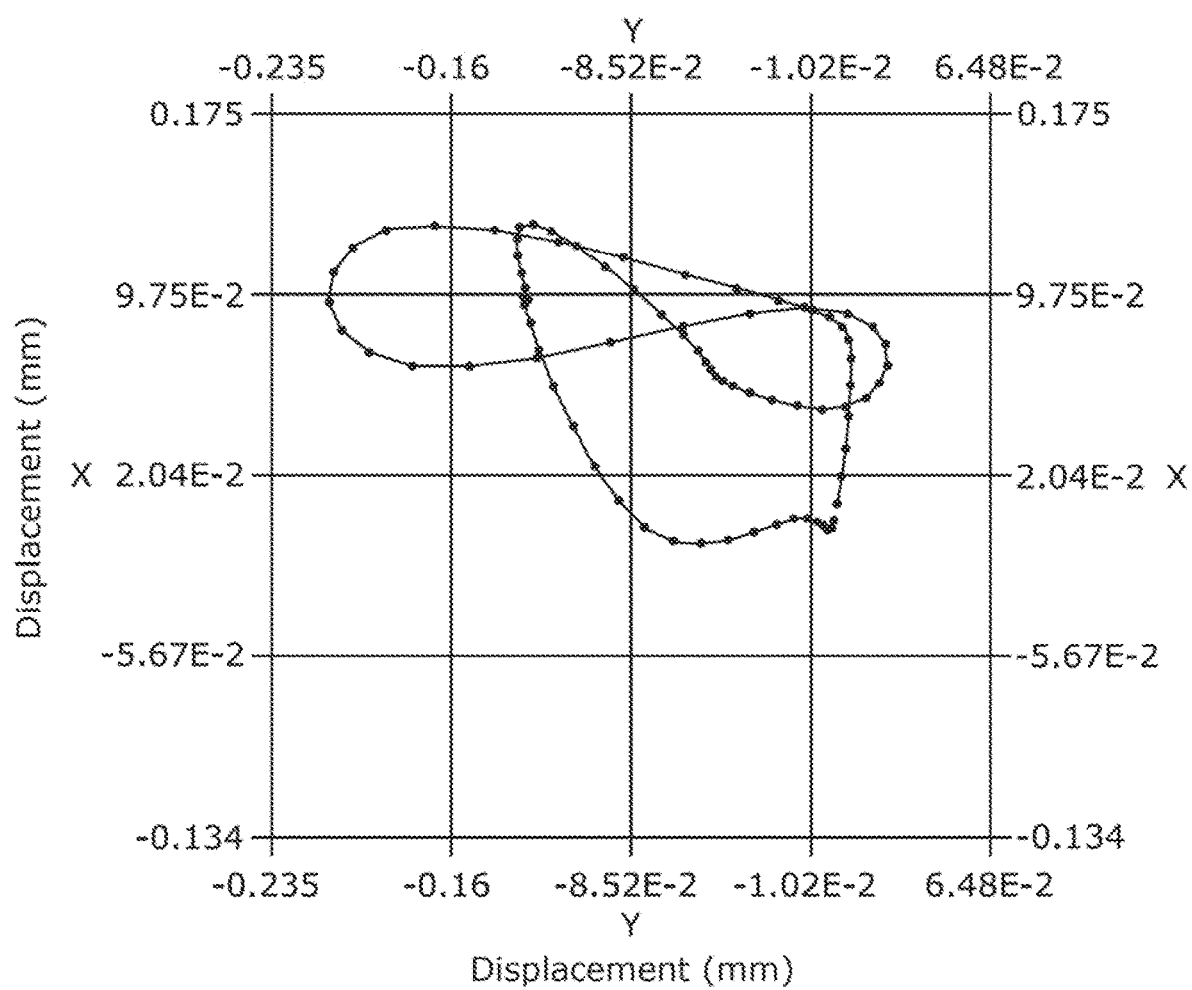
FIG. 10G illustrates changes over time in xy plane displacement of another example of a point of distal section f according to Case 1.
Figure 10H:
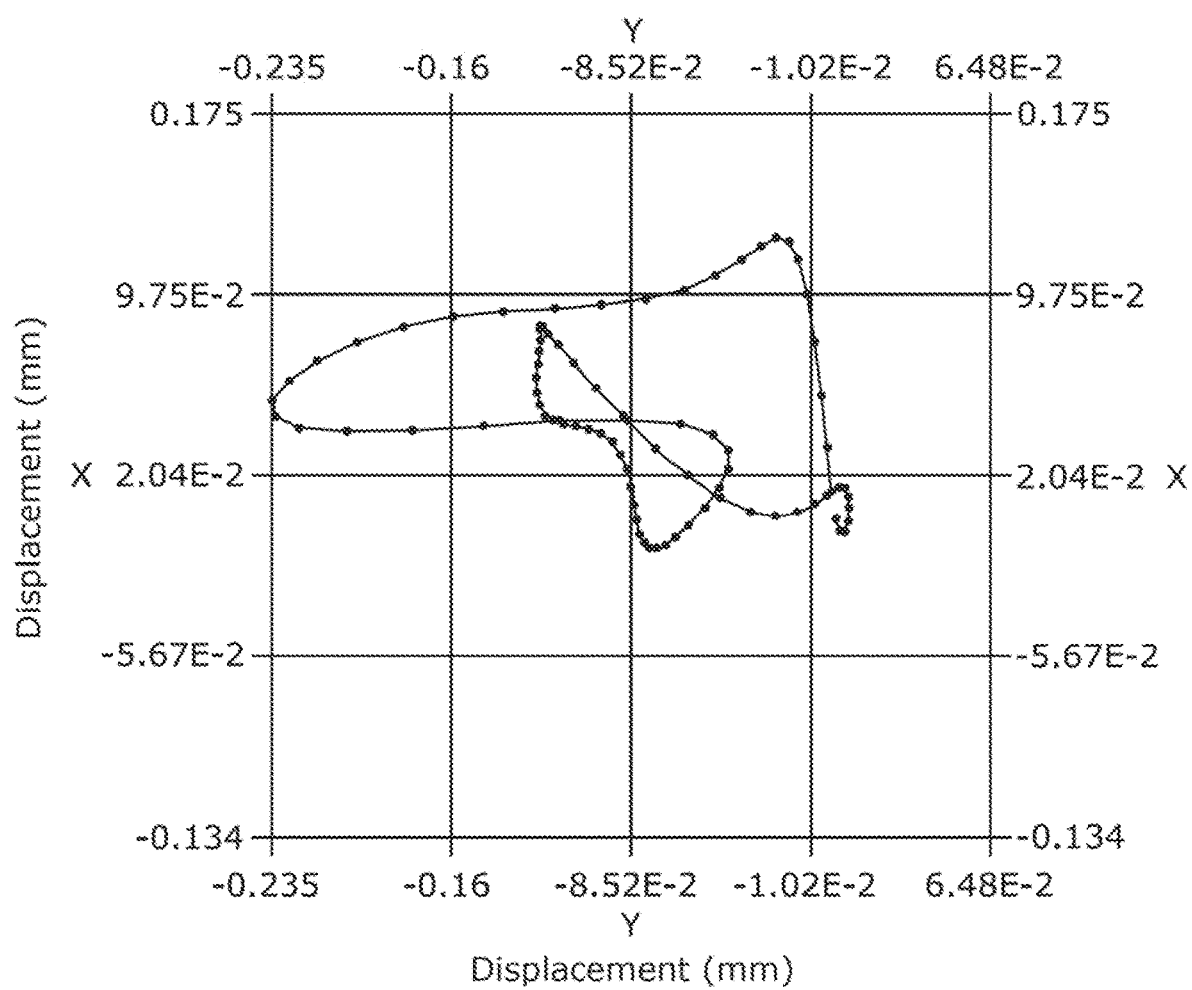
FIG. 10H illustrates changes over time in xy plane displacement of another example of a point of distal section f according to Case 1.
Figure 10I:
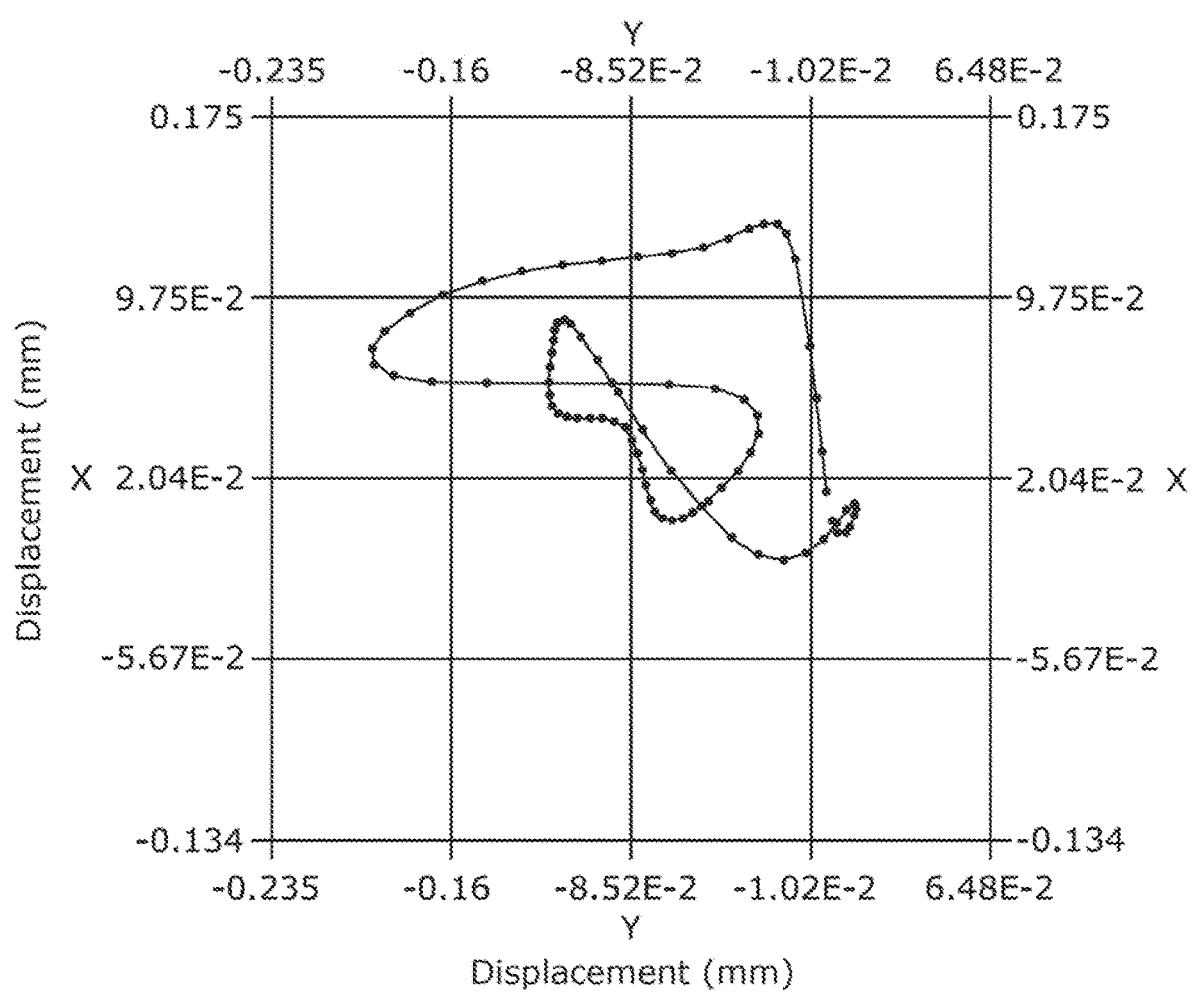
FIG. 10I illustrates changes over time in xy plane displacement of another example of a point of distal section f according to Case 1.
Figure 10J:
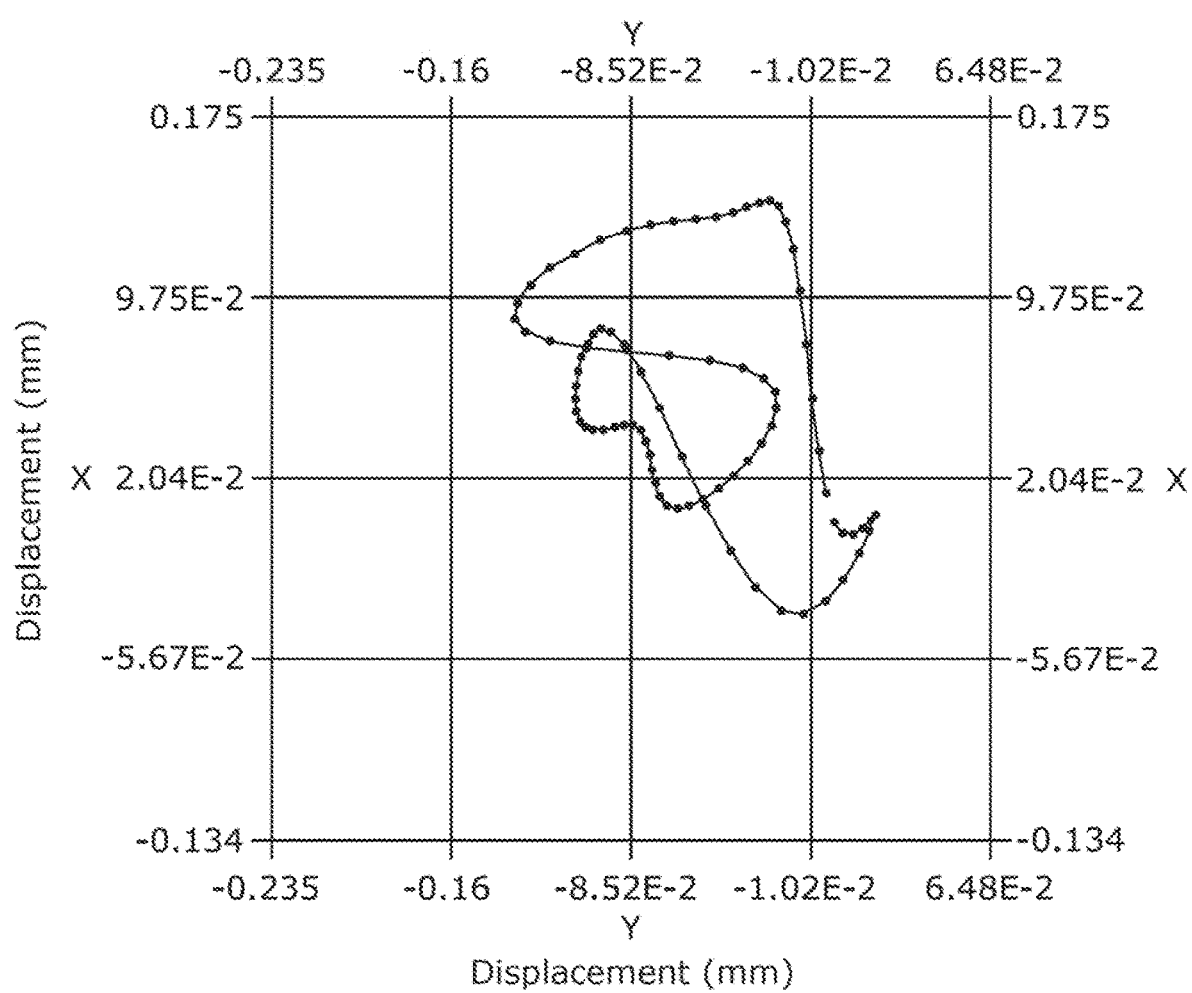
FIG. 10J illustrates changes over time in xy plane displacement of another example of a point of distal section f according to Case 1.
Figure 10K:
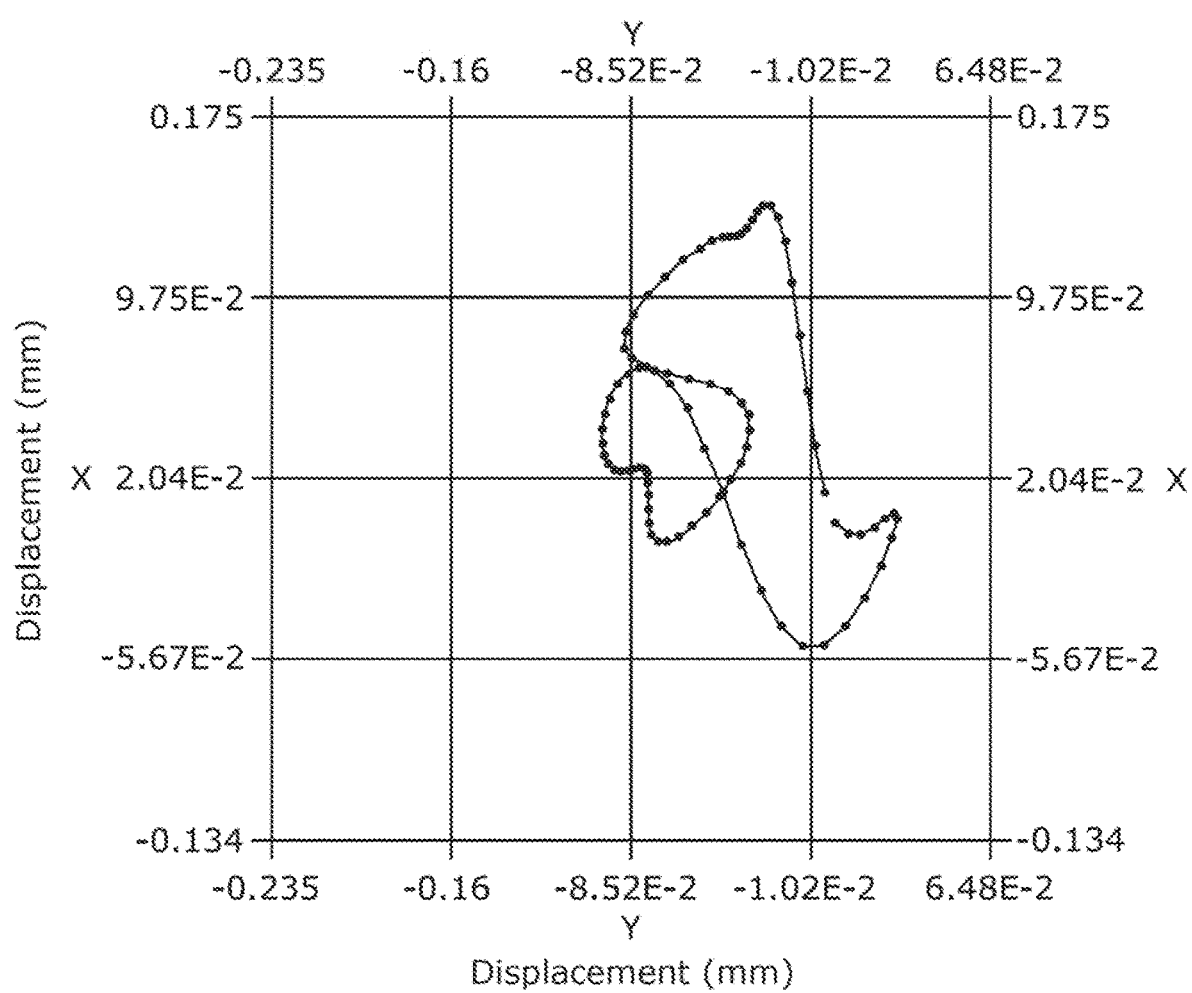
FIG. 10K illustrates changes over time in xy plane displacement of another example of a point of distal section f according to Case 1.
Figure 10L:
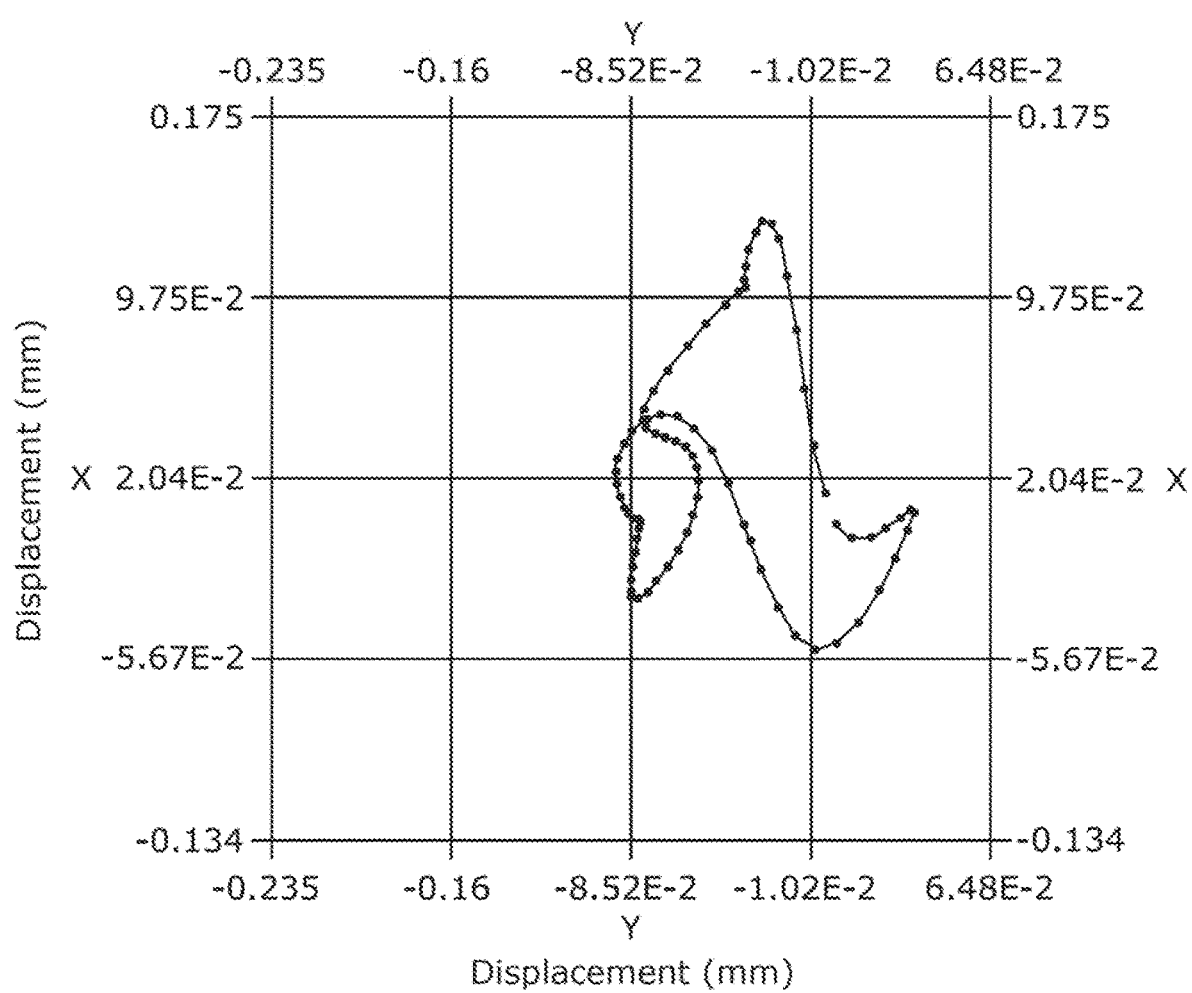
FIG. 10L illustrates changes over time in xy plane displacement of another example of a point of distal section f according to Case 1.

FIG. 10A illustrates changes over time in xy plane displacement of point f0 of distal section f according to Case 1. FIG. 10B illustrates changes over time in xy plane displacement of point f1 of distal section f according to Case 1. FIG. 10C illustrates changes over time in xy plane displacement of point f2 of distal section f according to Case 1. FIG. 10D illustrates changes over time in xy plane displacement of point f3 of distal section f according to Case 1. FIG. 10E illustrates changes over time in xy plane displacement of point f4 of distal section f according to Case 1. FIG. 10F illustrates changes over time in xy plane displacement of point f5 of distal section f according to Case 1. FIG. 10G illustrates changes over time in xy plane displacement of point f6 of distal section f according to Case 1. FIG. 10H illustrates changes over time in xy plane displacement of point f7 of distal section f according to Case 1. FIG. 10I illustrates changes over time in xy plane displacement of point f8 of distal section f according to Case 1. FIG. 10J illustrates changes over time in xy plane displacement of point f9 of distal section f according to Case 1. FIG. 10K illustrates changes over time in xy plane displacement of point f10 of distal section f according to Case 1. FIG. 10L illustrates changes over time in xy plane displacement of point f11 of distal section f according to Case 1.

In FIG. 10A through FIG. 10L, y-axis displacement is represented on the horizontal axis and x-axis displacement is represented on the vertical axis. As FIG. 10A through FIG. 10L illustrate, displacement observed in distal section f is particularly large at point f5 (corresponding to FIG. 10F). More specifically, at point f5, the difference between the maximum and minimum values of displacement, which is one of the indicators, increases. Therefore, the curve drawn by point f5 in FIG. 10F is greatly spread out in the xy plane. Stated differently, it is estimated that the thickness of aneurysm wall 11 in distal section f, in particular in the vicinity of point f5, is thin.

Next, an example in which the estimation information is a change in speed over time will be given.

Figure 11A:
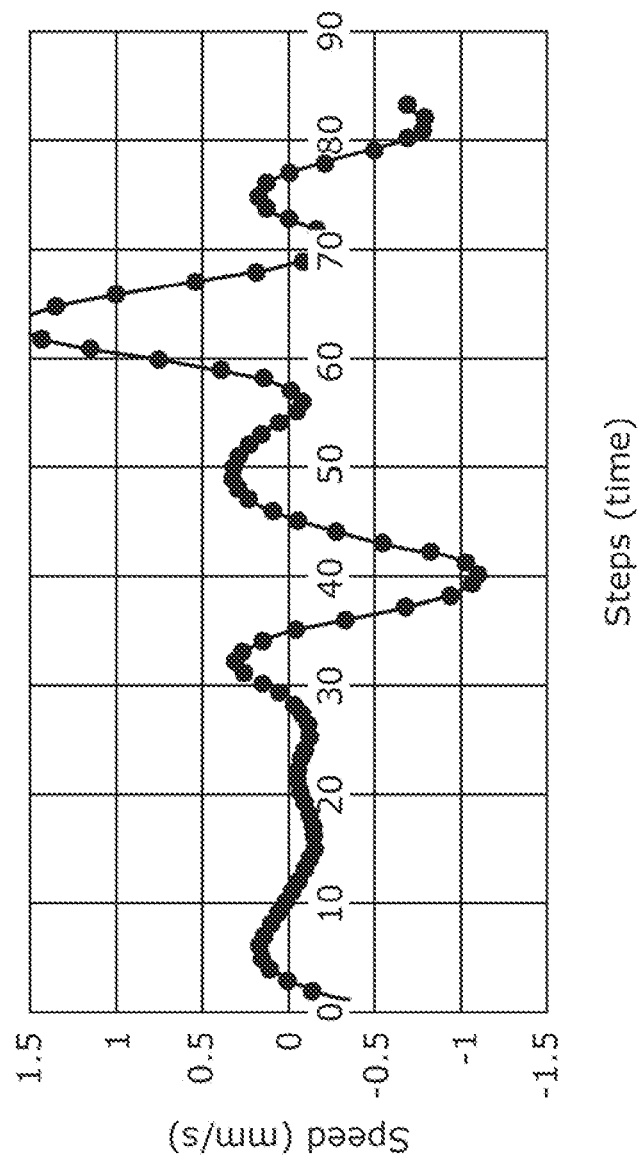
FIG. 11A illustrates changes over time in speed in the z-axis direction of one example of a point of a proximal section according to Case 1.
Figure 11B:
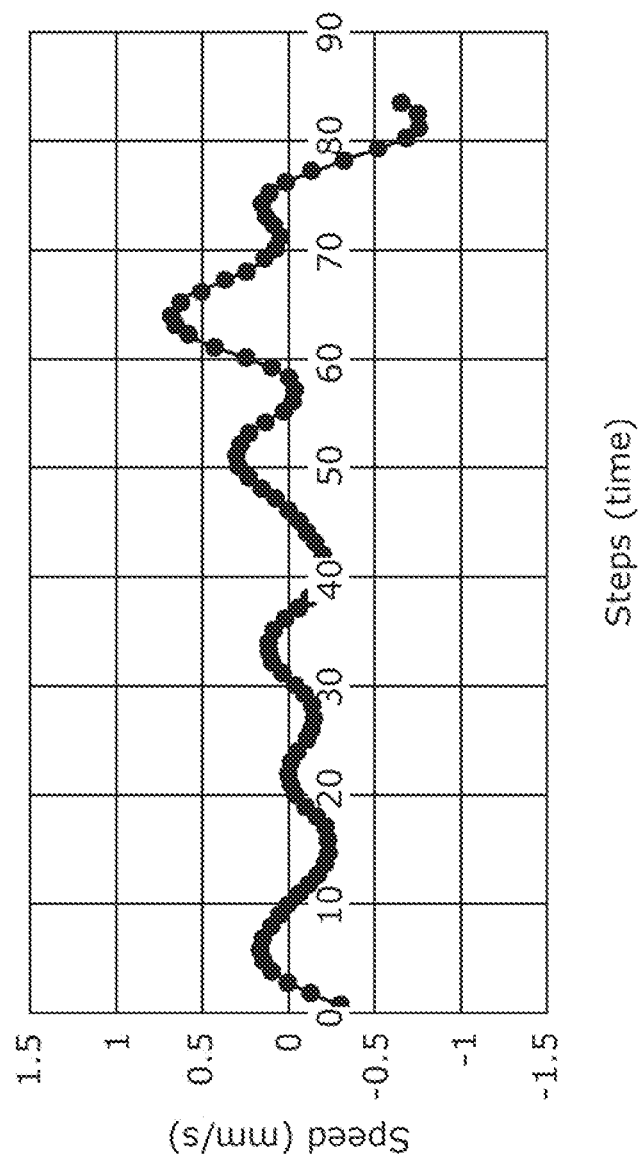
FIG. 11B illustrates changes over time in speed in the z-axis direction of another example of a point of a proximal section according to Case 1.
Figure 12A:
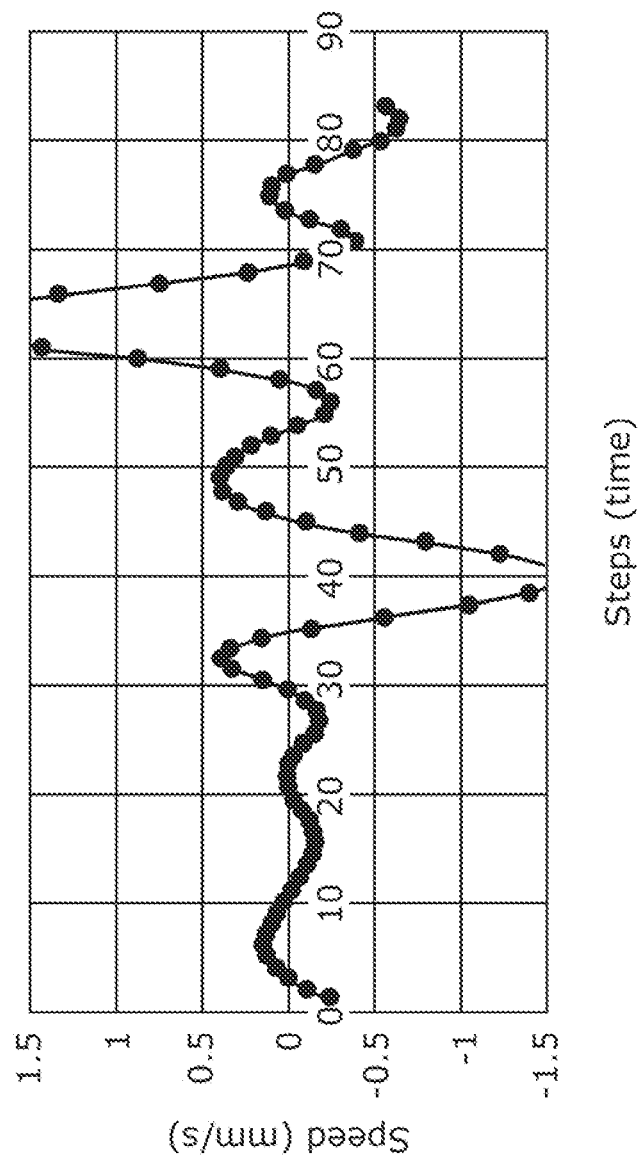
FIG. 12A illustrates changes over time in speed in the z-axis direction of one example of a point of a middle section according to Case 1.
Figure 12B:
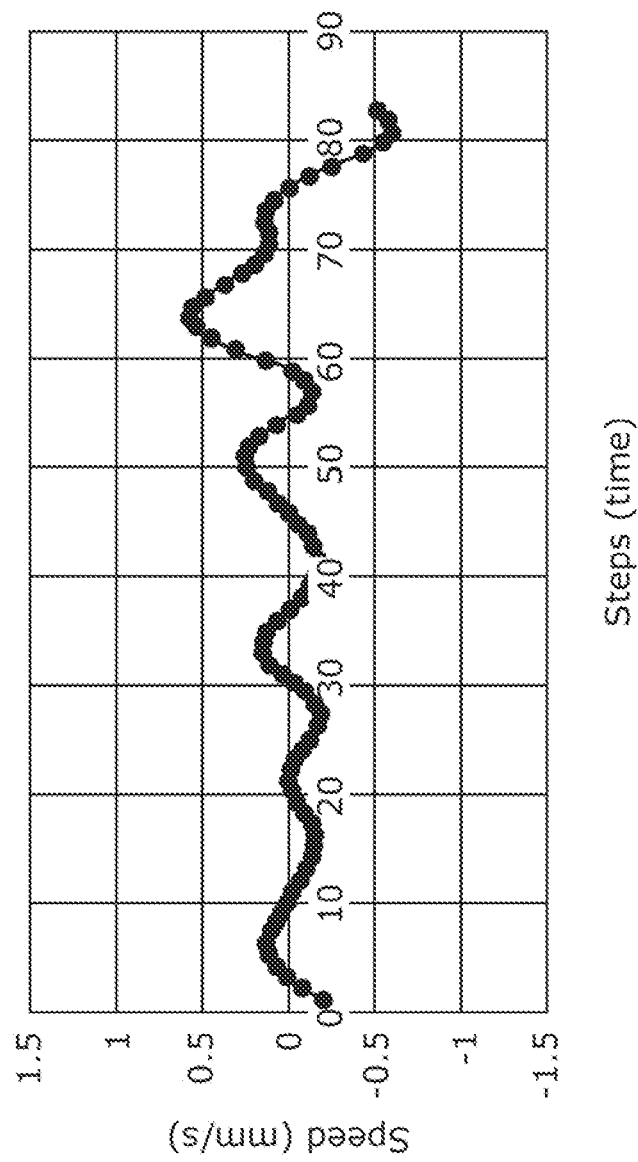
FIG. 12B illustrates changes over time in speed in the z-axis direction of another example of a point of a middle section according to Case 1.
Figure 13A:
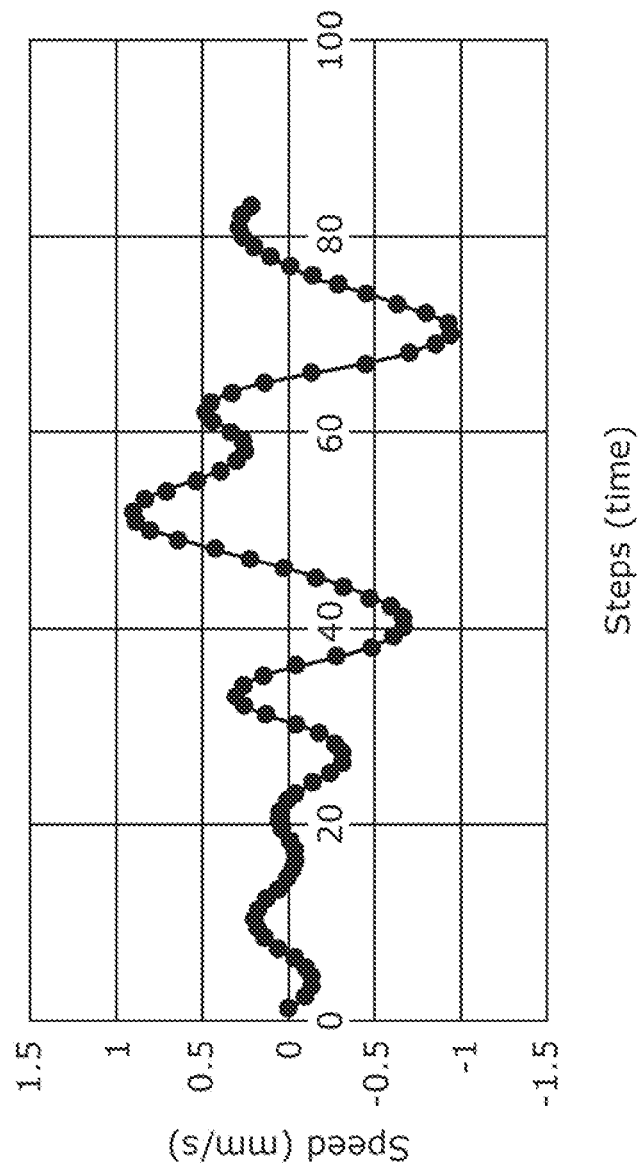
FIG. 13A illustrates changes over time in speed in the z-axis direction of one example of a point of a distal section according to Case 1.
Figure 13B:
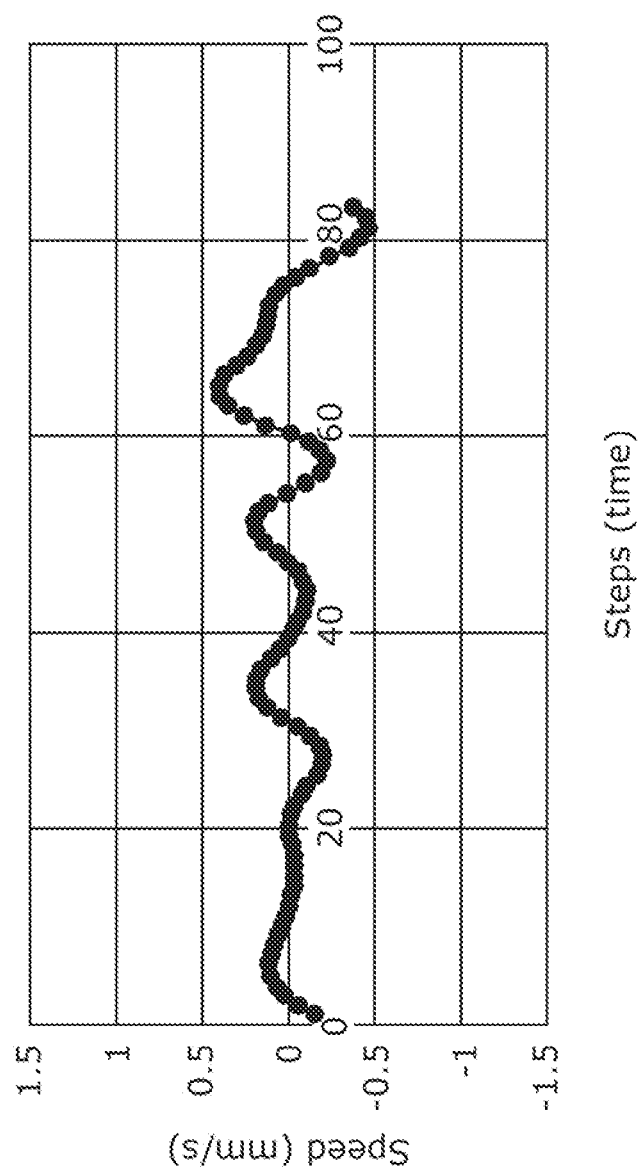
FIG. 13B illustrates changes over time in speed in the z-axis direction of another example of a point of a distal section according to Case 1.

FIG. 11A illustrates changes over time in speed in the z-axis direction of point n1 of proximal section n according to Case 1. FIG. 11B illustrates changes over time in speed in the z-axis direction of point n10 of proximal section n according to Case 1. FIG. 12A illustrates changes over time in speed in the z-axis direction of point m1 of middle section m according to Case 1. FIG. 12B illustrates changes over time in speed in the z-axis direction of point m10 of middle section m according to Case 1. FIG. 13A illustrates changes over time in speed in the z-axis direction of point f5 of distal section f according to Case 1. FIG. 13B illustrates changes over time in speed in the z-axis direction of point f10 of distal section f according to Case 1.

In FIG. 11A through FIG. 13B, the steps, which are units of time, are represented on the horizontal axis, and speed in the z-axis direction is represented on the vertical axis. The speed is a value obtained by calculating the time derivative of a position obtained from the behavioral information.

When the estimation information is a change over time in speed, for example, the thickness of aneurysm wall 11 may be estimated using an indicator such as a maximum value, a maximum value of an absolute value, a difference between maximum and minimum values, an integrated value or an integrated value of an absolute value of the speed. When one of these indicators is used, the greater the value of the indicator is, the thinner aneurysm wall 11 corresponding to the points in the 0 o'clock to 11 o'clock directions is estimated to be since a significant displacement from the origin by the points in the 0 o'clock to 11 o'clock directions correlates to the stretching of aneurysm wall 11 by the pulsation. When the estimation information is a change over time in speed, for example, the number of peaks in the speed may be used as an indicator. As used herein, the term "peak" includes valleys in addition to peaks. When this indicator is used, the greater the value of the indicator is, the thinner aneurysm wall 11 corresponding to the points in the 0 o'clock to 11 o'clock directions is estimated to be since a high number of reverses in the direction of movement of the points in the 0 o'clock to 11 o'clock directions in the x-, y-, or z-axis correlates to the stretching of aneurysm wall 11 by the pulsation.

Next, points n1 and n10 in proximal section n will be compared with reference to FIG. 11A and FIG. 11B. The difference between the maximum and minimum speeds at point n1 illustrated in FIG. 11A is greater than the difference between the maximum and minimum speeds at point n10 illustrated in FIG. 11B. Therefore, because point n1 moves more from the origin than point n10 does, aneurysm wall 11 is easily stretched at point n1 by pulsation, and thus aneurysm wall 11 in the vicinity of point n1 is estimated to be thinner than aneurysm wall 11 in the vicinity of point n10.

Next, points m1 and m10 in middle section m will be compared with reference to FIG. 12A and FIG. 12B, and points f5 and f10 in distal section f will be compared with reference to FIG. 13A and FIG. 13B. The difference between the maximum and minimum speeds at point m1 is greater than the difference between the maximum and minimum speeds at point m10. Therefore, aneurysm wall 11 in the vicinity of point m1 is estimated to be thinner than aneurysm wall 11 in the vicinity of point m10. Similarly, the difference between the maximum and minimum speeds at point f5 is greater than the difference between the maximum and minimum speeds at point f10. Therefore, aneurysm wall 11 in the vicinity of point f5 is estimated to be thinner than aneurysm wall 11 in the vicinity of point f10.

Next, an example in which the estimation information is a change in acceleration over time will be given.

Figure 14A:
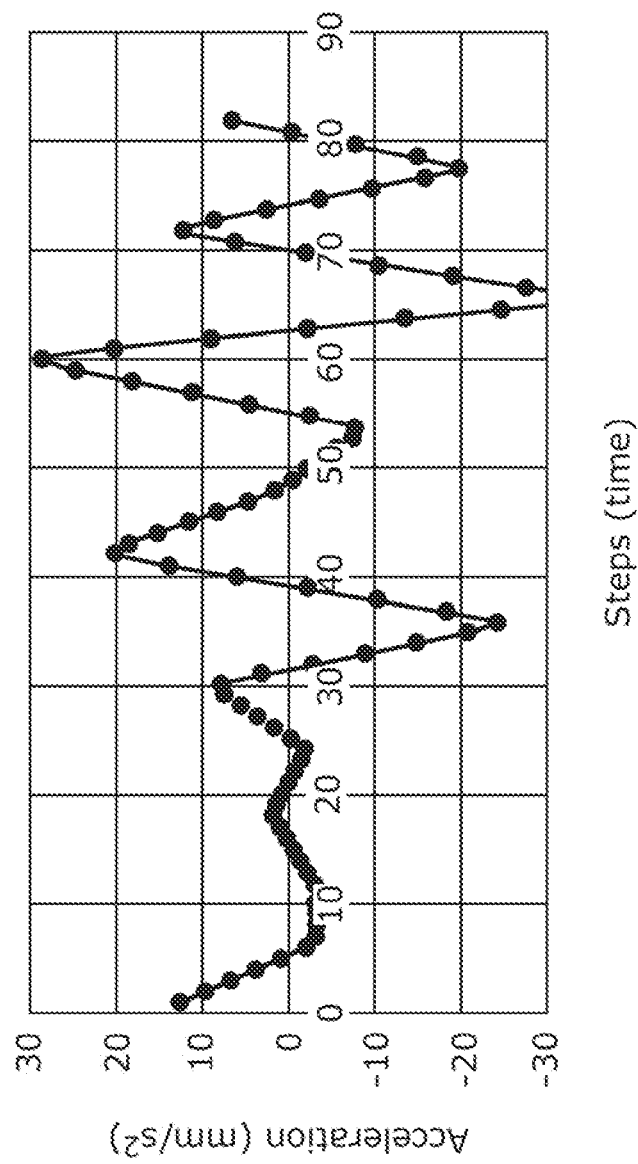
FIG. 14A illustrates changes over time in acceleration in the z-axis direction of one example of a point of a proximal section according to Case 1.
Figure 14B:
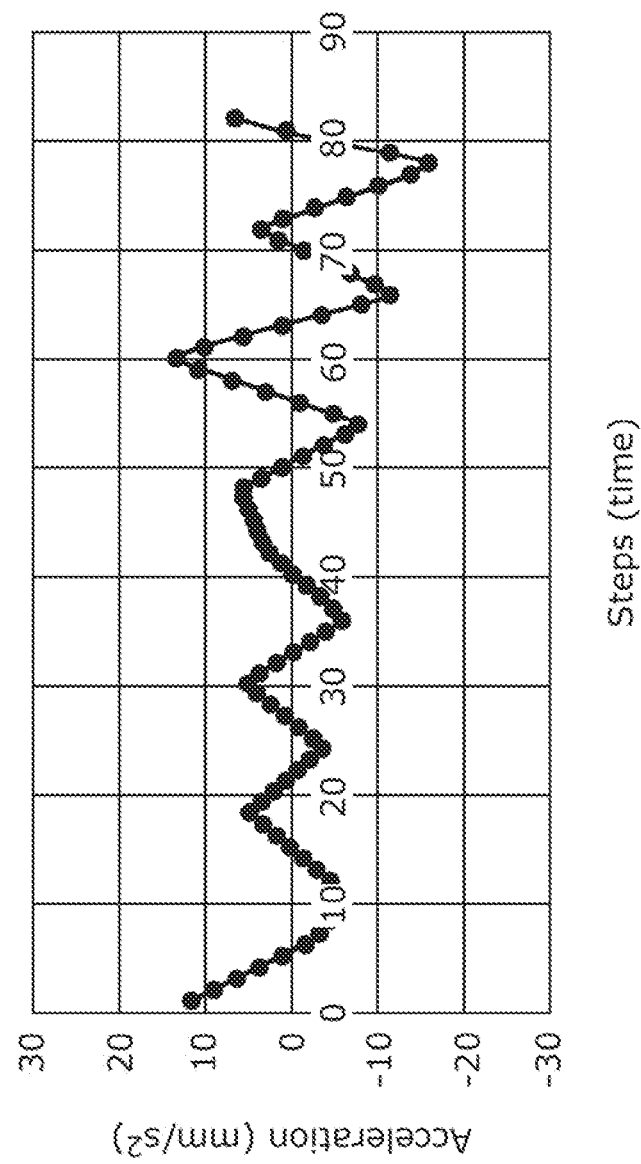
FIG. 14B illustrates changes over time in acceleration in the z-axis direction of another example of a point of a proximal section according to Case 1.
Figure 15A:
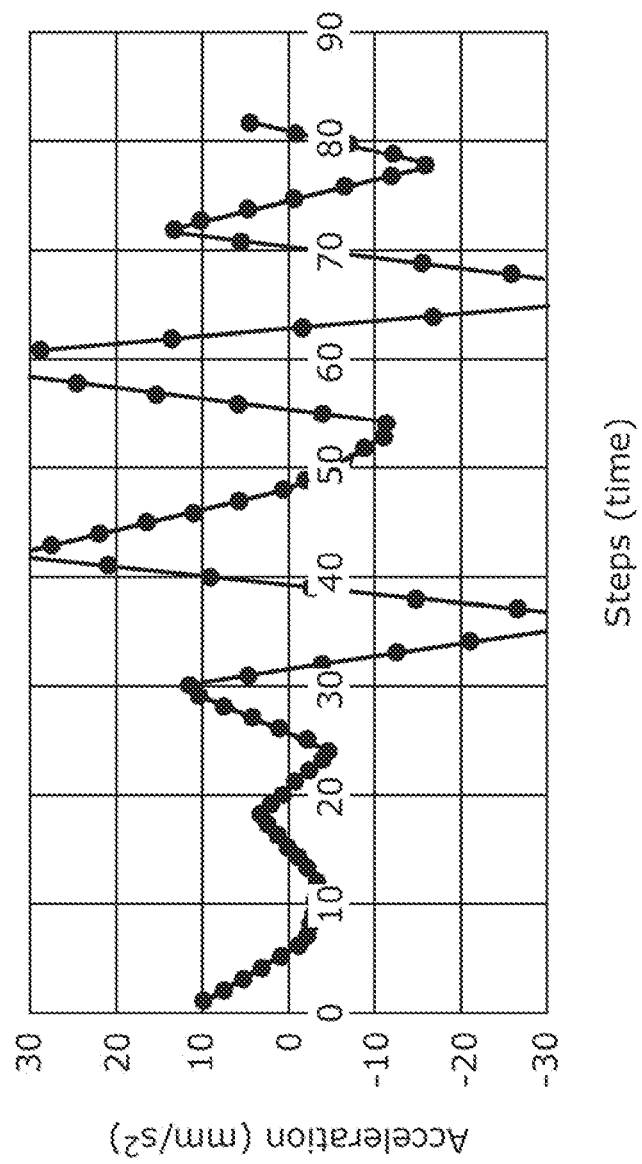
FIG. 15A illustrates changes over time in acceleration in the z-axis direction of one example of a point of a middle section according to Case 1.
Figure 15B:
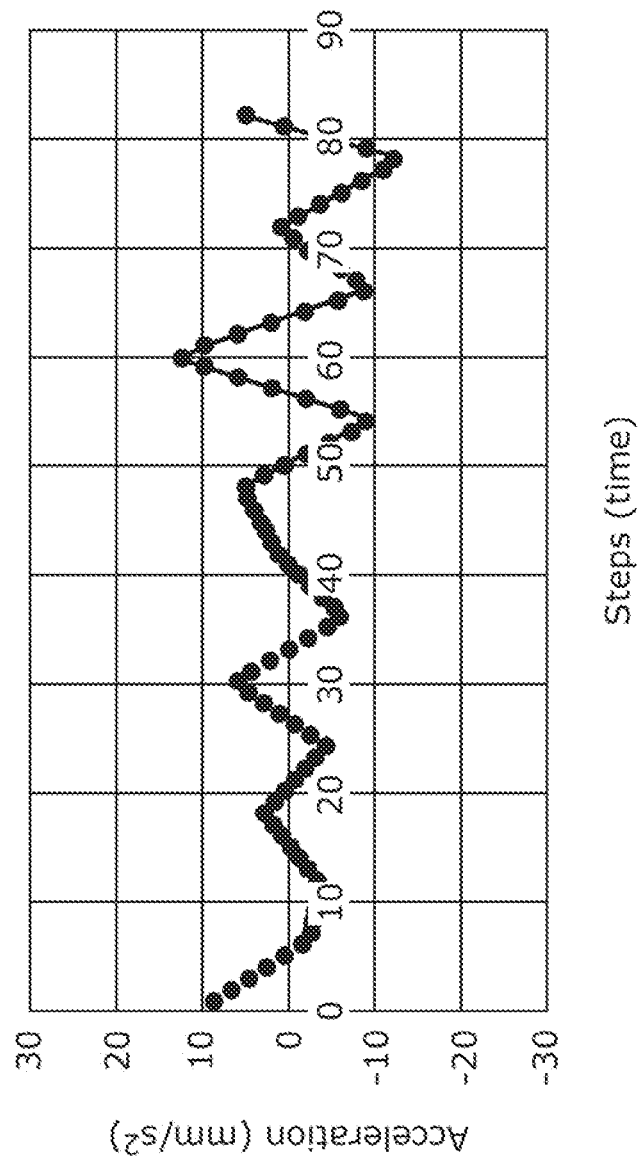
FIG. 15B illustrates changes over time in acceleration in the z-axis direction of another example of a point of a middle section according to Case 1.
Figure 16B:
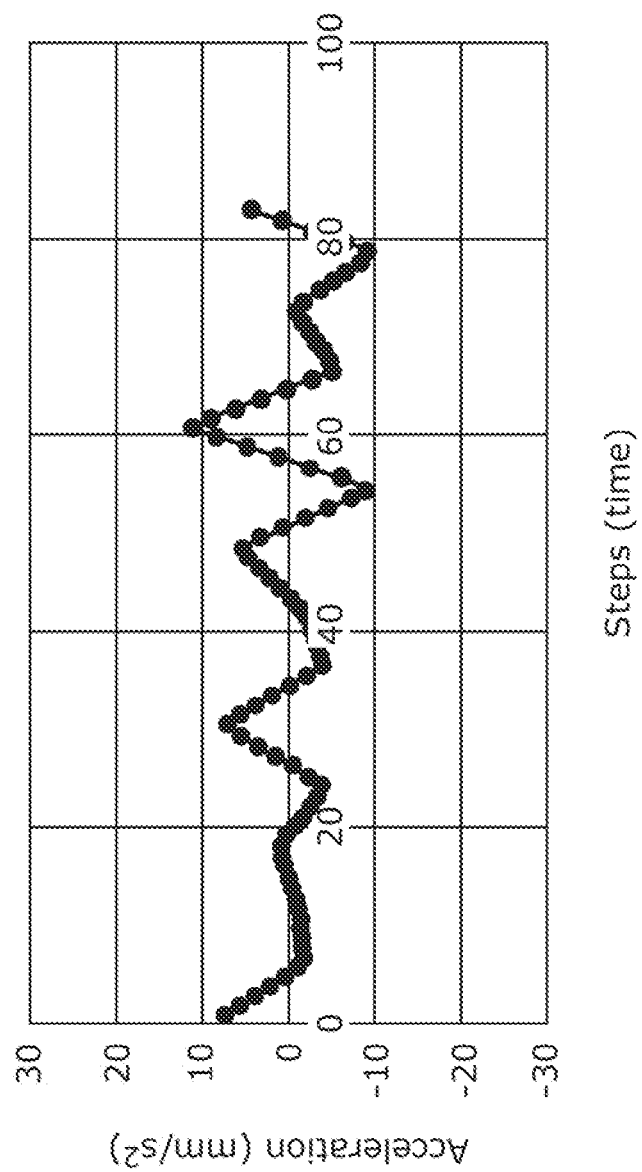
FIG. 16B illustrates changes over time in acceleration in the z-axis direction of another example of a point of a distal section according to Case 1.

FIG. 14A illustrates changes over time in acceleration in the z-axis direction of point n1 of proximal section n according to Case 1. FIG. 14B illustrates changes over time in acceleration in the z-axis direction of point n10 of proximal section n according to Case 1. FIG. 15A illustrates changes over time in acceleration in the z-axis direction of point m1 of middle section m according to Case 1. FIG. 15B illustrates changes over time in acceleration in the z-axis direction of point m10 of middle section m according to Case 1. FIG. 16A illustrates changes over time in acceleration in the z-axis direction of point f5 of distal section f according to Case 1. FIG. 16B illustrates changes over time in acceleration in the z-axis direction of point f10 of distal section f according to Case 1.

In FIG. 14A through FIG. 16B, the steps, which are units of time, are represented on the horizontal axis, and acceleration in the z-axis direction is represented on the vertical axis. The acceleration is a value obtained by calculating the time derivative of the above-described speed.

When the estimation information is a change over time in acceleration, for example, the thickness of aneurysm wall 11 may be estimated using the same indicator as when the estimation information is a change over time in speed. More specifically, the thickness of aneurysm wall 11 may be estimated using an indicator such as a maximum value, a maximum value of an absolute value, a difference between maximum and minimum values, an integrated value, an integrated value of an absolute value, or a number of peaks of the acceleration. When the estimation information is a change over time in acceleration, just as when the estimation information is a change over time in speed, the larger these indicator values are, the more easily aneurysm wall 11 is stretched by pulsation and the thinner aneurysm wall 11 is estimated to be.

Next, points n1 and n10 in proximal section n will be compared with reference to FIG. 14A and FIG. 14B. The difference between the maximum and minimum accelerations at point n1 illustrated in FIG. 14A is greater than the difference between the maximum and minimum accelerations at point n10 illustrated in FIG. 14B. Therefore, because point n1 moves more from the origin than point n10 does, aneurysm wall 11 is easily stretched at point n1 by pulsation, and thus aneurysm wall 11 in the vicinity of point n1 is estimated to be thinner than aneurysm wall 11 in the vicinity of point n10.

Next, points m1 and m10 in middle section m will be compared with reference to FIG. 15A and FIG. 15B, and points f5 and f10 in distal section f will be compared with reference to FIG. 16A and FIG. 16B. The difference between the maximum and minimum accelerations at point m1 is greater than the difference between the maximum and minimum accelerations at point m10. Therefore, aneurysm wall 11 in the vicinity of point m1 is estimated to be thinner than aneurysm wall 11 in the vicinity of point m10. Similarly, the difference between the maximum and minimum accelerations at point f5 is greater than the difference between the maximum and minimum accelerations at point f10. Therefore, aneurysm wall 11 in the vicinity of point f5 is estimated to be thinner than aneurysm wall 11 in the vicinity of point f10.

In FIG. 11A through FIG. 16B, the z-axis is used as one example, but when the estimation information is a change over time in speed or a change over time in acceleration, the same trend in the thickness of aneurysm wall 11 as in the z-axis can be seen in the x- and the y-axes as well.

Next, an example in which the estimation information is a change in kinetic energy over time will be given.

Figure 17A:
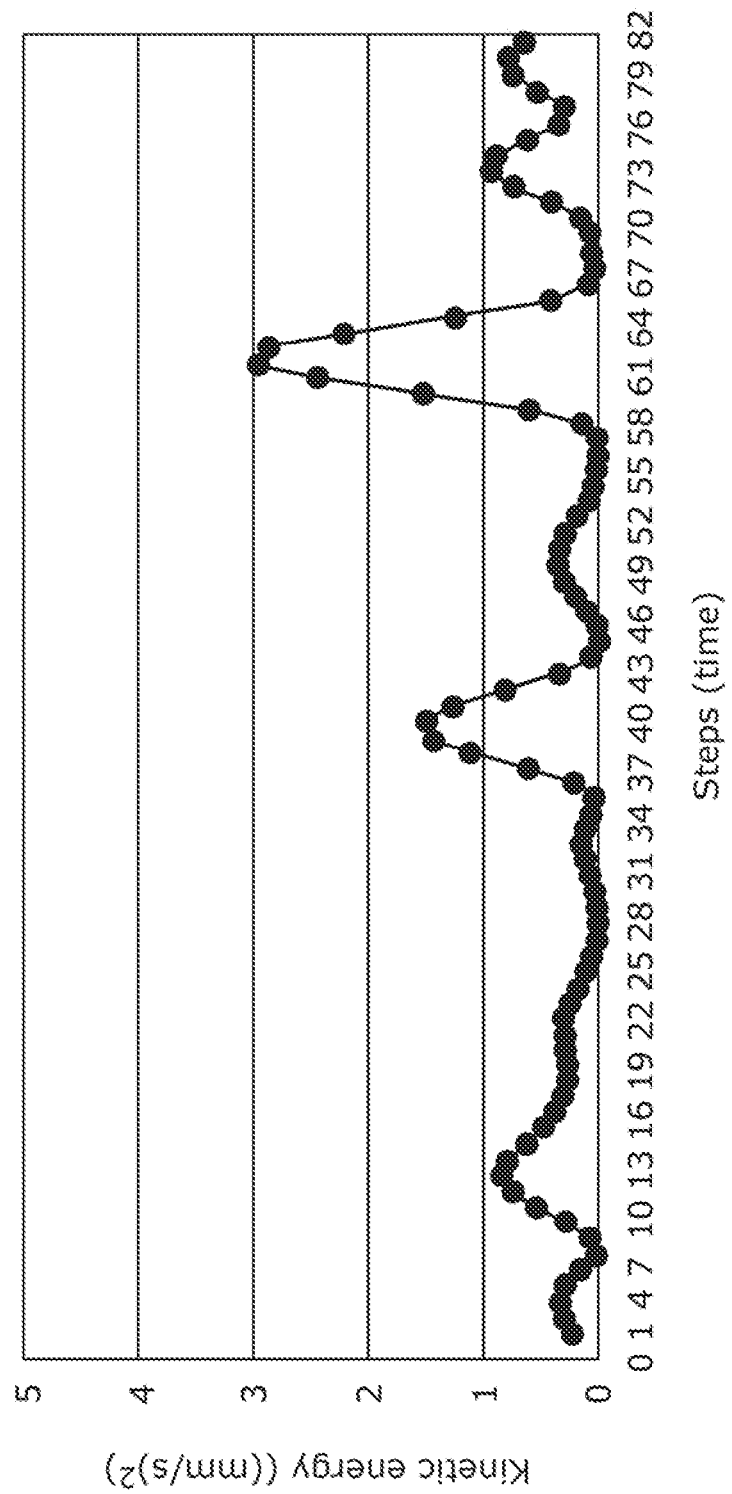
FIG. 17A illustrates changes over time in kinetic energy of one example of a point of a proximal section according to Case 1.
Figure 18A:
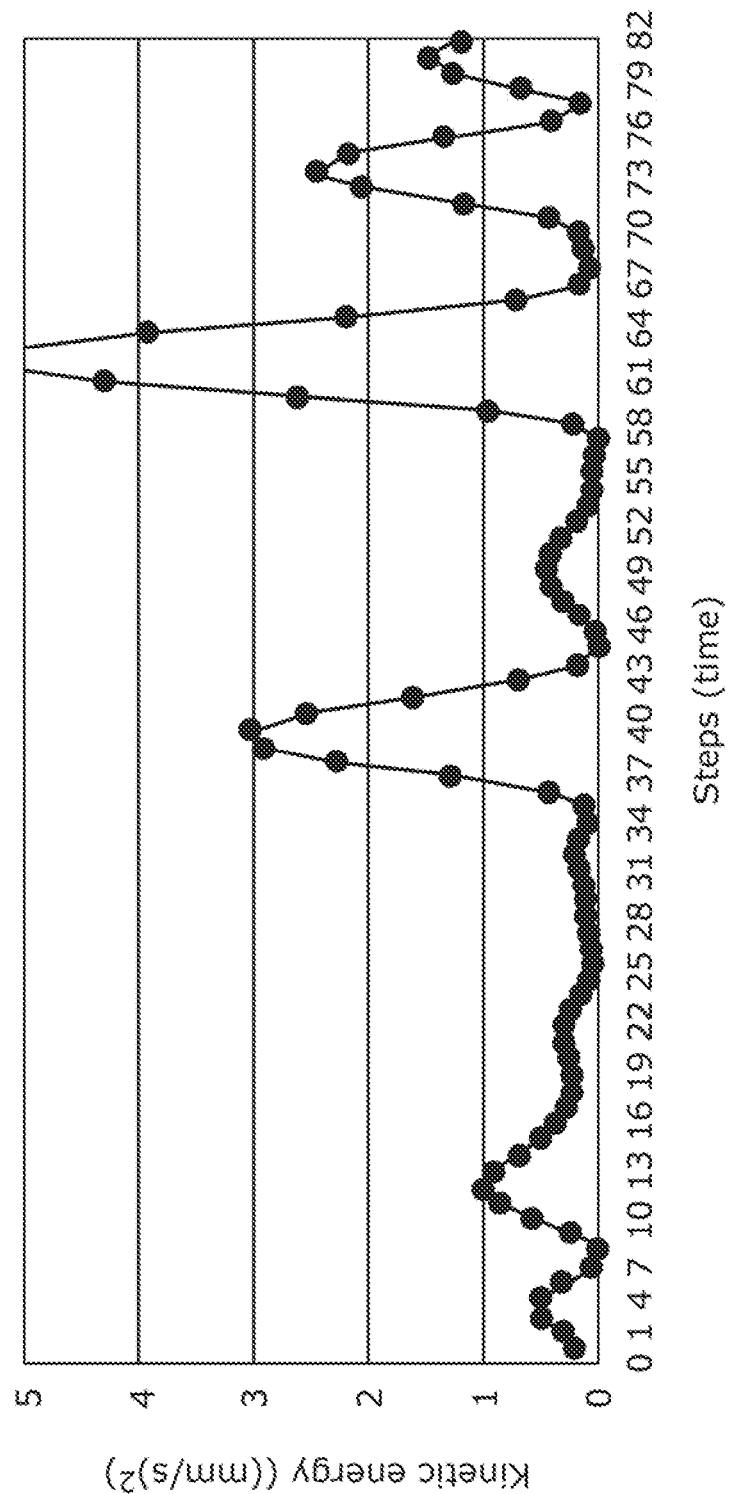
FIG. 18A illustrates changes over time in kinetic energy of one example of a point of a middle section according to Case 1.
Figure 18B:
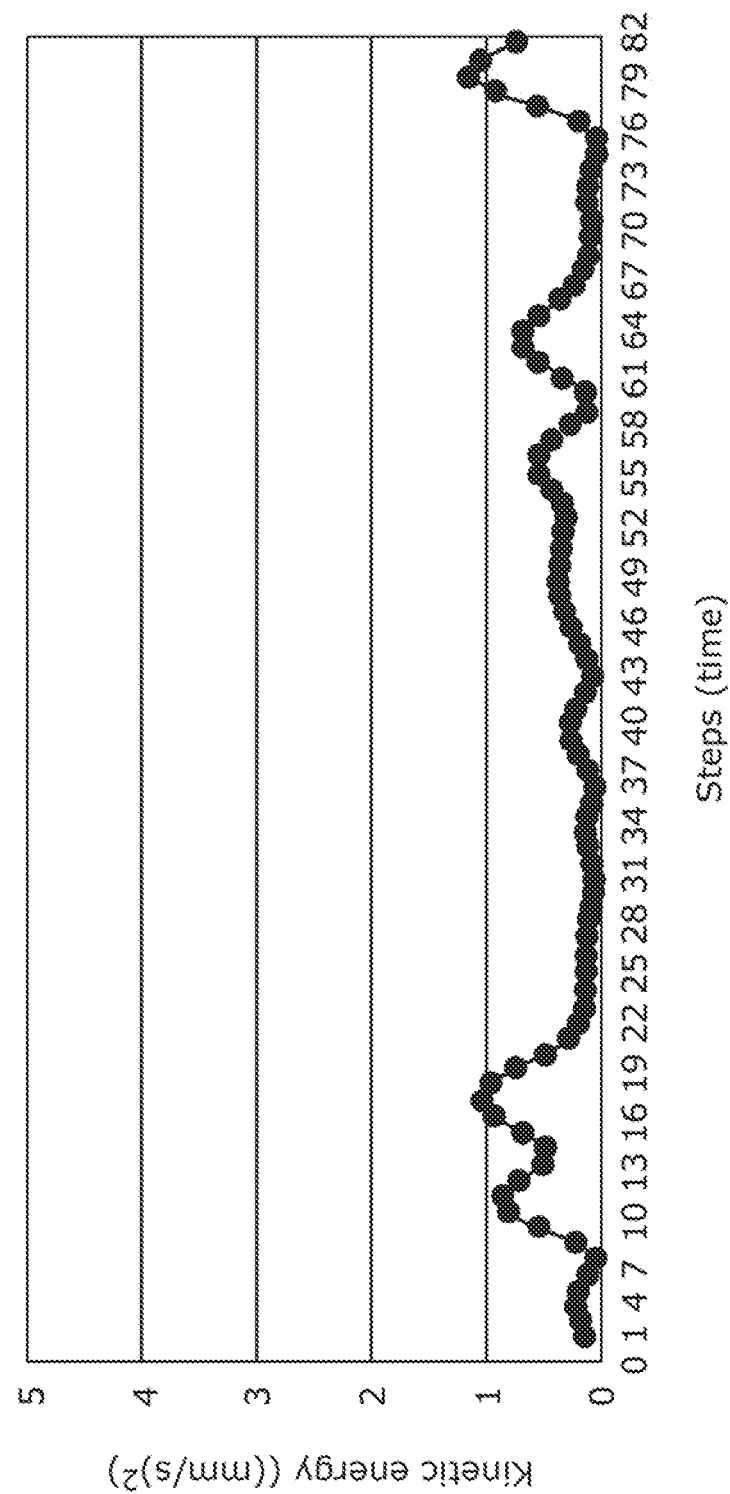
FIG. 18B illustrates changes over time in kinetic energy of another example of a point of a middle section according to Case 1.
Figure 19A:
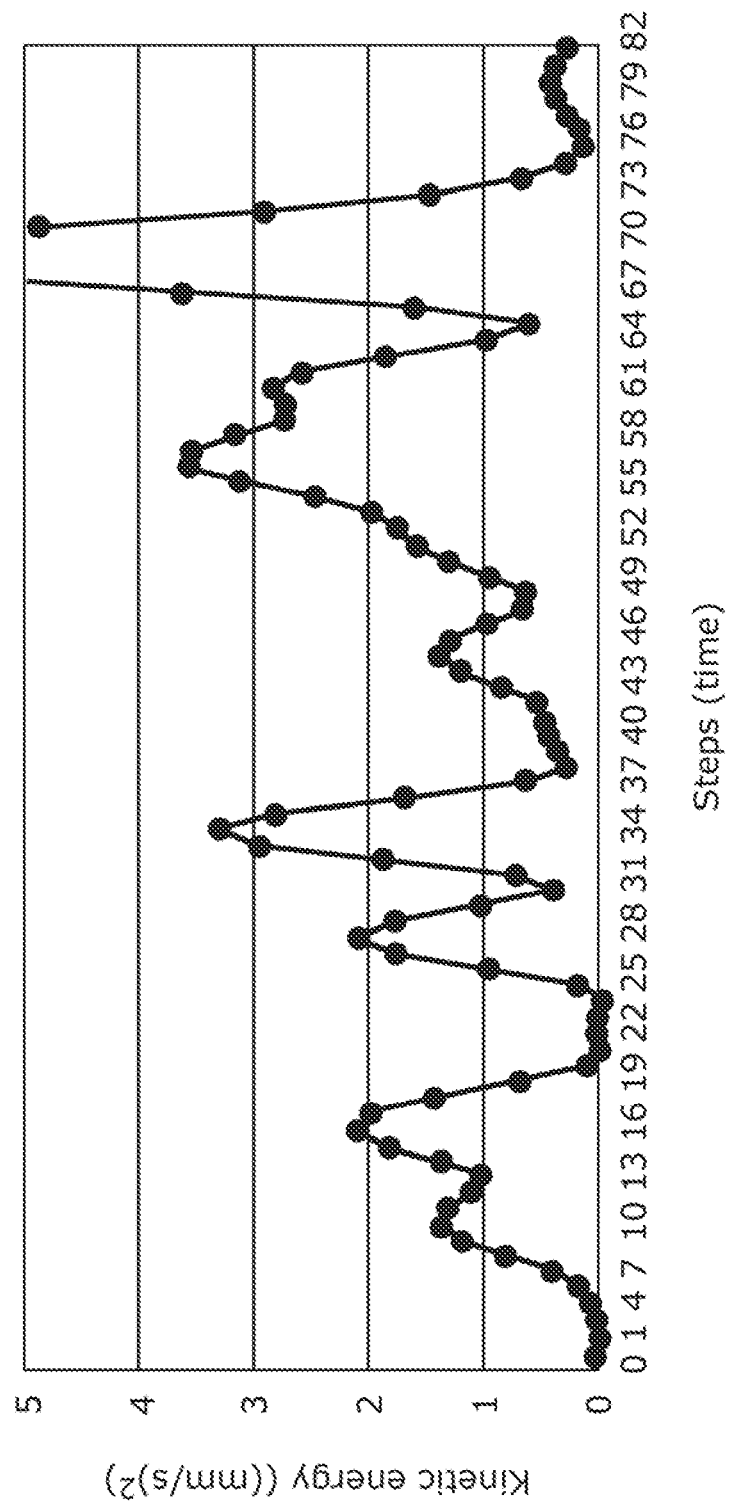
FIG. 19A illustrates changes over time in kinetic energy of one example of a point of a distal section according to Case 1.
Figure 19B:
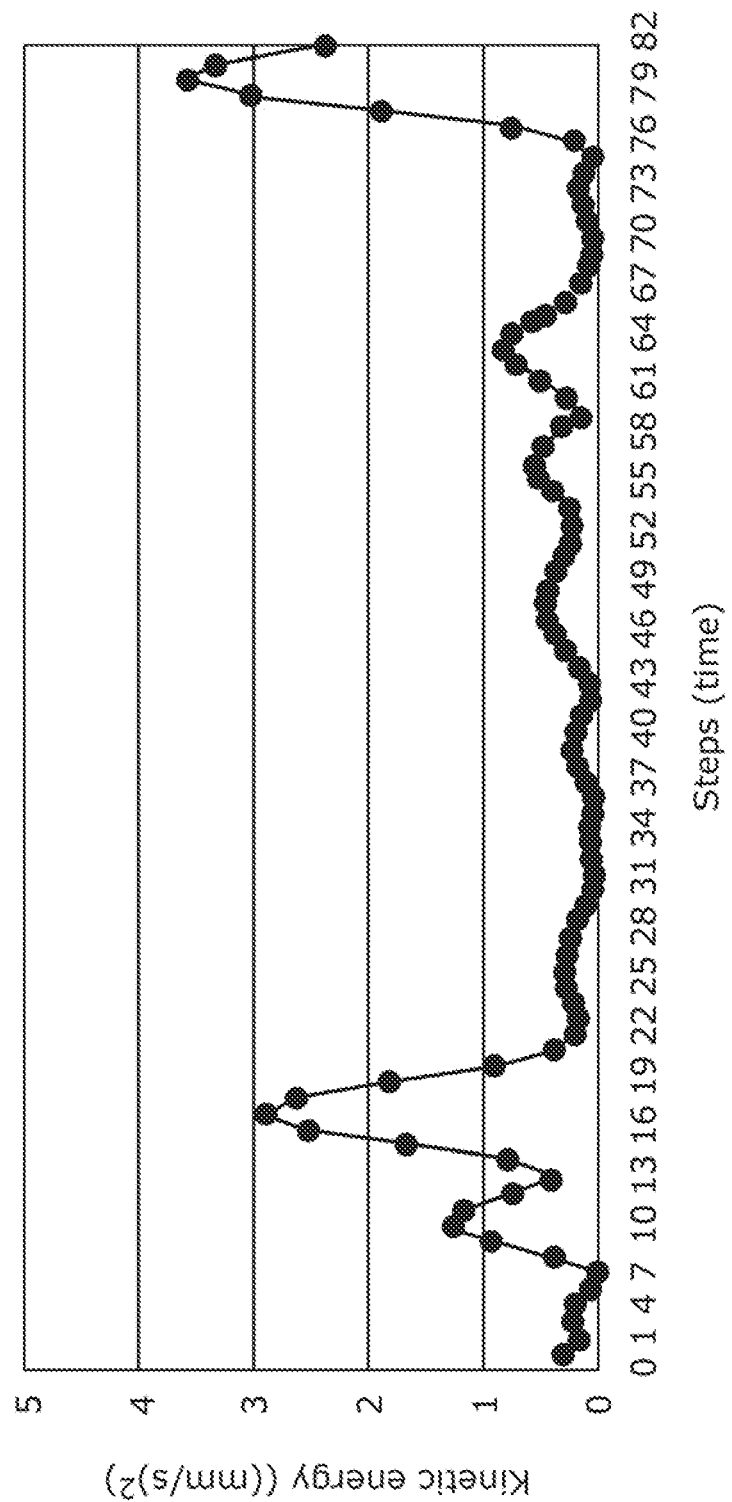
FIG. 19B illustrates changes over time in kinetic energy of another example of a point of a distal section according to Case 1.

FIG. 17A illustrates changes over time in kinetic energy of point n1 of proximal section n according to Case 1. FIG. 17B illustrates changes over time in kinetic energy of point n10 of proximal section n according to Case 1. FIG. 18A illustrates changes over time in kinetic energy of point m1 of middle section m according to Case 1. FIG. 18B illustrates changes over time in kinetic energy of point m10 of middle section m according to Case 1. FIG. 19A illustrates changes over time in kinetic energy of point f5 of distal section f according to Case 1. FIG. 19B illustrates changes over time in kinetic energy of point f10 of distal section f according to Case 1.

In FIG. 17A through FIG. 19B, the steps, which are units of time, are represented on the horizontal axis, and kinetic energy is represented on the vertical axis. Kinetic energy is a value calculated based on the square of the speed. The speed for calculating the kinetic energy may be a composite of the speeds in the x-, y-, and z-axis directions.

When the estimation information is a change over time in kinetic energy, the thickness of aneurysm wall 11 may be estimated using, for example, the following indicators: a maximum value, an integrated value, or a number of peaks of the kinetic energy. When the estimation information is a change over time in kinetic energy, just as when the estimation information is a change over time in speed, the larger these indicator values are, the more easily aneurysm wall 11 is stretched by pulsation and the thinner aneurysm wall 11 is estimated to be.

Next, points n1 and n10 in proximal section n will be compared with reference to FIG. 17A and FIG. 17B. The difference between the maximum and minimum kinetic energies at point n1 illustrated in FIG. 17A is greater than the difference between the maximum and minimum kinetic energies at point n10 illustrated in FIG. 17B. Therefore, because point n1 moves more from the origin than point n10 does, aneurysm wall 11 is easily stretched at point n1 by pulsation, and thus aneurysm wall 11 in the vicinity of point n1 is estimated to be thinner than aneurysm wall 11 in the vicinity of point n10.

Next, points m1 and m10 in middle section m will be compared with reference to FIG. 18A and FIG. 18B, and points f5 and f10 in distal section f will be compared with reference to FIG. 19A and FIG. 19B. The difference between the maximum and minimum kinetic energies at point m1 is greater than the difference between the maximum and minimum kinetic energies at point m10. Therefore, aneurysm wall 11 in the vicinity of point m1 is estimated to be thinner than aneurysm wall 11 in the vicinity of point m10. Similarly, the difference between the maximum and minimum kinetic energies at point f5 is greater than the difference between the maximum and minimum kinetic energies at point f10. Therefore, aneurysm wall 11 in the vicinity of point f5 is estimated to be thinner than aneurysm wall 11 in the vicinity of point f10.

Next, proximal section n, middle section m, and distal section f will be compared with reference to FIG. 17A through FIG. 19B. Here, the thickness of aneurysm wall 11 is estimated using, for example, the integrated values of the kinetic energies obtained from FIG. 17A through FIG. 19B as an indicator. For example, the sum of the integrated values of the kinetic energies of aneurysm wall 11 in proximal section n is the sum of the integrated values of the kinetic energies at points n1 and n10. For example, the sum of the integrated values of the kinetic energies of aneurysm wall 11 in middle section m is the sum of the integrated values of the kinetic energies at points m1 and m10. For example, the sum of the integrated values of the kinetic energies of aneurysm wall 11 in distal section f is the sum of the integrated values of the kinetic energies at points f5 and f10. As FIG. 17A through FIG. 19B illustrate, the sum of the integrated values of the kinetic energies of aneurysm wall 11 in proximal section n, the sum of the integrated values of the kinetic energies of aneurysm wall 11 in the middle section m, and the sum of the integrated values of the kinetic energies of aneurysm wall 11 in the distal section f increase in the stated order. Accordingly, it is estimated that aneurysm wall 11 becomes thinner from proximal section n toward distal section f.

The following process may be performed as another method by which the thickness of aneurysm wall 11 is estimated. The thickness of aneurysm wall 11 may be estimated by calculating the total of the integrated values of the kinetic energies of aneurysm wall 11 in the vicinity of the points in the 0 o'clock to 11 o'clock directions for each of proximal section n, middle section m, and distal section f, and comparing the calculated totals.

Next, an example in which the estimation information is a spring constant obtained from the displacement and the acceleration will be described. Cerebral aneurysm 10 can be considered to be in spring motion because of its amplitude motion in accordance with the pulsation of the heart.

Figure 20A:
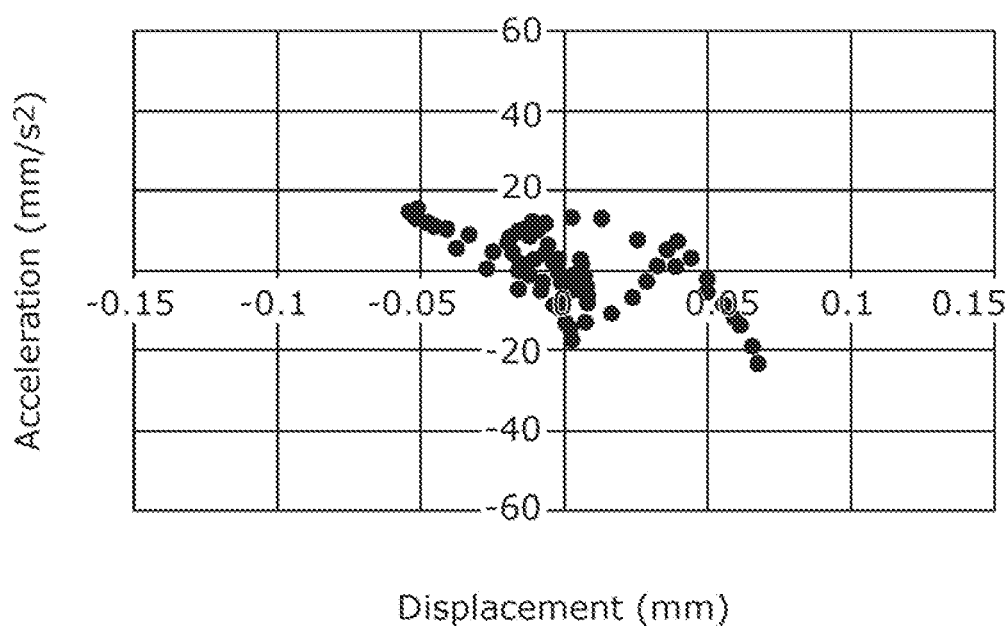
FIG. 20A illustrates acceleration and displacement from a predetermined origin in the z-axis direction of one example of a point of a distal section according to Case 1.
Figure 20B:
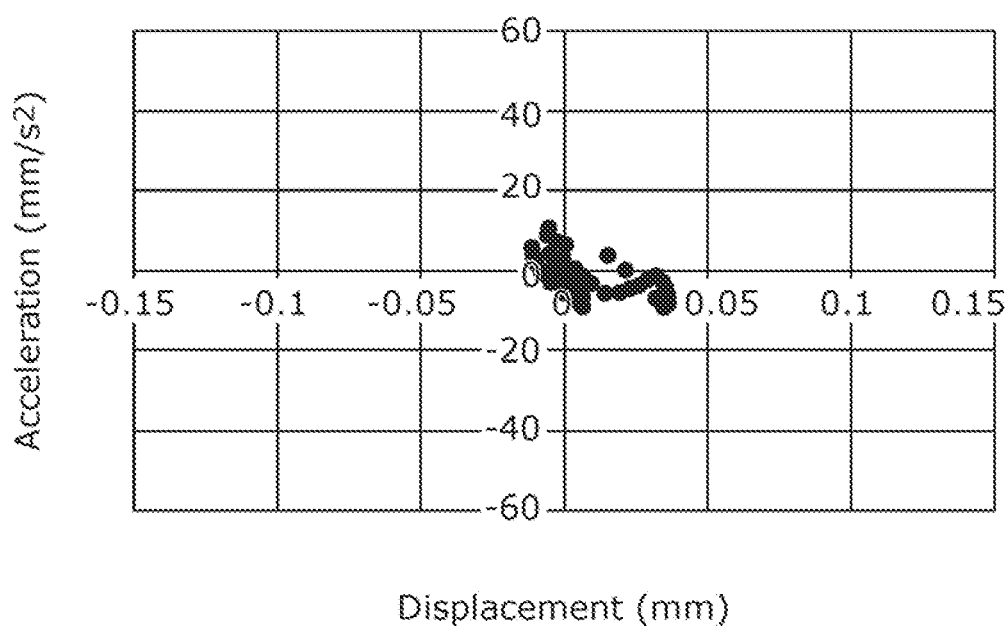
FIG. 20B illustrates acceleration and displacement from a predetermined origin in the z-axis direction of another example of a point of a distal section according to Case 1.
Figure 21A:
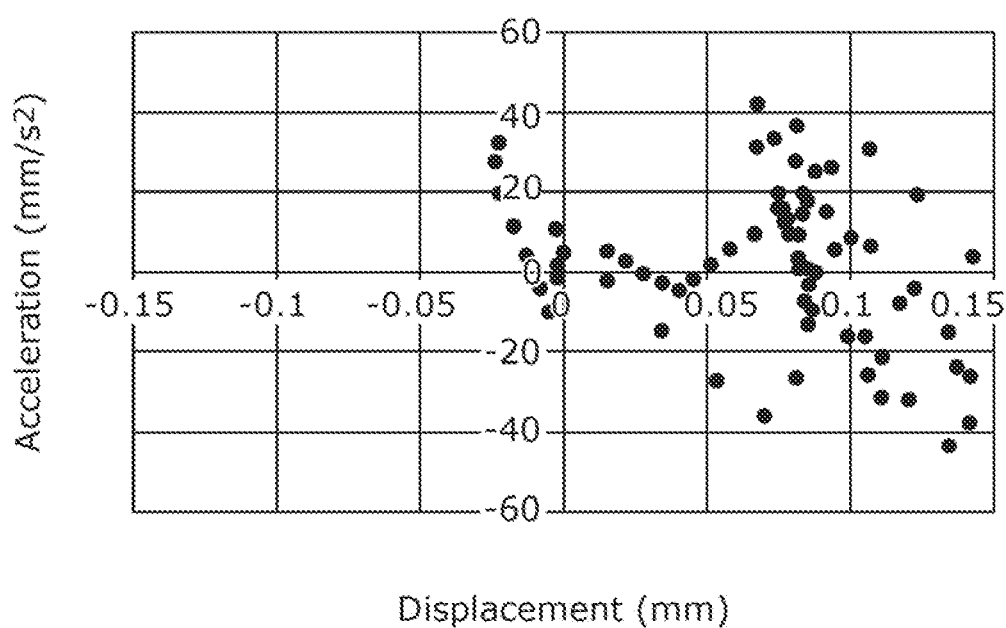
FIG. 21A illustrates acceleration and displacement from a predetermined origin in the x-axis direction of one example of a point of a distal section according to Case 1.

FIG. 20A illustrates acceleration and displacement from a predetermined origin in the z-axis direction of point f5 of distal section f according to Case 1. FIG. 20B illustrates acceleration and displacement from a predetermined origin in the z-axis direction of point f10 of distal section f according to Case 1. FIG. 21A illustrates acceleration and displacement from a predetermined origin in the x-axis direction of point f5 of distal section f according to Case 1. FIG. 21B illustrates acceleration and displacement from a predetermined origin in the x-axis direction of point f10 of distal section f according to Case 1. The predetermined origin can be determined in advance.

The equation for motion is shown in Equation (1) below, where F is force (in units of mN), m is mass (in units of kg), and a is acceleration (in units of mm/s$^2$). An equation based on Hooke's law is shown in Equation (2) below, where k is the spring constant (in units of N/mm), u is displacement (in units of mm), and a, 13, and y are constants. Here, displacement u is a third-order function.

[Math. 1]
$$F=ma \quad (1)$$

[Math. 2]
$$F=-k(u-\alpha)(u-\beta)(u-\gamma) \quad (2)$$

Since force F is equal in Equations (1) and (2), Equation (3) shown below can be derived.

[Math. 3]
$$ma=-k(u-\alpha)(u-\beta)(u-\gamma) \quad (3)$$

Acceleration a is thus a function dependent on displacement u. Displacement u is one of the displacements in the x-, y-, and z-axes.

Regarding the present embodiment, the inventor has discovered that in the direction in which cerebral aneurysm 10 extends from parent blood vessel 20 (the x-axis direction), acceleration a corresponds to a third-order function of displacement u, and in the plane orthogonal to the direction in which cerebral aneurysm 10 extends from parent blood vessel 20 (the yz-plane), acceleration a corresponds to a first-order function of displacement u. The coefficient of the third-order function of displacement u is −k/m, and the coefficient of the first-order function of displacement u is −k(αβ+βγ+γα)/m.

Accordingly, in the diagrams related to the yz plane in FIG. 20A and FIG. 20B, acceleration a corresponds to a first-order function of displacement z. For example, the slope of the line connecting the point where acceleration a is maximum and the point where acceleration a is minimum corresponds to −k(αβ+βγ+γα)/m. The smaller the slope of the straight line, i.e., the smaller the spring constant is, the greater the movement of the points in the 0 o'clock to 11 o'clock directions from the origin is, the more easily aneurysm wall 11 is stretched by the force imparted by the pulsation is, and thus the thinner aneurysm wall 11 corresponding to the points in the 0 o'clock to 11 o'clock directions is estimated to be.

Therefore, aneurysm wall 11 in the vicinity of point f5 is estimated to be thinner than aneurysm wall 11 in the vicinity of point f10 because the slope of the straight line at point f5 illustrated in FIG. 20A is smaller than that at point f10 illustrated in FIG. 20B.

The slope of the line connecting the point where displacement u is maximum and the point where displacement u is minimum may be used. In such cases, the slope of the line connecting the point where displacement x is maximum and the point where displacement x is minimum may be used.

Figure 22A:
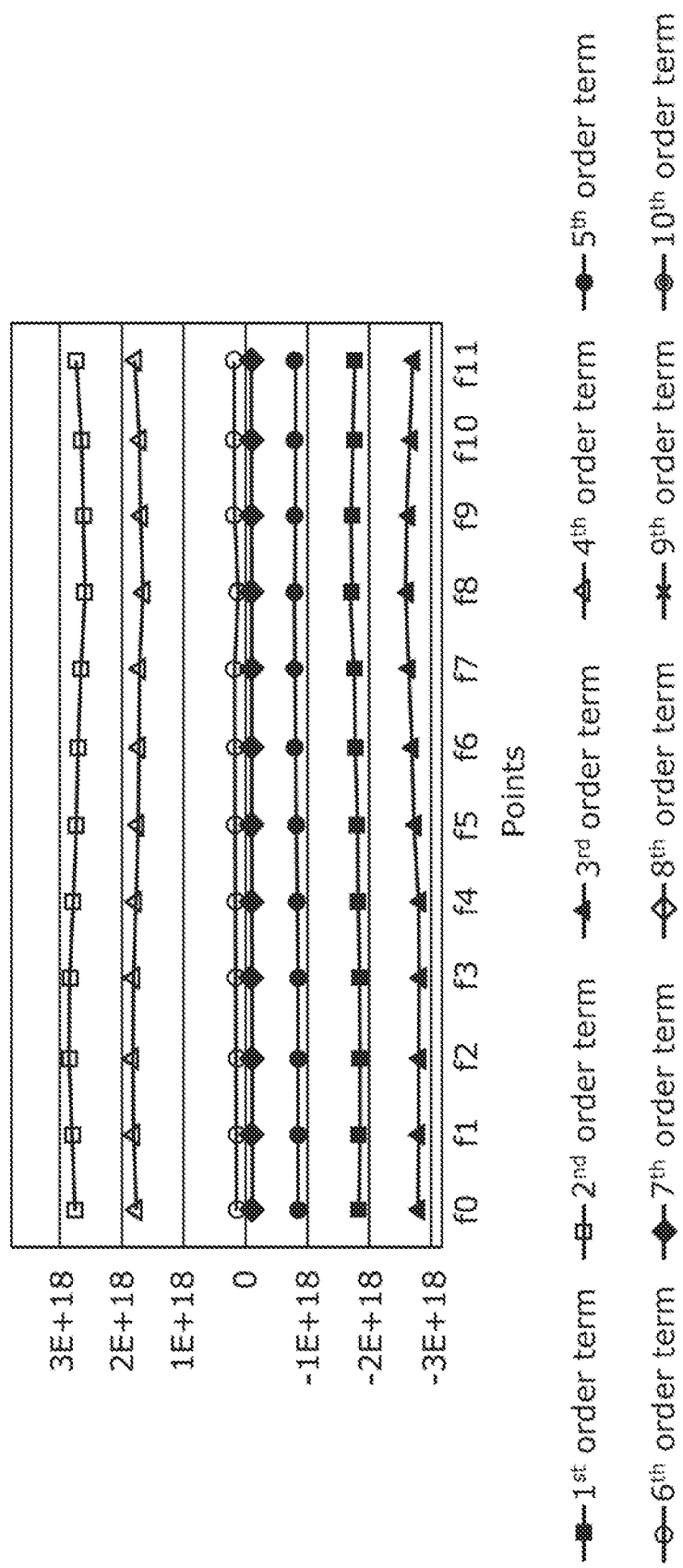
FIG. 22A illustrates Fourier coefficients obtained from changes in displacement over time of points of a distal section according to Case 2.
Figure 22B:
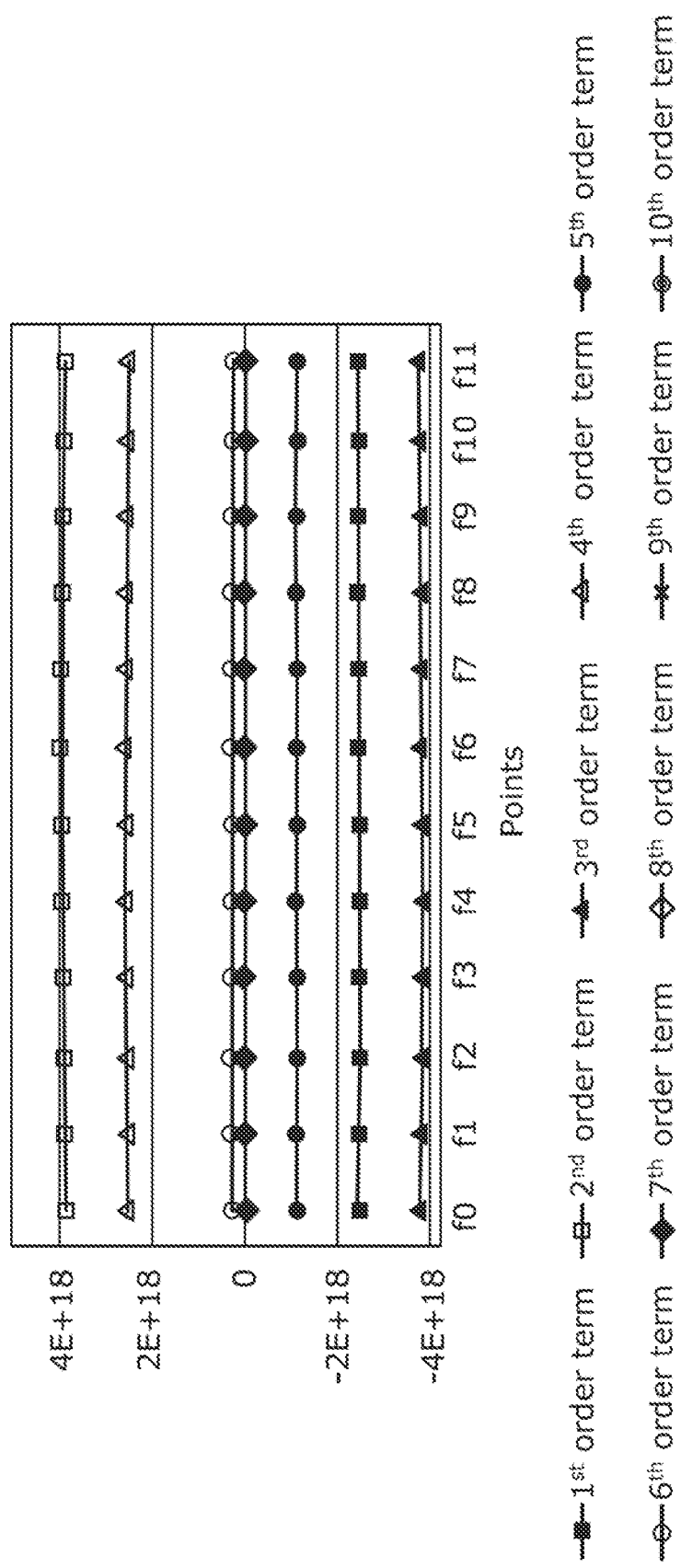
FIG. 22B illustrates Fourier coefficients obtained from changes in displacement over time of points of a distal section according to Case 3.

In the diagrams related to the x-axis direction in FIG. 21A and FIG. 22B, acceleration a corresponds to a third-order function of displacement x. As described above, the coefficient of the third-order function of displacement x is −k/m, and the smaller the spring constant is, the greater the movement of the points in the 0 o'clock to 11 o'clock directions from the origin is, the more easily aneurysm wall 11 is stretched by the force imparted by the pulsation is, and thus the thinner aneurysm wall 11 corresponding to the points in the 0 o'clock to 11 o'clock directions is estimated to be.

Although there is no high correlation between the values of displacement and acceleration in FIG. 21A and FIG. 21B, it is expected that a higher correlation between the values of displacement and acceleration can be obtained as the technology relevant to the present embodiment improves.

Next, an example in which the estimation information is a Fourier coefficient obtained from changes in displacement over time will be described.

Here, the estimation information will be described using Cases 2 and 3 described above as examples according to the present embodiment.

FIG. 22A illustrates Fourier coefficients obtained from changes in displacement over time of points f0 through f11 of distal section f according to Case 2. FIG. 22B illustrates Fourier coefficients obtained from changes in displacement over time of points f0 through f11 of distal section f according to Case 3.

In FIG. 22A and FIG. 22B, the plurality of predetermined points f0 through f11 are represented on the horizontal axis, and values of Fourier coefficients when changes in displacement over time of points f0 through f11 of distal section f are Fourier expanded are represented on the vertical axis. Here, changes in displacement over time of points f0 through f11 of distal section f are expanded through the tenth-order term, and lines corresponding to the first-through tenth-order terms are illustrated in FIG. 22A and FIG. 22B.

When the estimation information is a Fourier coefficient obtained from changes in displacement over time, for example, the maximum value of the Fourier coefficients or the difference between the maximum and minimum values of the Fourier coefficients is used as an indicator. The larger the maximum value of the Fourier coefficients is, the larger the amplitude of the corresponding frequency is, and thus the more easily aneurysm wall 11 is stretched by pulsation and the thinner aneurysm wall 11 is estimated to be.

The maximum value of the Fourier coefficients is, for example, the maximum value among the displacements of the Fourier coefficients of the first- to tenth-order terms at points f0 to f11. For example, in Case 2, the maximum value of Fourier coefficients is approximately 3×1018, as indicated by the second-order term in FIG. 22A, and in Case 3, the maximum value of Fourier coefficients is approximately 4×1018, as indicated by the second-order term in FIG. 22B. Stated differently, Case 3 estimates aneurysm wall 11 in distal section f of cerebral aneurysm 10 to be thinner than Case 2 does.

In FIG. 22A and FIG. 22B, distal section f is used as one example, but the tendency for aneurysm wall 11 in distal section f of cerebral aneurysm 10 to become thinner in Case 3 compared to Case 2 can also be seen in proximal section n and middle section m as well.

As described above, in Case 1, it is estimated that aneurysm wall 11 becomes thinner from proximal section n toward distal section f. Moreover, in Case 1, aneurysm wall 11 in the vicinity of point n1 is estimated to be thinner than aneurysm wall 11 in the vicinity of point n10, aneurysm wall 11 in the vicinity of point m1 is estimated to be thinner than aneurysm wall 11 in the vicinity of point m10, and aneurysm wall 11 in the vicinity of point f5 is estimated to be thinner than aneurysm wall 11 in the vicinity of point f10.

Moreover, in Case 2 and Case 3, Case 3 estimates aneurysm wall 11 of cerebral aneurysm 10 to be thinner than Case 2 does.

Next, the thicknesses of aneurysm wall 11 revealed by craniotomy in Cases 1, 2, and 3 will be described. In craniotomy, the thickness of aneurysm wall 11 can be estimated because a thin part of aneurysm wall 11 appears red and a thick part of aneurysm wall 11 appears white. The thicknesses of aneurysm wall 11 in Cases 1, 2, and 3 revealed by craniotomy confirmed a similar trend to the thicknesses of aneurysm wall 11 estimated using the blood vessel wall thickness estimation method according to the present embodiment.

As described above, it is possible to generate estimation information for estimating the thickness of a blood vessel wall using the blood vessel wall thickness estimation method according to the present embodiment. The thickness of the blood vessel wall estimated based on the estimation information showed the same trend as the thickness of the blood vessel wall obtained by craniotomy. In other words, the blood vessel wall thickness estimation method can generate highly accurate information about the wall thickness in the vicinity of a plurality of predetermined points in the blood vessel wall. In the present embodiment, for example, the thickness of aneurysm wall 11 of cerebral aneurysm 10 is estimated.

Advantageous Effects, Etc.

As described above, the blood vessel wall thickness estimation method includes obtaining (S101), based on a video including a blood vessel wall obtained using four-dimensional angiography, positions of a plurality of given points in the blood vessel wall and behavioral information related to time in the video. The blood vessel wall thickness estimation method further includes: generating (S102) estimation information for estimating a thickness of the blood vessel wall based on the behavioral information obtained in the obtaining (S101); and outputting (S103) the estimation information generated in the generating (S102). The estimation information is information in which at least one of the following is visualized: a change in position over time; a change in speed over time; a change in acceleration over time; a change in kinetic energy over time; a spring constant obtained from the position and the acceleration, and a Fourier coefficient obtained from the change in the position over time.

Moreover, a computer program according to the present embodiment causes a computer to execute the above-described blood vessel wall thickness estimation method.

With this, in the blood vessel wall thickness estimation method, a video including the blood vessel wall is generated using a CT or MRI device and four-dimensional angiography. For example, compared to other techniques such as craniotomy, a video including the blood vessel wall can be obtained by a minimally invasive technique. The blood vessel wall thickness estimation method can generate estimation information for estimating the thickness of the blood vessel wall using the behavioral information related to the video. The thickness of the blood vessel wall estimated based on the estimation information showed the same trend as the thickness of the blood vessel wall obtained by craniotomy. In other words, the blood vessel wall thickness estimation method can generate highly accurate information about the wall thickness in the vicinity of a plurality of predetermined points in the blood vessel wall. In the present embodiment, for example, the thickness of aneurysm wall 11 of cerebral aneurysm 10 is estimated. Such information is useful, for example, for distinguishing between cerebral aneurysms that are likely to rupture and those that are unlikely to rupture, and for appropriately determining whether treatment is necessary.

Stated differently, the blood vessel wall thickness estimation method according to the present embodiment can generate highly accurate information about the blood vessel wall using a minimally invasive method, thereby providing useful information for applying specific measures for blood vessel diseases.

In the blood vessel wall thickness estimation method, the speed is a value obtained by calculating a time derivative of a position among the positions, and the kinetic energy is calculated based on a square of the speed.

This makes it possible to calculate kinetic energy, which is one of estimation information for estimating the thickness of the blood vessel wall, using the blood vessel wall thickness estimation method.

In the blood vessel wall thickness estimation method, the thickness of the blood vessel wall is the thickness of the blood vessel wall of an aneurysm.

In the blood vessel wall thickness estimation method, the thickness of the blood vessel wall is the thickness of the blood vessel wall of a cerebral aneurysm.

In the blood vessel wall thickness estimation method, the thickness of the blood vessel wall is the thickness of the blood vessel wall of an artery.

This enables the blood vessel wall thickness estimation method to estimate the thickness of an aneurysm, a cerebral aneurysm, or an artery as the thickness of the blood vessel wall.

Blood vessel wall thickness estimation device 100 includes obtainer 110 that obtains behavioral information based on a video including a blood vessel wall obtained using four-dimensional angiography, the behavioral information being numerical information about changes over time in positions of a plurality of predetermined points in the blood vessel wall. Blood vessel wall thickness estimation device 100 further includes: generator 120 that generates estimation information for estimating a thickness of the blood vessel wall based on the behavioral information obtained by obtainer 110; and outputter 130 that outputs the estimation information generated by generator 120. The estimation information is information in which at least one of the following is visualized: a change in displacement over time; a change in speed over time; a change in acceleration over time; a change in kinetic energy over time; a spring constant obtained from the displacement and the acceleration, and a Fourier coefficient obtained from the change in the displacement over time.

With this, in blood vessel wall thickness estimation device 100, a video including the blood vessel wall is generated using a CT or MRI device and four-dimensional angiography. For example, compared to other techniques such as craniotomy, a video including the blood vessel wall can be obtained by a minimally invasive technique. The blood vessel wall thickness estimation method can generate estimation information for estimating the thickness of the blood vessel wall using the behavioral information related to the video. The thickness of the blood vessel wall estimated based on the estimation information showed the same trend as the thickness of the blood vessel wall obtained by craniotomy. In other words, blood vessel wall thickness estimation device 100 can generate highly accurate information about the wall thickness in the vicinity of a plurality of predetermined points in the blood vessel wall. In the present embodiment, for example, the thickness of aneurysm wall 11 of cerebral aneurysm 10 is estimated. Such information is useful, for example, for distinguishing between cerebral aneurysms that are likely to rupture and those that are unlikely to rupture, and for appropriately determining whether treatment is necessary.

Stated differently, blood vessel wall thickness estimation device 100 according to the present embodiment can generate highly accurate information about the blood vessel wall using a minimally invasive method, thereby providing useful information for applying specific measures for blood vessel diseases.

Blood vessel wall thickness estimation system 1000 includes: blood vessel wall thickness estimation device 100 described above; video information processing device 300 that obtains the video and generates the behavioral information; and display 200 that displays the estimation information output by outputter 130.

With this, in blood vessel wall thickness estimation system 1000, a video including the blood vessel wall is generated using a CT or MRI device and four-dimensional angiography. For example, compared to other techniques such as craniotomy, a video including the blood vessel wall can be obtained by a minimally invasive technique. The blood vessel wall thickness estimation method can generate estimation information for estimating the thickness of the blood vessel wall using the behavioral information related to the video. The thickness of the blood vessel wall estimated based on the estimation information showed the same trend as the thickness of the blood vessel wall obtained by craniotomy. In other words, blood vessel wall thickness estimation system 1000 can generate highly accurate information about the wall thickness in the vicinity of a plurality of predetermined points in the blood vessel wall. In the present embodiment, for example, the thickness of aneurysm wall 11 of cerebral aneurysm 10 is estimated. Such information is useful, for example, for distinguishing between cerebral aneurysms that are likely to rupture and those that are unlikely to rupture, and for appropriately determining whether treatment is necessary.

Stated differently, blood vessel wall thickness estimation system 1000 according to the present embodiment can generate highly accurate information about the blood vessel wall using a minimally invasive method, thereby providing useful information for applying specific measures for blood vessel diseases.

Furthermore, by visualizing and displaying the estimation information, doctors, for example, can obtain highly accurate information about the thickness of the blood vessel wall.

Other Embodiments

Although the above describes the blood vessel wall thickness estimation method and the like according to an embodiment, the present invention is not limited to the above embodiment.

The above embodiment describes methods of obtaining behavioral information using actual cases and four-dimensional angiography. However, the methods of obtaining the behavioral information are not limited to these examples. For example, the behavioral information may be obtained by the two other exemplary methods described below.

In the first other example, behavioral information is obtained by using an artificially created aneurysm, an artificial heart connected to the artificial aneurysm, and an imaging device.

An artificial aneurysm includes an artificial blood vessel and an artificial aneurysm. Artificial blood vessels and artificial aneurysms are created to mimic human blood vessels and aneurysms that occur in human blood vessels. The artificial aneurysm may be made of, for example, a rubber material. For example, a silicone rubber or fluorine rubber or the like may be used. The artificial aneurysm may also be made of, for example, a silicone resin. As long as the artificial aneurysm is made of a flexible material, the material used for the artificial aneurysm is not limited to the above examples.

The artificial aneurysm is created utilizing image data obtained by CT or MRI as described above. This image data includes data on human blood vessels and aneurysms that have occurred in the blood vessels. The artificial aneurysm is created based on digital imaging and communications in medicine (DICOM) data related to the image data obtained above.

An artificial heart is a device that performs the pumping function of the human heart. The artificial heart and the artificial aneurysm are connected, and the artificial heart's pumping function is activated to cause the artificial aneurysm to move in a pulsating manner. The behavioral information is obtained using this movement of the artificial aneurysm and the imaging device.

The imaging device is, for example, a camera device capable of capturing still images and videos. The imaging device may further be a device capable of obtaining three-dimensional coordinates on the surface of the observation target. Such an imaging device can be used to obtain displacement or speed in a three-dimensional space defined by the surface of the observation target. Such an imaging system can obtain the three-dimensional coordinates on the surface of the observation target by imaging for 1, 5, or 10 seconds.

As described above, in the method according to the first other example, an imaging device images a pulsating artificial aneurysm to obtain three-dimensional coordinates, displacement in a three-dimensional space, or speed in a three-dimensional space defined by the surface of the artificial aneurysm. The behavioral information may be obtained based on this.

In the method according to the first other example, behavioral information can be obtained more easily than with the craniotomy method described above because the technique is less invasive.

In the method according to the second other example, a model animal in which an aneurysm has developed in a blood vessel and the imaging device described above are used to obtain behavioral information.

More specifically, the imaging device images blood vessels and aneurysms in the model animal to obtain three-dimensional coordinates, displacement in a three-dimensional space, or speed in a three-dimensional space defined by the surfaces of the blood vessels and aneurysms in the model animal. The behavioral information may be obtained based on this.

In the method according to the second other example, unlike a case involving a human as shown in the embodiment, a consent form and the like for the human subject of the case is not required. Additionally, since the surfaces of the blood vessels and aneurysms of the model animal can be patterned (for example, marked by spraying) for imaging, time evolution data of precise three-dimensional coordinates can be obtained. Furthermore, data on the blood vessels and aneurysms of the model animal can be obtained at equal time intervals (for example, once every two weeks). This makes it easier to obtain behavioral information than in the embodiment.

The above method can be used to easily obtain a large number of behavioral information, and consequently, a large number of estimation information can be obtained. This is expected to improve the accuracy of the information about the blood vessel wall.

A plurality of the estimation information described in the embodiment may be used in combination. For example, the thickness of the blood vessel wall may be estimated using a combination of a change over time in displacement and a change over time in kinetic energy.

Similarly, a plurality of indicators may be used in combination. For example, when the estimation information is a change over time in speed, the thickness of the blood vessel wall may be estimated using a combination of the maximum value of the speed and an integrated value of the absolute value of the speed.

Outputter 130 may output the thickness estimated as described above as an estimation result.

Although the embodiment describes the thickness of the blood vessel wall as the thickness of aneurysm wall 11 of cerebral aneurysm 10, the thickness of the blood vessel wall may be the thickness of the wall of a blood vessel including an artery or a vein, as described above. For example, when the thickness of the blood vessel wall is the thickness of the wall of a blood vessel including an artery or a vein, the degree of stenosis of the artery or the vein is estimated using the blood vessel wall thickness estimation method and the like according to the embodiment.

In the above embodiments, each element may be configured in the form of dedicated hardware or realized by executing a software program suitable for the element. Each element may be realized by means of a program executing unit, such as a central processing unit (CPU) or a processor, reading and executing a software program recorded on a recording medium such as a hard disk or semiconductor memory.

Note that embodiments resulting from variations of the above embodiments conceived by those skilled in the art, as well as embodiments resulting from arbitrary combinations of elements and functions in the above embodiments are included within the present invention so long as they do not depart from the scope of the present invention.

INDUSTRIAL APPLICABILITY

The blood vessel wall thickness estimation method according to the present disclosure can be used in various applications, such as medical devices and medical methods.

REFERENCE SIGNS LIST

10 cerebral aneurysm
11 aneurysm wall
12 parent blood vessel
100 blood vessel wall thickness estimation device
110 obtainer
120 generator
130 outputter
200 display
300 video information processing device
400 video capturing device
1000 blood vessel wall thickness estimation system
f distal section
m middle section
n proximal section
nmax maximum value
nmin minimum value
n0, n1, n2, n3, n4, n5, n6, n7, n8, n9, n10, n11, m0, m1, m2, m3, m4, m5, m6, m7, m8, m9, m10, m11, f0, f1, f2, f3, f4, f5, f6, f7, f8, f9, f10, f11 point
P subject
S101 obtaining step
S102 generating step
S103 outputting step

The invention claimed is:

1. A blood vessel wall thickness estimation method comprising:
   obtaining behavioral information based on a video including a blood vessel wall obtained using four-dimensional angiography, the behavioral information being numerical information about changes over time in positions of a plurality of predetermined points in the blood vessel wall;
   generating estimation information for estimating a thickness of the blood vessel wall based on the behavioral information obtained in the obtaining; and
   outputting the estimation information generated in the generating,
   wherein the estimation information is information in which at least one of the following is visualized: a change in displacement over time; a change in speed over time; a change in acceleration over time; a change in kinetic energy over time; a spring constant obtained from the displacement and the acceleration; or a Fourier coefficient obtained from the change in the displacement over time, and
   the outputting includes:
      when the change in the displacement over time is visualized in the estimation information, outputting the thickness of the blood vessel wall estimated based on an indicator of the displacement;
      when the change in the speed over time is visualized in the estimation information, outputting the thickness of the blood vessel wall estimated based on an indicator of the speed;
      when the change in the acceleration over time is visualized in the estimation information, outputting the thickness of the blood vessel wall estimated based on an indicator of the acceleration;
      when the change in the kinetic energy over time is visualized in the estimation information, outputting the thickness of the blood vessel wall estimated based on an indicator of the kinetic energy;
      when the spring constant is visualized in the estimation information, outputting the thickness of the blood vessel wall estimated based on a magnitude of the spring constant; and
      when the Fourier coefficient is visualized in the estimation information, outputting the thickness of the blood vessel wall estimated based on an indicator of the Fourier coefficient.

2. The blood vessel wall thickness estimation method according to claim 1,
   wherein the speed is a value obtained by calculating a time derivative of a position among the positions, and
   the kinetic energy is calculated based on a square of the speed.

3. The blood vessel wall thickness estimation method according to claim 1,
   wherein the thickness of the blood vessel wall is the thickness of the blood vessel wall of an aneurysm.

4. The blood vessel wall thickness estimation method according to claim 1,
wherein the thickness of the blood vessel wall is the thickness of the blood vessel wall of a cerebral aneurysm.

5. The blood vessel wall thickness estimation method according to claim 1,
wherein the thickness of the blood vessel wall is the thickness of the blood vessel wall of an artery.

6. A non-transitory recording medium having recorded thereon a program for causing a computer to execute the blood vessel wall thickness estimation method according to claim 1.

7. A blood vessel wall thickness estimation device comprising:
an obtainer that obtains behavioral information based on a video including a blood vessel wall obtained using four-dimensional angiography, the behavioral information being numerical information about changes over time in positions of a plurality of predetermined points in the blood vessel wall;
a generator that generates estimation information for estimating a thickness of the blood vessel wall based on the behavioral information obtained by the obtainer; and
an outputter that outputs the estimation information generated by the generator,
wherein the estimation information is information in which at least one of the following is visualized: a change in displacement over time; a change in speed over time; a change in acceleration over time; a change in kinetic energy over time; a spring constant obtained from the displacement and the acceleration; or a Fourier coefficient obtained from the change in the displacement over time, and
the outputter outputs:
when the change in the displacement over time is visualized in the estimation information, the thickness of the blood vessel wall estimated based on an indicator of the displacement;
when the change in the speed over time is visualized in the estimation information, the thickness of the blood vessel wall estimated based on an indicator of the speed;
when the change in the acceleration over time is visualized in the estimation information, the thickness of the blood vessel wall estimated based on an indicator of the acceleration;
when the change in the kinetic energy over time is visualized in the estimation information, the thickness of the blood vessel wall estimated based on an indicator of the kinetic energy;
when the spring constant is visualized in the estimation information, the thickness of the blood vessel wall estimated based on a magnitude of the spring constant; and
when the Fourier coefficient is visualized in the estimation information, the thickness of the blood vessel wall estimated based on an indicator of the Fourier coefficient.

8. A blood vessel wall thickness estimation system comprising:
the blood vessel wall thickness estimation device according to claim 7;
a video information processing device that obtains the video and generates the behavioral information; and
a display that displays the estimation information output by the outputter.

* * * * *